US011566255B2

(12) United States Patent
Howard et al.

(10) Patent No.: US 11,566,255 B2
(45) Date of Patent: Jan. 31, 2023

(54) EXPRESSION OF PEDV SEQUENCES IN PLANTS AND PLANT PRODUCED VACCINE FOR SAME

(71) Applicant: Mazen Animal Health, Inc., St. Joseph, MO (US)

(72) Inventors: John Howard, San Luis Obispo, CA (US); Erin Egelkrout, San Luis Obispo, CA (US); Celine Hayden, San Louis Obispo, CA (US)

(73) Assignee: MAZEN ANIMAL HEALTH INC., Ames, IA (US)

(*) Notice: Subject to any disclaimer, the term of this patent is extended or adjusted under 35 U.S.C. 154(b) by 689 days.

(21) Appl. No.: 16/566,330

(22) Filed: Sep. 10, 2019

(65) Prior Publication Data

US 2020/0080101 A1 Mar. 12, 2020

Related U.S. Application Data

(60) Provisional application No. 62/730,045, filed on Sep. 12, 2018.

(51) Int. Cl.
| | |
|---|---|
| *C12N 15/82* | (2006.01) |
| *C12N 7/00* | (2006.01) |
| *C07K 14/005* | (2006.01) |
| *A61K 39/225* | (2006.01) |
| *A61P 31/14* | (2006.01) |

(52) U.S. Cl.
CPC ........ *C12N 15/8258* (2013.01); *A61K 39/225* (2013.01); *A61P 31/14* (2018.01); *C07K 14/005* (2013.01); *C12N 7/00* (2013.01); *C12N 15/8257* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

2003/0163848 A1* 8/2003 Howard ............. C12N 15/8257
241/6

FOREIGN PATENT DOCUMENTS

WO 2015138455 A1 9/2015

OTHER PUBLICATIONS

Sequence alignment of instant SEQ ID No. 3 with Geneseq db access No. BEM83912 in CN 107158371 Sep. 2017.*
Machine translation of CN 107158371 Sep. 2017 by Shan etal Sep. 2017.*
Sequence alignment of instant SEQ ID No. 15 with Geneseq db access No. AAW59700 in WO9821344 Oct. 1998.*
"spike protein [Porcine epidemic diarrhea virus]", GenBank: AAM19716.1, 2 pages, Aug. 23, 2005.
"spike protein [Porcine epidemic diarrhea virus]", GenBank: AFL02627. 1, 2 pages, Aug. 15, 2012.
Bae et al., "Induction of antigen-specific systemic and mucosal immune responses by feeding animals transgenic plants expressing the antigen", Vaccine, vol. 21, pp. 4052-4058, Mar. 11, 2003.
Chung et al., "Genetic characterization of s1 domain of porcine epidemic diarrhea viruses spike proteins isolated in Korea", J. Immune Disord., vol. 1, 3 pages, Aug. 2017.
Di-Qiu et al., "High-level mucosal and systemic immune responses induced by oral administration with Lactobacillus-expressed porcine epidemic diarrhea virus (PEDV) S1 region combine with Lactobacillus-expressed N protein", Appl. Microbial Biotechnol., vol. 93, pp. 2437-2446, 2012.
Hayden et al., "Oral delivery of wafers made from HBsAg-expressing maize germ induces long-term immunological systemic and mucosal responses", Vaccine, vol. 33(25), pp. 2881-2886, Jun. 9, 2015.
Hou et al., "Oral Immunization against PEDV with Recombinant Lactobacillus casei Expressing Dendritic Cell-Targeting Peptide Fusing COE Protein of PEDV in Piglets", Viruses, vol. 10, 14 pages, Mar. 1, 2018.
Huy et al., "Immunogenicity of a neutralizing epitope from porcine epidemic diarrhea virus: M cell targeting ligand fusion protein expressed in transgenic rice calli", Plant Cell Rep., vol. 31, pp. 1933-1942, Jun. 13, 2012.
Kumar et al., "Prediction of endoplasmic reticulum resident proteins using fragmented amino acid composition and support vector machine", PeerJ, vol. 5, 24 pages, Sep. 4, 2017.
Kun et al., "Expression of Core Neutralizing Epitope Gene of Porcine Epidemic Diarrhea Virus in Maize", Journal of Agricultural Science and Technology, vol. 16(6), pp. 28-35, 2014.
Lamphear et al., "A corn-based delivery system for animal vaccines: an oral transmissible gastroenteritis virus vaccine boosts lactogenic immunity in swine", Vaccine, vol. 22, pp. 2420-2424, 2004.
Makadiya et al., "S1 domain of the porcine epidemic diarrhea virus spike protein as a vaccine antigen", Virology Journal, vol. 13:57, 10 pages, 2016.
Mohamazadeh et al., "Dendritic cell targeting of Bacillus anthracis protective antigen expressed by Lactobacillus acidophilus protects mice from lethal challenge", PNAS, vol. 106, No. 11, pp. 4331,4336, Mar. 17, 2009.
Oh et al., "Immunogenicity and protective efficacy of recombinant S1 domain of the porcine epidemic diarrhea virus spike protein", Arch. Virol., vol. 159, pp. 2977-2987, Jun. 25, 2014.
Piao et al., "Production of soluble truncated spike protein of porcine epidemic diarrhea virus from inclusion bodies of *Escherichia coli* through refolding", Protein Expression and Purification, vol. 126, pp. 77-83, May 30, 2016.

(Continued)

*Primary Examiner* — Shanon A. Foley
(74) *Attorney, Agent, or Firm* — McKee, Voorhees & Sease, PLC

(57) ABSTRACT

A plant produced vaccine for Porcine Epidemic Diarrhea Virus (PEDV) is provided where the Spike protein of the virus is expressed in a plant by introducing into a plant a construct comprising a promoter preferentially directing expression to seed of said plant, a nucleoic acid encoding the Spike protein and a nucleic acid targeting expression to the endoplasmic reticulum of the plant. The plant expresses the S1 polypeptide at levels of at least 10 mg/kg of seed of said plant. When orally administered to an animal, a protective response is observed including a serum antibody response.

18 Claims, 4 Drawing Sheets

Specification includes a Sequence Listing.

(56) References Cited

OTHER PUBLICATIONS

Streatfield et al., "2000 Congress Symposium on Molecular Farming: Development of an Edible Subunit Vaccine in Corn Against Enterotoxigenic Strains of *Escherichia Coli*", In Vitro Cell. Dev. Biol.-Plant, vol. 38, pp. 11-17, Jan. 2002.

Tien et al., "Improved expression of porcine epidemic diarrhea antigen by fusion with cholera toxin B subunit and chloroplast transformation in Nicotiana tabacum", Plant Cell, Tissue and Organ Culture, vol. 137, pp. 213-223, Jan. 21, 2019.

Van Noi et al., "Optimization of expression and purification of recombinant S1 domain of the porcine epidemic diarrhea virus spike (PEDV-SI) protein in *Escherichia coli*", Biotechnology & Biotechnological Equipment, vol. 31, No. 3, pp. 619-629, Mar. 15, 2017.

Wicht et al., "Proteolytic Activation of the Porcine Epidemic Diarrhea Coronavirus Spike Fusion Protein by Trypsin in Cell Culture", Journal of Virology, vol. 88, No. 14, pp. 7952-7961, Jul. 2014.

\* cited by examiner

```
                         SEQUENCE LISTING

<160> NUMBER OF SEQ ID NOS: 25

<210> SEQ ID NO 1
<211> LENGTH: 2238
<212> TYPE: DNA
<213> ORGANISM: Artificial Sequence
<220> FEATURE:
<223> OTHER INFORMATION: Synthetic construct

<400> SEQUENCE: 1
atggcgaaca agcacctgag ccttagcctc ttcctcgtgc tcctgggcct ctccgcctcc      60
ctcgcctccg gcgtcacaag gtgctcggct aacaccaact tccgcaggtt cttctccaag     120
ttcaacgtgc aggctcccgc cgtggtggtg ctcggcggct acctgccaat cggcgagaac     180
cagggcgtga attcaacgtg gtactgcgcg ggccagcacc ccacggcctc gggcgtccac     240
ggcatcttcg tgagccacat ccgcggcggc cacggcttcg agatcggcat ctcgcaggag     300
cccttcgacc catcgggcta ccagctctac ctgcacaagg ccacgaacgg caacacgaac     360
gctaccgcca ggctgaggat ctgccagttc ccctccatca agaccctggg cccaaccgcg     420
aacaacgacg tgaccacggg caggaactgc ctgttcaaca aggccatccc ggcgcacatg     480
tccgagcaca gcgtcgtggg catcacgtgg gacaacgacc gcgtcaccgt gttcagcgac     540
```

| | | |
|---|---|---|
| aagatctact acttctactt caagaacgac tggtccaggg tcgccaccaa gtgctacaac | 600 | |
| agcggcggct gcgcgatgca gtatgtgtac gagccgacct actacatgct gaacgtgacg | 660 | |
| tcggcgggcg aggacggcat cagctaccag ccctgcacgg ccaactgcat cggctacgcc | 720 | |
| gcgaacgtgt tcgccacgga gcccaacggc cacatcccag agggcttctc cttcaacaac | 780 | |
| tggttcctcc tgtccaacga cagcaccctg gtccacggca aggtcgtgag caaccagccg | 840 | |
| ctcctggtga actgcctcct ggcgatcccc aagatctacg cctcggcca gttcttctcc | 900 | |
| ttcaaccaga cgatcgacgg cgtctgcaac ggcgcggccg tgcagagggc tcccgaggcg | 960 | |
| ctgaggttca acatcaacga cacctccgtc atcctggcgg agggcagcat cgtgctccac | 1020 | |
| acggccctgg gcacgaactt ctccttcgtg tgcagcaact ccagcaaccc ccacctcgcc | 1080 | |
| acgttcgcca tcccctgggg cgctacccag gtccccatct actgcttcct gaaggtggac | 1140 | |
| acctacaaca gcaccgtcta caagttcctg gccgtgctgc cgcccacggt ccgcgagatc | 1200 | |
| gtgatcacca agtacggcga cgtctacgtg aacggcttcg gctacctcca cctgggcctc | 1260 | |
| ctggacgcgg tcaccatcaa cttcaccggc cacggcacgg acgacgacgt gtccggcttc | 1320 | |
| tggacgatcg ccagcaccaa cttcgtggac gccctgatcg aggtgcaggg caccgccatc | 1380 | |
| cagcgcatcc tctactgcga cgacccggtg tcccagctga agtgcagcca ggtggcgttc | 1440 | |
| gacctcgacg acggcttcta ccccatctcc agcaggaacc tcctgtccca cgagcagccg | 1500 | |
| atcagcttcg tcacgctccc ctccttcaac gaccacagct tcgtcaacat caccgtgtcc | 1560 | |
| gcttccttcg gtggccactc gggcgctaac ctgatcgcca cgacaccac gatcaacggc | 1620 | |
| ttctccagct tctgcgtgga cacgaggcag ttcaccatct ccctcttcta caacgtcacg | 1680 | |
| aacagctacg gctacgtgtc caagagccag gactccaact gcccgttcac cctccagagc | 1740 | |
| gtcaacgact acctgtcctt cagcaagttc tgcgtgtcca cgagcctgct ggcttcggcc | 1800 | |
| tgcaccatcg acctgttcgg ctaccccgag ttcggctccg cgtcaagtt cacgagcctc | 1860 | |
| tacttccagt tcaccaaggg cgagctcatc acgggcaccc caagccact ggagggcgtc | 1920 | |
| acggacgtga gcttcatgac cctggacgtg tgcaccaagt acacgatcta cggcttcaag | 1980 | |
| ggcgagggca tcatcaccct cacgaactca agctttctgg ccggcgtcta ctacacctcc | 2040 | |
| gacagcggcc agctcctggc cttcaagaac gtgacctcgg cgccgtcta ctcggtgacg | 2100 | |
| ccctgctcct tcagcgagca ggctgcctac gtggacgacg acatcgtcgg cgtgatctcc | 2160 | |
| agcctctcct cttcgacttt caactcaacc cgcgagctgc ccggcttctt ctaccattcc | 2220 | |
| aaggacgagc tctgatag | 2238 | |

<210> SEQ ID NO 2
<211> LENGTH: 2415
<212> TYPE: DNA
<213> ORGANISM: Artificial Sequence
<220> FEATURE:
<223> OTHER INFORMATION: Synthetic construct

<400> SEQUENCE: 2

| | | |
|---|---|---|
| atggcgaaca agcacctgag ccttagcctc ttcctcgtgc tcctgggcct ctccgcctcc | 60 | |
| ctcgcctccg gcgtcacaag gtgctcggct aacaccaact tccgcaggtt cttctccaag | 120 | |
| ttcaacgtgc aggctcccgc cgtggtggtg ctcggcggct acctgccaat cggcgagaac | 180 | |
| cagggcgtga attcaacgtg gtactgcgcg ggccagcacc ccacggcctc gggcgtccac | 240 | |
| ggcatcttcg tgagccacat ccgcggcggc cacggcttcg agatcggcat ctcgcaggag | 300 | |

```
cccttcgacc catcgggcta ccagctctac ctgcacaagg ccacgaacgg caacacgaac    360
gctaccgcca ggctgaggat ctgccagttc ccctccatca agaccctggg cccaaccgcg    420
aacaacgacg tgaccacggg caggaactgc ctgttcaaca aggccatccc ggcgcacatg    480
tccgagcaca cgtcgtggg catcacgtgg acaacgacc gcgtcaccgt gttcagcgac      540
aagatctact acttctactt caagaacgac tggtccaggg tcgccaccaa gtgctacaac    600
agcggcggct cgcgcgatgca gtatgtgtac gagccgacct actacatgct gaacgtgacg   660
tcggcgggcg aggacggcat cagctaccag ccctgcacgg ccaactgcat cggctacgcc    720
gcgaacgtgt cgccacggga gcccaacggc acatcccag agggcttctc cttcaacaac     780
tggttcctcc tgtccaacga cagcaccctg gtccacggca aggtcgtgag caaccagccg    840
ctcctggtga actgcctcct ggcgatcccc aagatctacg gcctcggcca gttcttctcc    900
ttcaaccaga cgatcgacgg cgtctgcaac ggcgcggccg tgcagagggc tcccgaggcg    960
ctgaggttca acatcaacga cacctccgtc atcctggcgg agggcagcat cgtgctccac   1020
acgggccctgg gcacgaactt ctccttcgtg tgcagcaact ccagcaaccc ccactcgcc   1080
acgttcgcca tcccctgggg cgctacccag gtccctact actgcttcct gaaggtggac    1140
acctacaaca gcaccgtcta caagttcctg gccgtgctgc cgcccacggt ccgcgagatc    1200
gtgatcacca agtacggcga cgtctacgtg aacggcttcg gctacctcca cctgggcctc    1260
ctggacgcgt caccatcaa cttcaccggc cacggcacgg acgacgacgt gtccggcttc   1320
tggacgatcg ccagcaccaa cttcgtggac gccctgatcg aggtgcaggg caccgccatc   1380
cagcgcatcc tctactgcga cgacccggtg tcccagctga agtgcagcca ggtggcgttc   1440
gacctcgacg acggcttcta ccccatctcc agcaggaacc tcctgtccca cgagcagccg   1500
atcagcttcg tcacgctccc ctccttcaac gaccacagct tcgtcaacat caccgtgtcc   1560
gcttccttcg gtggccactc gggcgctaac ctgatcgcca gcgacaccac gatcaacggc   1620
ttctccagct tctgcgtgga cacgaggcag ttcaccatct ccctcttcta caacgtcacg   1680
aacagctacg gctacgtgtc caagagccag gactccaact gcccgttcac cctccagagc   1740
gtcaacgact acctgtcctt cagcaagttc tgcgtgtcca cgagcctgct ggcttcggcc   1800
tgcaccatcg acctgttcgg ctaccccgag ttcggctccg gcgtcaagtt cacgagcctc   1860
tacttccagt tcaccaaggg cgagctcatc acgggcaccc ccaagccact ggagggcgtc   1920
acggacgtga gcttcatgac cctggacgtg tgcaccaagt acacgatcta cggcttcaag   1980
ggcgagggca tcatcaccct cacgaactca agctttctgg ccggcgtcta ctacacctcc   2040
gacagcggcc agctcctggc cttcaagaac gtgacctcgg gcgccgtcta ctcggtgacg   2100
ccctgctcct tcagcgagca ggctgcctac gtggacgacg acatcgtcgg cgtgatctcc   2160
agcctctcct cttcgacttt caactcaacc cgcgagctgc ccggcttctt ctaccattcc   2220
aacgatggct ccaattgcac agagcctgtg ttggtgtaca gcaacatcgg tgtttgcaaa   2280
tctggcagca ttggctacgt cccatcccag tctggccaag tgaagattgc cccgaccgtt   2340
actgggaaca tcagcattcc caccaacttc agcttctacc cctcctacca cagcaccccca   2400
cagcgcccct gatag                                                    2415
```

<210> SEQ ID NO 3
<211> LENGTH: 716
<212> TYPE: PRT
<213> ORGANISM: Porcine epidemic diarrhea virus

<400> SEQUENCE: 3

```
Val Thr Arg Cys Ser Ala Asn Thr Asn Phe Arg Arg Phe Phe Ser Lys
1               5                   10                  15

Phe Asn Val Gln Ala Pro Ala Val Val Leu Gly Gly Tyr Leu Pro
            20                  25                  30

Ile Gly Glu Asn Gln Gly Val Asn Ser Thr Trp Tyr Cys Ala Gly Gln
        35                  40                  45

His Pro Thr Ala Ser Gly Val His Gly Ile Phe Val Ser His Ile Arg
    50                  55                  60

Gly Gly His Gly Phe Glu Ile Gly Ile Ser Gln Glu Pro Phe Asp Pro
65              70                  75                  80

Ser Gly Tyr Gln Leu Tyr Leu His Lys Ala Thr Asn Gly Asn Thr Asn
                85                  90                  95

Ala Thr Ala Arg Leu Arg Ile Cys Gln Phe Pro Ser Ile Lys Thr Leu
                100                 105                 110

Gly Pro Thr Ala Asn Asn Asp Val Thr Thr Gly Arg Asn Cys Leu Phe
            115                 120                 125

Asn Lys Ala Ile Pro Ala His Met Ser Glu His Ser Val Val Gly Ile
    130                 135                 140

Thr Trp Asp Asn Asp Arg Val Thr Val Phe Ser Asp Lys Ile Tyr Tyr
145                 150                 155                 160

Phe Tyr Phe Lys Asn Asp Trp Ser Arg Val Ala Thr Lys Cys Tyr Asn
                165                 170                 175

Ser Gly Gly Cys Ala Met Gln Tyr Val Tyr Glu Pro Thr Tyr Tyr Met
                180                 185                 190

Leu Asn Val Thr Ser Ala Gly Glu Asp Gly Ile Ser Tyr Gln Pro Cys
        195                 200                 205

Thr Ala Asn Cys Ile Gly Tyr Ala Ala Asn Val Phe Ala Thr Glu Pro
    210                 215                 220

Asn Gly His Ile Pro Glu Gly Phe Ser Phe Asn Asn Trp Phe Leu Leu
225                 230                 235                 240

Ser Asn Asp Ser Thr Leu Val His Gly Lys Val Val Ser Asn Gln Pro
                245                 250                 255

Leu Leu Val Asn Cys Leu Leu Ala Ile Pro Lys Ile Tyr Gly Leu Gly
                260                 265                 270

Gln Phe Phe Ser Phe Asn Gln Thr Ile Asp Gly Val Cys Asn Gly Ala
            275                 280                 285

Ala Val Gln Arg Ala Pro Glu Ala Leu Arg Phe Asn Ile Asn Asp Thr
    290                 295                 300

Ser Val Ile Leu Ala Glu Gly Ser Ile Val Leu His Thr Ala Leu Gly
305                 310                 315                 320

Thr Asn Phe Ser Phe Val Cys Ser Asn Ser Ser Asn Pro His Leu Ala
            325                 330                 335

Thr Phe Ala Ile Pro Leu Gly Ala Thr Gln Val Pro Tyr Tyr Cys Phe
            340                 345                 350

Leu Lys Val Asp Thr Tyr Asn Ser Thr Val Tyr Lys Phe Leu Ala Val
            355                 360                 365

Leu Pro Pro Thr Val Arg Glu Ile Val Ile Thr Lys Tyr Gly Asp Val
        370                 375                 380

Tyr Val Asn Gly Phe Gly Tyr Leu His Leu Gly Leu Leu Asp Ala Val
385                 390                 395                 400

Thr Ile Asn Phe Thr Gly His Gly Thr Asp Asp Asp Val Ser Gly Phe
                405                 410                 415
```

```
Trp Thr Ile Ala Ser Thr Asn Phe Val Asp Ala Leu Ile Glu Val Gln
                420                 425                 430

Gly Thr Ala Ile Gln Arg Ile Leu Tyr Cys Asp Asp Pro Val Ser Gln
            435                 440                 445

Leu Lys Cys Ser Gln Val Ala Phe Asp Leu Asp Asp Gly Phe Tyr Pro
        450                 455                 460

Ile Ser Ser Arg Asn Leu Leu Ser His Glu Gln Pro Ile Ser Phe Val
465                 470                 475                 480

Thr Leu Pro Ser Phe Asn Asp His Ser Phe Val Asn Ile Thr Val Ser
                485                 490                 495

Ala Ser Phe Gly Gly His Ser Gly Ala Asn Leu Ile Ala Ser Asp Thr
            500                 505                 510

Thr Ile Asn Gly Phe Ser Ser Phe Cys Val Asp Thr Arg Gln Phe Thr
        515                 520                 525

Ile Ser Leu Phe Tyr Asn Val Thr Asn Ser Tyr Gly Tyr Val Ser Lys
530                 535                 540

Ser Gln Asp Ser Asn Cys Pro Phe Thr Leu Gln Ser Val Asn Asp Tyr
545                 550                 555                 560

Leu Ser Phe Ser Lys Phe Cys Val Ser Thr Ser Leu Leu Ala Ser Ala
                565                 570                 575

Cys Thr Ile Asp Leu Phe Gly Tyr Pro Glu Phe Gly Ser Gly Val Lys
            580                 585                 590

Phe Thr Ser Leu Tyr Phe Gln Phe Thr Lys Gly Glu Leu Ile Thr Gly
        595                 600                 605

Thr Pro Lys Pro Leu Glu Gly Val Thr Asp Val Ser Phe Met Thr Leu
        610                 615                 620

Asp Val Cys Thr Lys Tyr Thr Ile Tyr Gly Phe Lys Gly Glu Gly Ile
625                 630                 635                 640

Ile Thr Leu Thr Asn Ser Ser Phe Leu Ala Gly Val Tyr Tyr Thr Ser
                645                 650                 655

Asp Ser Gly Gln Leu Leu Ala Phe Lys Asn Val Thr Ser Gly Ala Val
            660                 665                 670

Tyr Ser Val Thr Pro Cys Ser Phe Ser Glu Gln Ala Ala Tyr Val Asp
        675                 680                 685

Asp Asp Ile Val Gly Val Ile Ser Ser Leu Ser Ser Ser Thr Phe Asn
        690                 695                 700

Ser Thr Arg Glu Leu Pro Gly Phe Phe Tyr His Ser
705                 710                 715

<210> SEQ ID NO 4
<211> LENGTH: 767
<212> TYPE: PRT
<213> ORGANISM: Porcine epidemic diarrhea virus

<400> SEQUENCE: 4

Val Thr Arg Cys Ser Ala Asn Thr Asn Phe Arg Arg Phe Phe Ser Lys
1               5                   10                  15

Phe Asn Val Gln Ala Pro Ala Val Val Val Leu Gly Gly Tyr Leu Pro
                20                  25                  30

Ile Gly Glu Asn Gln Gly Val Asn Ser Thr Trp Tyr Cys Ala Gly Gln
            35                  40                  45

His Pro Thr Ala Ser Gly Val His Gly Ile Phe Val Ser His Ile Arg
        50                  55                  60

Gly Gly His Gly Phe Glu Ile Gly Ile Ser Gln Glu Pro Phe Asp Pro
65                  70                  75                  80
```

```
Ser Gly Tyr Gln Leu Tyr Leu His Lys Ala Thr Asn Gly Asn Thr Asn
                85              90              95

Ala Thr Ala Arg Leu Arg Ile Cys Gln Phe Pro Ser Ile Lys Thr Leu
            100             105             110

Gly Pro Thr Ala Asn Asn Asp Val Thr Thr Gly Arg Asn Cys Leu Phe
            115             120             125

Asn Lys Ala Ile Pro Ala His Met Ser Glu His Ser Val Val Gly Ile
130             135             140

Thr Trp Asp Asn Asp Arg Val Thr Val Phe Ser Asp Lys Ile Tyr Tyr
145             150             155             160

Phe Tyr Phe Lys Asn Asp Trp Ser Arg Val Ala Thr Lys Cys Tyr Asn
            165             170             175

Ser Gly Gly Cys Ala Met Gln Tyr Val Tyr Glu Pro Thr Tyr Tyr Met
            180             185             190

Leu Asn Val Thr Ser Ala Gly Glu Asp Gly Ile Ser Tyr Gln Pro Cys
            195             200             205

Thr Ala Asn Cys Ile Gly Tyr Ala Ala Asn Val Phe Ala Thr Glu Pro
            210             215             220

Asn Gly His Ile Pro Glu Gly Phe Ser Phe Asn Asn Trp Phe Leu Leu
225             230             235             240

Ser Asn Asp Ser Thr Leu Val His Gly Lys Val Val Ser Asn Gln Pro
            245             250             255

Leu Leu Val Asn Cys Leu Leu Ala Ile Pro Lys Ile Tyr Gly Leu Gly
            260             265             270

Gln Phe Phe Ser Phe Asn Gln Thr Ile Asp Gly Val Cys Asn Gly Ala
            275             280             285

Ala Val Gln Arg Ala Pro Glu Ala Leu Arg Phe Asn Ile Asn Asp Thr
            290             295             300

Ser Val Ile Leu Ala Glu Gly Ser Ile Val Leu His Thr Ala Leu Gly
305             310             315             320

Thr Asn Phe Ser Phe Val Cys Ser Asn Ser Ser Asn Pro His Leu Ala
            325             330             335

Thr Phe Ala Ile Pro Leu Gly Ala Thr Gln Val Pro Tyr Tyr Cys Phe
            340             345             350

Leu Lys Val Asp Thr Tyr Asn Ser Thr Val Tyr Lys Phe Leu Ala Val
            355             360             365

Leu Pro Pro Thr Val Arg Glu Ile Val Ile Thr Lys Tyr Gly Asp Val
            370             375             380

Tyr Val Asn Gly Phe Gly Tyr Leu His Leu Gly Leu Leu Asp Ala Val
385             390             395             400

Thr Ile Asn Phe Thr Gly His Gly Thr Asp Asp Val Ser Gly Phe
            405             410             415

Trp Thr Ile Ala Ser Thr Asn Phe Val Asp Ala Leu Ile Glu Val Gln
            420             425             430

Gly Thr Ala Ile Gln Arg Ile Leu Tyr Cys Asp Asp Pro Val Ser Gln
            435             440             445

Leu Lys Cys Ser Gln Val Ala Phe Asp Leu Asp Gly Phe Tyr Pro
450             455             460

Ile Ser Ser Arg Asn Leu Leu Ser His Glu Gln Pro Ile Ser Phe Val
465             470             475             480

Thr Leu Pro Ser Phe Asn Asp His Ser Phe Val Asn Ile Thr Val Ser
            485             490             495
```

```
Ala Ser Phe Gly Gly His Ser Gly Ala Asn Leu Ile Ala Ser Asp Thr
            500                 505                 510

Thr Ile Asn Gly Phe Ser Ser Phe Cys Val Asp Thr Arg Gln Phe Thr
            515                 520                 525

Ile Ser Leu Phe Tyr Asn Val Thr Asn Ser Tyr Gly Tyr Val Ser Lys
            530                 535                 540

Ser Gln Asp Ser Asn Cys Pro Phe Thr Leu Gln Ser Val Asn Asp Tyr
545                 550                 555                 560

Leu Ser Phe Ser Lys Phe Cys Val Ser Thr Ser Leu Leu Ala Ser Ala
                565                 570                 575

Cys Thr Ile Asp Leu Phe Gly Tyr Pro Glu Phe Gly Ser Gly Val Lys
            580                 585                 590

Phe Thr Ser Leu Tyr Phe Gln Phe Thr Lys Gly Glu Leu Ile Thr Gly
            595                 600                 605

Thr Pro Lys Pro Leu Glu Gly Val Thr Asp Val Ser Phe Met Thr Leu
            610                 615                 620

Asp Val Cys Thr Lys Tyr Thr Ile Tyr Gly Phe Lys Gly Glu Gly Ile
625                 630                 635                 640

Ile Thr Leu Thr Asn Ser Ser Phe Leu Ala Gly Val Tyr Tyr Thr Ser
                645                 650                 655

Asp Ser Gly Gln Leu Leu Ala Phe Lys Asn Val Thr Ser Gly Ala Val
            660                 665                 670

Tyr Ser Val Thr Pro Cys Ser Phe Ser Glu Gln Ala Ala Tyr Val Asp
            675                 680                 685

Asp Asp Ile Val Gly Val Ile Ser Ser Leu Ser Ser Ser Thr Phe Asn
            690                 695                 700

Ser Thr Arg Glu Leu Pro Gly Phe Phe Tyr His Ser Asn Asp Gly Ser
705                 710                 715                 720

Asn Cys Thr Glu Pro Val Leu Val Tyr Ser Asn Ile Gly Val Cys Lys
                725                 730                 735

Ser Gly Ser Ile Gly Tyr Val Pro Ser Gln Ser Gly Val Lys Ile
            740                 745                 750

Ala Pro Thr Val Thr Gly Asn Ile Ser Ile Pro Thr Asn Phe Ser
            755                 760                 765

<210> SEQ ID NO 5
<211> LENGTH: 72
<212> TYPE: DNA
<213> ORGANISM: Hordeum vulgare

<400> SEQUENCE: 5
atggcgaaca agcacctgag ccttagcctc ttcctcgtgc tcctgggcct ctccgcctcc    60
ctcgcctccg gc                                                       72

<210> SEQ ID NO 6
<211> LENGTH: 24
<212> TYPE: PRT
<213> ORGANISM: Hordeum vulgare

<400> SEQUENCE: 6

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 7
```

-continued

<211> LENGTH: 756
<212> TYPE: DNA
<213> ORGANISM: Artificial Sequence
<220> FEATURE:
<223> OTHER INFORMATION: Synthetic construct

<400> SEQUENCE: 7

| | | | | | |
|---|---|---|---|---|---|
| atggcgaaca | agcacctgag | ccttagcctc | ttcctcgtgc | tcctgggcct | ctccgcctcc | 60 |
| ctcgcctccg | gcgtgtccaa | cggctcaatc | ccagtggacg | aggtcatcca | gcacctccgc | 120 |
| aactggaact | tcacgtggaa | catcatcctc | accatcctcc | tggtggtcct | gcagtacggc | 180 |
| cactacaagt | actccgcctt | cctgtacggc | gtcaagatgg | cgatcctctg | gatcctctgg | 240 |
| cccctggtgc | tcgctctctc | cctgttcgac | gcttgggcca | gcttccaggt | gaactgggtc | 300 |
| ttcttcgcct | tctccatcct | catggcgtgc | atcaccctca | tgctgtggat | catgtacttc | 360 |
| gtcaacagca | tcaggctgtg | gaggaggacc | cactcctggt | ggagcttcaa | ccccgagacg | 420 |
| gacgctctcc | tgaccacctc | cgtcatgggc | aggcaggtgt | gcatccccgt | cctgggcgcc | 480 |
| ccaaccggcg | tgaccctcac | gctgctgtcg | ggcaccctcc | tggtggaggg | ctacaaggtg | 540 |
| gctaccggcg | tgcaggtcag | ccagctcccc | aacttcgtga | ccgtcgccaa | ggcgaccacg | 600 |
| acgatcgtgt | acggcagggt | gggcaggtcg | gtgaacgctt | cctcgggcac | cggctgggcg | 660 |
| ttctacgtga | ggtccaagca | cggcgactac | agcgcggtga | gcaaccccte | gtcggtcctg | 720 |
| actgattcgg | agaaggtcct | gcacctcgtg | tagtga | | | 756 |

<210> SEQ ID NO 8
<211> LENGTH: 250
<212> TYPE: PRT
<213> ORGANISM: Artificial Sequence
<220> FEATURE:
<223> OTHER INFORMATION: Synthetic construct

<400> SEQUENCE: 8

Met Ala Asn Lys His Leu Ser Leu Ser Leu Phe Leu Val Leu Leu Gly
1               5                   10                  15

Leu Ser Ala Ser Leu Ala Ser Gly Val Ser Asn Gly Ser Ile Pro Val
            20                  25                  30

Asp Glu Val Ile Gln His Leu Arg Asn Trp Asn Phe Thr Trp Asn Ile
        35                  40                  45

Ile Leu Thr Ile Leu Leu Val Val Leu Gln Tyr Gly His Tyr Lys Tyr
    50                  55                  60

Ser Ala Phe Leu Tyr Gly Val Lys Met Ala Ile Leu Trp Ile Leu Trp
65                  70                  75                  80

Pro Leu Val Leu Ala Leu Ser Leu Phe Asp Ala Trp Ala Ser Phe Gln
                85                  90                  95

Val Asn Trp Val Phe Phe Ala Phe Ser Ile Leu Met Ala Cys Ile Thr
            100                 105                 110

Leu Met Leu Trp Ile Met Tyr Phe Val Asn Ser Ile Arg Leu Trp Arg
        115                 120                 125

Arg Thr His Ser Trp Trp Ser Phe Asn Pro Glu Thr Asp Ala Leu Leu
    130                 135                 140

Thr Thr Ser Val Met Gly Arg Gln Val Cys Ile Pro Val Leu Gly Ala
145                 150                 155                 160

Pro Thr Gly Val Thr Leu Thr Leu Leu Ser Gly Thr Leu Leu Val Glu
                165                 170                 175

Gly Tyr Lys Val Ala Thr Gly Val Gln Val Ser Gln Leu Pro Asn Phe
            180                 185                 190

```
Val Thr Val Ala Lys Ala Thr Thr Thr Ile Val Tyr Gly Arg Val Gly
            195                 200                 205

Arg Ser Val Asn Ala Ser Ser Gly Thr Gly Trp Ala Phe Tyr Val Arg
        210                 215                 220

Ser Lys His Gly Asp Tyr Ser Ala Val Ser Asn Pro Ser Ser Val Leu
225                 230                 235                 240

Thr Asp Ser Glu Lys Val Leu His Leu Val
            245                 250

<210> SEQ ID NO 9
<211> LENGTH: 713
<212> TYPE: PRT
<213> ORGANISM: Porcine epidemic diarrhea virus

<400> SEQUENCE: 9

Val Thr Arg Cys Gln Ser Thr Ile Asn Phe Arg Arg Phe Phe Ser Lys
1               5                   10                  15

Phe Asn Val Gln Ala Pro Ala Val Val Leu Gly Gly Tyr Leu Pro
            20                  25                  30

Ser Met Asn Ser Ser Ser Trp Tyr Cys Gly Thr Gly Ile Glu Thr Asp
        35                  40                  45

Ser Gly Val His Gly Ile Phe Leu Ser Tyr Ile Asp Ser Gly Gln Gly
    50                  55                  60

Phe Glu Ile Gly Ile Ser Gln Glu Pro Phe Asp Pro Ser Gly Tyr Gln
65                  70                  75                  80

Leu Tyr Leu His Lys Ala Thr Asn Gly Asn Thr Asn Ala Ile Ala Arg
                85                  90                  95

Leu Arg Ile Cys Gln Phe Pro Asp Asn Lys Thr Leu Gly Pro Thr Val
            100                 105                 110

Asn Asp Val Thr Thr Gly Arg Asn Cys Leu Phe Asn Lys Ala Ile Pro
        115                 120                 125

Ala Tyr Leu Gln Asp Gly Lys Asn Ile Val Val Gly Ile Thr Trp Asp
    130                 135                 140

Asn Asp Arg Val Thr Val Phe Ala Asp Lys Ile Tyr His Phe Tyr Leu
145                 150                 155                 160

Lys Asn Asp Trp Ser Arg Val Ala Thr Arg Cys Tyr Asn Lys Arg Ser
                165                 170                 175

Cys Ala Met Gln Tyr Val Tyr Thr Pro Thr Tyr Met Leu Asn Val
            180                 185                 190

Thr Ser Ala Gly Glu Asp Gly Ile Tyr Tyr Glu Pro Cys Thr Ala Asn
        195                 200                 205

Cys Ser Gly Tyr Ala Ala Asn Val Phe Ala Thr Asp Ser Asn Gly His
    210                 215                 220

Ile Pro Glu Gly Phe Ser Phe Asn Asn Trp Phe Leu Leu Ser Asn Asp
225                 230                 235                 240

Ser Thr Leu Leu His Gly Lys Val Ser Asn Gln Pro Leu Leu Val
                245                 250                 255

Asn Cys Leu Leu Ala Ile Pro Lys Ile Tyr Gly Leu Gly Gln Phe Phe
            260                 265                 270

Ser Phe Asn Gln Thr Met Asp Gly Val Cys Asn Gly Ala Ala Ala Gln
        275                 280                 285

Arg Ala Pro Glu Ala Leu Arg Phe Asn Ile Asn Asp Thr Ser Val Ile
    290                 295                 300

Leu Ala Glu Gly Ser Ile Val Leu His Thr Ala Leu Gly Thr Asn Leu
```

```
            305                 310                 315                 320
        Ser Phe Val Cys Ser Asn Ser Ser Asp Pro His Leu Ala Ile Phe Ala
                        325                 330                 335
        Ile Pro Leu Gly Ala Thr Glu Val Pro Tyr Tyr Cys Phe Leu Lys Val
                        340                 345                 350
        Asp Thr Tyr Asn Ser Thr Val Tyr Lys Phe Leu Ala Val Leu Pro Pro
                        355                 360                 365
        Thr Val Arg Glu Ile Val Ile Thr Lys Tyr Gly Asp Val Tyr Val Asn
                        370                 375                 380
        Gly Phe Gly Tyr Leu His Leu Gly Leu Leu Asp Ala Val Thr Ile Asn
        385                 390                 395                 400
        Phe Thr Gly His Gly Thr Asp Asp Val Ser Gly Phe Trp Thr Ile
                        405                 410                 415
        Ala Ser Thr Asn Phe Val Asp Ala Leu Ile Glu Val Gln Gly Thr Ala
                        420                 425                 430
        Ile Gln Arg Ile Leu Tyr Cys Asp Asp Pro Val Ser Gln Leu Lys Cys
                        435                 440                 445
        Ser Gln Val Ala Phe Asp Leu Asp Asp Gly Phe Tyr Pro Ile Ser Ser
                        450                 455                 460
        Arg Asn Leu Leu Ser His Glu Gln Pro Ile Ser Phe Val Thr Leu Pro
        465                 470                 475                 480
        Ser Phe Asn Asp His Ser Phe Val Asn Ile Thr Val Ser Ala Ala Phe
                        485                 490                 495
        Gly Gly His Ser Gly Ala Asn Leu Ile Ala Ser Asp Thr Thr Ile Asn
                        500                 505                 510
        Gly Phe Ser Ser Phe Cys Val Asp Thr Arg Gln Phe Thr Ile Thr Leu
                        515                 520                 525
        Phe Tyr Asn Val Thr Asn Ser Tyr Gly Tyr Val Ser Lys Ser Gln Asp
                        530                 535                 540
        Ser Asn Cys Pro Phe Thr Leu Gln Ser Val Asn Asp Tyr Leu Ser Phe
        545                 550                 555                 560
        Ser Lys Phe Cys Val Ser Thr Ser Leu Leu Ala Gly Ala Cys Thr Ile
                        565                 570                 575
        Asp Leu Phe Gly Tyr Pro Glu Phe Gly Ser Gly Val Lys Phe Thr Ser
                        580                 585                 590
        Leu Tyr Phe Gln Phe Thr Lys Gly Glu Leu Ile Thr Gly Thr Pro Lys
                        595                 600                 605
        Pro Leu Glu Gly Val Thr Asp Val Ser Phe Met Thr Leu Asp Val Cys
                        610                 615                 620
        Thr Lys Tyr Thr Ile Tyr Gly Phe Lys Gly Glu Gly Ile Ile Thr Leu
        625                 630                 635                 640
        Thr Asn Ser Ser Phe Leu Ala Gly Val Tyr Tyr Thr Ser Asp Ser Gly
                        645                 650                 655
        Gln Leu Leu Ala Phe Lys Asn Val Thr Ser Gly Ala Val Tyr Ser Val
                        660                 665                 670
        Thr Pro Cys Ser Phe Ser Glu Gln Ala Ala Tyr Val Asp Asp Asp Ile
                        675                 680                 685
        Val Gly Val Ile Ser Ser Leu Ser Asn Ser Thr Phe Asn Asn Thr Arg
                        690                 695                 700
        Glu Leu Pro Gly Phe Phe Tyr His Ser
        705                 710

<210> SEQ ID NO 10
```

<211> LENGTH: 1392
<212> TYPE: DNA
<213> ORGANISM: Artificial Sequence
<220> FEATURE:
<223> OTHER INFORMATION: Synthetic construct

<400> SEQUENCE: 10

```
atggcgaaca agcacctgag ccttagcctc ttcctcgtgc tcctgggcct ctccgcctcc      60
ctcgcctccg gcgtttcctt ccaggacagg ggcaggaagc gcgtgcccct ctcgctctac     120
gcgcccctca gggtcaccaa cgacaagccg ctcagcaagg tgctggccaa taacgcggtc     180
cccacgaaca agggcaataa ggaccagcag atcggctact ggaacgagca gatccggtgg     240
aggatgagga ggggcgagag gatcgagcag ccctccaact ggcacttcta ctacctcggc     300
acgggcccac acgcggacct gaggtaccgc accaggacgg agggcgtgtt ctgggtggcc     360
aaggagggcg ctaagacgga gcccaccaat ctcggcgtgc gcaaggcctc ggagaagccg     420
atcatcccca acttctccca gcagctgccg agcgtggtcg agatcgtgga gccaaacacc     480
ccgcccacct cgcgcgctaa ttcccgcagc aggtcccgcg caacggcaa caataggagc      540
cgctccccga gcaacaacag gggcaataac cagtcccgcg gcaacagcca gaaccggggc     600
aataaccagg gcagggcgc cagccagaac aggggcggca ataacaacaa taacaacaag      660
tcccgcaatc agagcaagaa caggaaccag tcgaatgacc gcggcggcgt gacctcgcgc     720
gacgacctcg tggcggccgt caaggacgcg ctcaagtccc tgggcatcgg cgagaacccg     780
gacaagctga gcagcagca gaagccaaag caggagaggt cggactccag cggcaagaac      840
accccgaaga agaataagtc ccgcgccacg agcaaggaga gggaccctgaa ggacatcccc     900
gagtggcgca ggatcccgaa gggcgagaac tcggtggcgg cctgcttcgg ccccgcggc      960
ggcttcaaga atttcggcga cgcggagttc gtgggagaagg gcgtggacgc ttcgggctac    1020
gctcagatcg ccagcctggc tccaaacgtg gcggccctcc tgttcggtgg caacgtggcg    1080
gtcagggagc tggcggacag ctacgagatc acctacaact acaagatgac ggtgccgaag    1140
tccgaccca atgtcgagct cctggtgagc caggtcgacg ccttcaagac cggcaacgcc    1200
aagccgcagc gcaagaagga gaagaagaac aagagggaga cgacgcagca gctcaatgag    1260
gaggccatct acgacgacgt gggcgtccca tcggacgtga cgcacgccaa cctggagtgg    1320
gacaccgctg tcgacggcgg ggatactgct gtggagatca tcaacgagat tttcgatact    1380
gggaattagt ga                                                        1392
```

<210> SEQ ID NO 11
<211> LENGTH: 462
<212> TYPE: PRT
<213> ORGANISM: Artificial Sequence
<220> FEATURE:
<223> OTHER INFORMATION: Synthetic construct

<400> SEQUENCE: 11

```
Met Ala Asn Lys His Leu Ser Leu Ser Leu Phe Leu Val Leu Leu Gly
1               5                   10                  15

Leu Ser Ala Ser Leu Ala Ser Gly Val Ser Phe Gln Asp Arg Gly Arg
            20                  25                  30

Lys Arg Val Pro Leu Ser Leu Tyr Ala Pro Leu Arg Val Thr Asn Asp
        35                  40                  45

Lys Pro Leu Ser Lys Val Leu Ala Asn Asn Ala Val Pro Thr Asn Lys
    50                  55                  60

Gly Asn Lys Asp Gln Gln Ile Gly Tyr Trp Asn Glu Gln Ile Arg Trp
```

```
            65                  70                  75                  80
        Arg Met Arg Arg Gly Glu Arg Ile Glu Gln Pro Ser Asn Trp His Phe
                         85                  90                  95

Tyr Tyr Leu Gly Thr Gly Pro His Ala Asp Leu Arg Tyr Arg Thr Arg
                        100                 105                 110

Thr Glu Gly Val Phe Trp Val Ala Lys Glu Gly Ala Lys Thr Glu Pro
                        115                 120                 125

Thr Asn Leu Gly Val Arg Lys Ala Ser Glu Lys Pro Ile Ile Pro Asn
                    130                 135                 140

Phe Ser Gln Gln Leu Pro Ser Val Val Glu Ile Val Glu Pro Asn Thr
        145                 150                 155                 160

Pro Pro Thr Ser Arg Ala Asn Ser Arg Ser Arg Ser Arg Gly Asn Gly
                        165                 170                 175

Asn Asn Arg Ser Arg Ser Pro Ser Asn Asn Arg Gly Asn Asn Gln Ser
                        180                 185                 190

Arg Gly Asn Ser Gln Asn Arg Gly Asn Gln Gly Arg Gly Ala Ser
                    195                 200                 205

Gln Asn Arg Gly Gly Asn Asn Asn Asn Lys Ser Arg Asn Gln
            210                 215                 220

Ser Lys Asn Arg Asn Gln Ser Asn Asp Arg Gly Val Thr Ser Arg
        225                 230                 235                 240

Asp Asp Leu Val Ala Ala Val Lys Asp Ala Leu Lys Ser Leu Gly Ile
                        245                 250                 255

Gly Glu Asn Pro Asp Lys Leu Lys Gln Gln Gln Lys Pro Lys Gln Glu
                        260                 265                 270

Arg Ser Asp Ser Ser Gly Lys Asn Thr Pro Lys Lys Asn Lys Ser Arg
                    275                 280                 285

Ala Thr Ser Lys Glu Arg Asp Leu Lys Asp Ile Pro Glu Trp Arg Arg
            290                 295                 300

Ile Pro Lys Gly Glu Asn Ser Val Ala Ala Cys Phe Gly Pro Arg Gly
        305                 310                 315                 320

Gly Phe Lys Asn Phe Gly Asp Ala Glu Phe Val Glu Lys Gly Val Asp
                        325                 330                 335

Ala Ser Gly Tyr Ala Gln Ile Ala Ser Leu Ala Pro Asn Val Ala Ala
                        340                 345                 350

Leu Leu Phe Gly Gly Asn Val Ala Val Arg Glu Leu Ala Asp Ser Tyr
                    355                 360                 365

Glu Ile Thr Tyr Asn Tyr Lys Met Thr Val Pro Lys Ser Asp Pro Asn
            370                 375                 380

Val Glu Leu Leu Val Ser Gln Val Asp Ala Phe Lys Thr Gly Asn Ala
        385                 390                 395                 400

Lys Pro Gln Arg Lys Lys Glu Lys Lys Asn Lys Arg Glu Thr Thr Gln
                        405                 410                 415

Gln Leu Asn Glu Glu Ala Ile Tyr Asp Asp Val Gly Val Pro Ser Asp
                        420                 425                 430

Val Thr His Ala Asn Leu Glu Trp Asp Thr Ala Val Asp Gly Gly Asp
                    435                 440                 445

Thr Ala Val Glu Ile Ile Asn Glu Ile Phe Asp Thr Gly Asn
            450                 455                 460

<210> SEQ ID NO 12
<211> LENGTH: 558
<212> TYPE: DNA
<213> ORGANISM: Artificial Sequence
```

<220> FEATURE:
<223> OTHER INFORMATION: Synthetic construct

<400> SEQUENCE: 12

```
atggcgaaca agcacctgag ccttagcctc ttcctcgtgc tcctgggcct ctccgcctcc      60
ctcgcctccg gctcccacga gcagccgatc agcttcgtca cgctcccctc cttcaacgac     120
cacagcttcg tcaacatcac cgtgtccgct tccttcggtg gccactcggg cgctaacctg     180
atcgccagcg acaccacgat caacggcttc tccagcttct gcgtggacac gaggcagttc     240
accatctccc tcttctacaa cgtcacgaac agctacggct acgtgtccaa gagccaggac     300
tccaactgcc cgttcaccct ccagagcgtc aacgactacc tgtccttcag caagttctgc     360
gtgtccacga gcctgctggc ttcggcctgc accatcgacc tgttcggcta ccccgagttc     420
ggctccggcg tcaagttcac gagcctctac ttccagttca ccaagggcga gctcatcacg     480
ggcacccccca agccactgga gggcgtcacg gacgtgttct accctcta ccacagcacc     540
ccacagcgcc cctgatag                                                   558
```

<210> SEQ ID NO 13
<211> LENGTH: 36
<212> TYPE: DNA
<213> ORGANISM: Artificial Sequence
<220> FEATURE:
<223> OTHER INFORMATION: DC3 nucletotide sequence

<400> SEQUENCE: 13

```
ttctacccct cctaccacag caccccacag cgcccc                                36
```

<210> SEQ ID NO 14
<211> LENGTH: 309
<212> TYPE: DNA
<213> ORGANISM: Escherichia coli

<400> SEQUENCE: 14

```
gccccgcagt ccatcaccga gctctgctcc gagtaccaca cacccagat ctacaccatc       60
aacgacaaga tcctctccta caccgagagc atggccggca agcgcgagat ggtgatcatc     120
accttcaagt ccggcgccac cttccaggtg gaggtgccgg gctcccagca catcgactcc     180
cagaagaagg ccatcgagcg catgaaggac accctccgca tcacctacct caccgagacc     240
aagatcgaca gctctgcgt gtggaacaac aagacccccga actccatcgc cgccatcagc     300
atggagaac                                                             309
```

<210> SEQ ID NO 15
<211> LENGTH: 103
<212> TYPE: PRT
<213> ORGANISM: Escherichia coli

<400> SEQUENCE: 15

```
Ala Pro Gln Ser Ile Thr Glu Leu Cys Ser Glu Tyr His Asn Thr Gln
  1               5                  10                  15
Ile Tyr Thr Ile Asn Asp Lys Ile Leu Ser Tyr Thr Glu Ser Met Ala
                 20                  25                  30
Gly Lys Arg Glu Met Val Ile Ile Thr Phe Lys Ser Gly Ala Thr Phe
             35                  40                  45
Gln Val Glu Val Pro Gly Ser Gln His Ile Asp Ser Gln Lys Lys Ala
         50                  55                  60
Ile Glu Arg Met Lys Asp Thr Leu Arg Ile Thr Tyr Leu Thr Glu Thr
 65                  70                  75                  80
```

Lys Ile Asp Lys Leu Cys Val Trp Asn Asn Lys Thr Pro Asn Ser Ile
            85                  90                  95

Ala Ala Ile Ser Met Glu Asn
            100

<210> SEQ ID NO 16
<211> LENGTH: 3002
<212> TYPE: DNA
<213> ORGANISM: Zea mays

<400> SEQUENCE: 16

| | | | | | |
|---|---|---|---|---|---|
| cggtatgaat | ttggaaacaa | attcagtact | tttaaaaaaa | tttgttgtag | ggagcaaata | 60 |
| atacataaaa | taatttatgc | attattttat | tttttatttg | taataatatg | cttgaaacga | 120 |
| taattcagta | tgcatgttgt | gccagtgtac | tacacgggcg | gggggagggg | attgagtggg | 180 |
| ccagcgcggt | gcgtagggta | gatgggctga | aattgataac | tcaagtccga | ctaggttctc | 240 |
| tttttatttc | ccttccttttt | ctattttcct | ttcttttaat | tttcatgctt | tcaaactaaa | 300 |
| ttcaaattcg | agttttgaat | ttcagcttct | aaattgtaca | ctaaaattat | atgataaggt | 360 |
| aaccccctact | attacttttta | attttttttat | tctaccccat | attgtttact | tagggagaa | 420 |
| taattgactt | aatcacattc | ttcctaggtt | tcaattctca | atctttcaaa | tccacatttt | 480 |
| tagatttcta | ttttgaattt | aaataccagt | ttggatttag | agttcaattt | caaaatacac | 540 |
| aaccaaaata | ccagcatgaa | tgcaaatata | ttttatgttt | atgtatttac | ttttcttttta | 600 |
| tactttgctc | aaaatagtta | ttttcatgta | tgaaactcaa | taagcaagga | actcacgtta | 660 |
| ttatataacc | taataggaat | aatttaggta | acataaattta | tcatcctctt | gatttaaaag | 720 |
| agatatgcct | ccagaataag | acacatacta | aaaataactc | taatattgaa | taactaaagt | 780 |
| cgtacaaatc | tctactatta | ttcctataaa | ataataaaga | actagctaca | acttctttaa | 840 |
| ggcattattc | agggtttaca | gcttgagagg | catgaaccca | tcctgtatac | tcctggactt | 900 |
| ggaagacaaa | atgtcaacca | aagtgaaagg | ttttcttatg | gttgctgcta | agagatagat | 960 |
| tgaacactag | atctctccta | agacgtcagg | gcatgcgttt | agactcctac | acatgcgaaa | 1020 |
| actgcatctt | acagttggaa | gaaactatat | ctcaccactt | cctgcggtgt | aactttgccc | 1080 |
| aaagatgttg | gctcactgtt | ggaatcactc | cgccccgaac | tttggatcta | acgcttgcag | 1140 |
| tgctacatat | tagagcaaga | ctaacaatgc | cgtggagaat | ggaaggtatt | ataaccatgt | 1200 |
| catggtgcat | atggaaatgt | cgaaataact | ggatattcga | aaacataccg | ccaacggtgg | 1260 |
| cggcctgcaa | ggaaatgttc | aagactgaaa | tgaactacat | ctgctaccaa | gttaagctcg | 1320 |
| agacaggagc | taaaagtaga | aactggatac | aacactttgt | aacatagtga | cactccccctt | 1380 |
| ttcctttctt | ttaccttaga | actatacata | caatccacat | tcaataaaaa | tttgtaggta | 1440 |
| cgccatacac | actaccggaa | tccggctctt | tgccgagtgt | gaggcgcttt | gtcgagtgct | 1500 |
| ttttgtccag | cactcggcaa | aaaagtcttt | gccatgtgcc | gcactcggca | aagtcctgct | 1560 |
| ctcggtaacg | accgcgttta | ccgagagcag | gactctcgac | acagaaatac | actcgacaaa | 1620 |
| gaaatctttg | ccgagagcca | acactcggc | gaacggcagc | gctcggcaaa | gggtcgtcag | 1680 |
| ccgccgtcta | aagctgacgg | tcgttatctt | tgtcgagtgc | ccctcgtcc | gacactcagt | 1740 |
| agagcaagct | tgccgagtgc | catccttgga | cactcgataa | agtatatttt | attttttttt | 1800 |
| attttgccaa | ccaaacttttt | tgtggtatgt | tcctacacta | tgtagatcta | catgtaccat | 1860 |
| tttggcacaa | ttacaaaaat | gttttctata | actattagat | ttagttcgtt | tatttgaatt | 1920 |

-continued

| | |
|---|---|
| tcttcggaaa attcacatat gaactgcaag tcactcgaaa catgaaaaac cgtgcatgca | 1980 |
| aaataaatga tatgcatgtt atctagcaca agttacgacc gaattcagaa gcagaccaga | 2040 |
| atcttcaagc accatgctca ctaaacatga ccgtgaactt gttatccagt tgtttaaaaa | 2100 |
| ttgtataaaa cacaaataaa gtcagaaatt aatgaaactt gtccacatgt catgatatca | 2160 |
| tatatagagg ttgtgataaa aatttgataa tgtttcggta agttgtgac gtactatgtg | 2220 |
| tagaaaccta agtgacctac acataaaatc atagagtttc aatgtagttc actcgacaaa | 2280 |
| gactttgtca agtgtccgat aaaaagtatt cagcaaagaa gccgttgtcg atttactgtt | 2340 |
| cgtcgagatc tctttgccga gtgtcacact aggcaaagtc tttacggagt gttttttcagg | 2400 |
| ctttgacact cggcaaagcg ctcgattcca gtagtgacag taatttgcat caaaaatagc | 2460 |
| cgagagattt aaaatgagtc aactaataga ccaactaatt attagctatt agtcgttagc | 2520 |
| ttctttaatc taagctaaaa ccaactaata gcttatttgt tgaattacaa ttagctcaac | 2580 |
| ggaattctct gttttttcta taaaaaaaag ggaaactgcc cctcatttac agcaaactgt | 2640 |
| ccgctgcctg tcgtccagat acaatgaacg tacctagtag gaactctttt acacgctcgg | 2700 |
| tcgctcgccg cggatcggag tcccaggaac acgacaccac tgtggaacac gacaaagtct | 2760 |
| gctcagaggc ggccacaccc tggcgtgcac cgagccggag cccggataag cacggtaagg | 2820 |
| agagtacggc gggacgtggc gacccgtgtg tctgctgcca cgcagccttc ctccacgtag | 2880 |
| ccgcgcggcc gcgccacgta ccagggcccg gcgctggtat aaatgcgcgc cacctccgct | 2940 |
| ttagttctgc atacagccaa cccaacacac acccgagcat atcacagtga cagacactac | 3000 |
| ac | 3002 |

<210> SEQ ID NO 17
<211> LENGTH: 2520
<212> TYPE: DNA
<213> ORGANISM: Zea mays

<400> SEQUENCE: 17

| | |
|---|---|
| gcgctccctg acgctgtctt gggagagctg caagatgaga cactccatcc cgcgcagccc | 60 |
| tgtcgtggcg tcctcctgga tggacacctg catcgctgtc gccctccacc aactcacctg | 120 |
| aacgaagaat agaataaaaa atggagggag ctgagggggc agtggttgcg ctgtagggag | 180 |
| gagagagacc gcgtcattat aagactatct gcaaccgtta cctctaaatt tttccctcta | 240 |
| tatcattttt tccccatatt ttccccccta ttttttcatc tcccgcaacg gtttctccta | 300 |
| aatactcccc ctatatctca ctaccactat aaaatattat ttttatacc aactatcaat | 360 |
| tttttatcta ctaacaatta ctcgtggacc cacagcacag tgtttaggag atgaacagtg | 420 |
| acacgctata tctgggggga gagagaaaga ggccggcgcg tagggggcgc cgtaggggca | 480 |
| ctgctgcggc tgtagagtac cccctacacg ccgcatgcaa gggaagggg ctgtcagggg | 540 |
| ggcaatgttg cgcatagcct aaagagcgga tgaagcggct tgcaatttgc acgctggatt | 600 |
| cataaatagt gcatattact aaaaaaaagg gtggggatag gtatagagag tctattagag | 660 |
| ttgatctaag acccggttta tttcagatta taatctgtcc ggattatata atccagcgca | 720 |
| aataatacag taggtaaaca aacaactaga ttatgggttc agattatata atctaaaccc | 780 |
| cagattatga taatctcata atctcctcaa gagtagctta ttggagatta ttttggcaaa | 840 |
| agacccacta cccatggtta tgtaaataga aattataata tatatcatct tttttctcac | 900 |
| cttaaataaa caaataaggg tattgttgtc tttatgaata atctacattt gtataatcta | 960 |
| aactaccaaa caactacatc tagattataa tctggattat ataatttaaa ttataatcta | 1020 |

```
gattatataa tttataagct gaaacaaccc ggccctaaag cactatcgta tcacctatct    1080
gaaataagtc acgggtttcg aacgtccact tgcgtcgcac ggaattgcat gtttcttgtt    1140
ggaagcatat tcacgcaatc tccacacata aaggtttatg tataaactta catttagctc    1200
agtttaatta cagtcttatt tggatgcata tgtatggttc tcaatccata taagttagag    1260
taaaaaataa gtttaaattt tatcttaatt cactccaaca tatatggatt gagtacaata    1320
ctcatgtgca tccaaacaaa ctacttatat tgaggtgaat ttggatagaa attaaactaa    1380
cttacacact aagccaatct ttactatatt aaagcaccag tttcaacgat cgtcccgcgt    1440
caatattatt aaaaaactcc tacatttctt tataatcaac ccgcactctt ataatctctt    1500
ctctactact ataataagag agtttatgta caaaataagg tgaaattatg tataagtgtt    1560
ctggatattg gttgttggct ccatattcac acaacctaat caatagaaaa catatgtttt    1620
attaaaacaa aatttatcat atatcatata tatatatata aaccgtagca atgcacgggc    1680
atataactag tgcaacttaa tacatgtgtg tattaagatg aataagaggg tatccaaata    1740
aaaaacttgt tcgcttacgt ctggatcgaa aggggttgga aacgattaaa tctcttccta    1800
gtcaaaattg aatagaagga gatttaatct ctcccaatcc ccttcgatca tccaggtgca    1860
accgtataag tcctaaagtg gtgaggaaca cgaaacaacc atgcattggc atgtaaagct    1920
ccaagaattt gttgtatcct taacaactca cagaacatca accaaaattg cacgtcaagg    1980
gtattgggta agaaacaatc aaacaaatcc tctctgtgtg caaagaaaca cggtgagtca    2040
tgccgagatc atactcatct gatatacatg cttacagctc acaagacatt acaaacaact    2100
catattgcat tacaaagatc gtttcatgaa aaataaaata ggccggacag gacaaaaatc    2160
cttgacgtgt aaagtaaatt tacaacaaaa aaaagccat atgtcaagct aaatctaatt    2220
cgttttacgt agatcaacaa cctgtagaag gcaacaaaac tgagccacgc agaagtacag    2280
aatgattcca gatgaaccat cgacgtgcta cgtaaagaga gtgacgagtc atatacatt    2340 ggcaagaaac catgaagctg cctacagccg tctcggtggc ataagaacac aagaaattgt    2400
gttaattaat caaagctata aataacgctc gcatgcctgt gcacttctcc atcaccacca    2460
ctgggtcttc agaccattag ctttatctac tccagagcgc agaagaaccc gatcgacacc    2520
```

<210> SEQ ID NO 18
<211> LENGTH: 6510
<212> TYPE: DNA
<213> ORGANISM: Artificial Sequence
<220> FEATURE:
<223> OTHER INFORMATION: Synthetic construct

<400> SEQUENCE: 18

```
ggcgcgccgg tatgaatttg gaaacaaatt cagtactttt aaaaaaattt gttgtaggga     60
gcaaataata cataaaataa tttatgcatt attttatttt ttatttgtaa taatatgctt    120
gaaacgataa ttcagtatgc atgttgtgcc agtgtactac acgggcgggg ggaggggatt    180
gagtgggcca gcgcggtgcg tagggtagat gggctgaaat tgataactca agtccgacta    240
ggttctcttt ttatttccct tccttttcta ttttcctttc ttttaatttt catgctttca    300
aactaaattc aaattcgagt tttgaatttc agcttctaaa ttgtacacta aaattatatg    360
ataaggtaac ccctactatt acttttaatt tttttattct accccatatt gtttacttag    420
gggagaataa ttgacttaat cacattcttc ctaggtttca attctcaatc tttcaaatcc    480
acatttttag atttctattt tgaatttaaa taccagtttg gatttagagt tcaatttcaa    540
```

```
aatacacaac caaaatacca gcatgaatgc aaatatattt tatgtttatg tatttacttt    600
tcttttatac tttgctcaaa atagttattt tcatgtatga aactcaataa gcaaggaact    660
cacgttatta tataacctaa taggaataat ttaggtaaca taatttatca tcctcttgat    720
ttaaaagaga tatgcctcca gaataagaca catactaaaa ataactctaa tattgaataa    780
ctaaagtcgt acaaatctct actattattc ctataaaata ataaagaact agctacaact    840
tctttaaggc attattcagg gtttacagct tgagaggcat gaacccatcc tgtatactcc    900
tggacttgga agacaaaatg tcaaccaaag tgaaaggttt tcttatggtt gctgctaaga    960
gatagattga acactagatc tctcctaaga cgtcagggca tgcgtttaga ctcctacaca   1020
tgcgaaaact gcatcttaca gttggaagaa actatatctc accacttcct gcggtgtaac   1080
tttgcccaaa gatgttggct cactgttgga atcactccgc cccgaacttt ggatctaacg   1140
cttgcagtgc tacatattag agcaagacta acaatgccgt ggagaatgga aggtattata   1200
accatgtcat ggtgcatatg gaatgtcga aataactgga tattcgaaaa cataccgcca   1260
acggtggcgg cctgcaagga aatgttcaag actgaaatga actacatctg ctaccaagtt   1320
aagctcgaga caggagctaa aagtagaaac tggatacaac actttgtaac atagtgacac   1380
tccccttttc ctttcttta ccttagaact atacatacaa tccacattca ataaaaattt   1440
gtaggtacgc catacacact accggaatcc ggctctttgc cgagtgtgag gcgctttgtc   1500
gagtgctttt tgtccagcac tcggcaaaaa agtctttgcc atgtgccgca ctcggcaaag   1560
tcctgctctc ggtaacgacc gcgtttaccg agagcaggac tctcgacaca gaaatacact   1620
cgacaaagaa atctttgccg agagccaaac actcggcgaa cggcagcgct cggcaaaggg   1680
tcgtcagccg ccgtctaaag ctgacggtcg ttatctttgt cgagtgcccc ctcgtccgac   1740
actcagtaga gcacgcgccg gtatgaattt ggaaacaaat tcagtacttt taaaaaaatt   1800
tgttgtaggg agcaaataat acataaaata atttatgcat tatttattt tttatttgta   1860 ataatatgct tgaaacgata attcagtatg catgttgtgc cagtgtacta cacgggcggg   1920
gggaggggat tgagtgggcc agcgcggtgc gtagggtaga tgggctgaaa ttgataactc   1980
aagtccgact aggttctctt tttatttccc ttccttttct attttccttt cttttaattt   2040
tcatgctttc aaactaaatt caaattcgag ttttgaattt cagcttctaa attgtacact   2100
aaaattatat gataaggtaa cccctactat tacttttaat tttttttattc taccccatat   2160 tgtttactta ggggagaata attgacttaa tcacattctt cctaggtttc aattctcaat   2220
ctttcaaatc cacattttta gatttctatt ttgaatttaa ataccagttt ggatttagag   2280
ttcaatttca aaatacacaa ccaaaatacc agcatgaatg caaatatatt ttatgtttat   2340
gtatttactt ttcttttata ctttgctcaa aatagttatt ttcatgtatg aaactcaata   2400
agcaaggaac tcacgttatt atataaccta ataggaataa tttaggtaac ataatttatc   2460
atcctcttga tttaaaagag atatgcctcc agaataagac acatactaaa aataactcta   2520
atattgaata actaaagtcg tacaaatctc tactattatt cctataaaat aataaagaac   2580
tagctacaac ttctttaagg cattattcag ggtttacagc ttgagaggca tgaacccatc   2640
ctgtatactc ctggacttgg aagacaaaat gtcaaccaaa gtgaaaggtt tcttatggt   2700 tgctgctaag agatagattg aacactagat ctctcctaag acgtcagggc atgcgtttag   2760
actcctacac atgcgaaaac tgcatcttac agttggaaga actatatct caccacttcc   2820 tgcggtgtaa ctttgcccaa agatgttggc tcactgttgg aatcactccg cccgaactt   2880 tggatctaac gcttgcagtg ctacatatta gagcaagact aacaatgccg tggagaatgg   2940
```

```
aaggtattat aaccatgtca tggtgcatat ggaaatgtcg aaataactgg atattcgaaa    3000
acataccgcc aacggtggcg gcctgcaagg aaatgttcaa gactgaaatg aactacatct    3060
gctaccaagt taagctcgag acaggagcta aaagtagaaa ctggatacaa cactttgtaa    3120
catagtgaca ctccccttt ccttctttt accttagaac tatacataca atccacattc    3180
aataaaaatt tgtaggtacg ccatacacac taccggaatc cggctctttg ccgagtgtga    3240
ggcgctttgt cgagtgcttt ttgtccagca ctcggcaaaa aagtctttgc catgtgccgc    3300
actcggcaaa gtcctgctct cggtaacgac cgcgtttacc gagagcagga ctctcgacac    3360
agaaatacac tcgacaaaga aatctttgcc gagagccaaa cactcggcga acggcagcgc    3420
tcggcaaagg gtcgtcagcc gccgtctaaa gctgacggtc gttatctttg tcgagtgccc    3480
cctcgtccga cactcagtag agcacgcgcc ggtatgaatt tggaaacaaa ttcagtactt    3540
ttaaaaaaat ttgttgtagg gagcaaataa tacataaaat aatttatgca ttattttatt    3600 tttatttgt aataatatgc ttgaaacgat aattcagtat gcatgttgtg ccagtgtact    3660
acacgggcgg ggggagggga ttgagtgggc cagcgcggtg cgtagggtag atgggctgaa    3720
attgataact caagtccgac taggttctct tttatttcc cttccttttc tattttcctt    3780
tcttttaatt ttcatgcttt caaactaaat tcaaattcga gttttgaatt tcagcttcta    3840
aattgtacac taaaattata tgataaggta accctacta ttacttttaa ttttttatt    3900 ctaccccata ttgtttactt aggggagaat aattgactta atcacattct tcctaggttt    3960
caattctcaa tctttcaaat ccacatttt agatttctat tttgaattta ataccagtt    4020 tggatttaga gttcaatttc aaaatacaca accaaaatac cagcatgaat gcaaatatat    4080
tttatgttta tgtatttact tttctttat actttgctca aaatagttat tttcatgtat    4140
gaaactcaat aagcaaggaa ctcacgttat tatataacct aataggaata atttaggtaa    4200
cataatttat catcctcttg atttaaaaga gatatgcctc cagaataaga cacatactaa    4260
aaataactct aatattgaat aactaaagtc gtacaaatct ctactattat tcctataaaa    4320
taataaagaa ctagctacaa cttctttaag gcattattca gggtttacag cttgagaggc    4380
atgaacccat cctgtatact cctggacttg gaagacaaaa tgtcaaccaa agtgaaaggt    4440
tttcttatgg ttgctgctaa gagatagatt gaacactaga tctctcctaa gacgtcaggg    4500
catgcgttta gactcctaca catgcgaaaa ctgcatctta cagttggaag aaactatatc    4560
tcaccacttc ctgcggtgta actttgccca aagatgttgg ctcactgttg gaatcactcc    4620 gcccgaact ttggatctaa cgcttgcagt gctacatatt agagcaagac taacaatgcc    4680
gtggagaatg gaaggtatta taaccatgtc atggtgcata tggaaatgtc gaaataactg    4740
gatattcgaa aacataccgc caacggtggc ggcctgcaag gaaatgttca agactgaaat    4800
gaactacatc tgctaccaag ttaagctcga gacaggagct aaaagtagaa actggataca    4860
acactttgta acatagtgac actccccttt tcctttcttt taccttagaa ctatacatac    4920
aatccacatt caataaaaat ttgtaggtac gccatacaca ctaccggaat ccggctcttt    4980
gccgagtgtg aggcgctttg tcgagtgctt tttgtccagc actcggcaaa aaagtctttg    5040
ccatgtgccg cactcggcaa agtcctgctc tcggtaacga ccgcgtttac cgagagcagg    5100
actctcgaca cagaaataca ctcgacaaag aaatctttgc cgagagccaa acactcggcg    5160
aacggcagcg ctcggcaaag gtcgtcagc cgccgtctaa agctgacggt cgttatcttt    5220
gtcgagtgcc cctcgtccg acactcagta gagcaagctt gccgagtgcc atccttggac    5280
```

```
actcgataaa gtatatttta tttttttta ttttgccaac caaacttttt gtggtatgtt      5340
cctacactat gtagatctac atgtaccatt ttggcacaat tacaaaaatg ttttctataa      5400
ctattagatt tagttcgttt atttgaattt cttcggaaaa ttcacatatg aactgcaagt      5460
cactcgaaac atgaaaaacc gtgcatgcaa aataaatgat atgcatgtta tctagcacaa      5520
gttacgaccg aattcagaag cagaccagaa tcttcaagca ccatgctcac taaacatgac      5580
cgtgaacttg ttatccagtt gtttaaaaat tgtataaaac acaaataaag tcagaaatta      5640
atgaaacttg tccacatgtc atgatatcat atatagaggt tgtgataaaa atttgataat      5700
gtttcggtaa agttgtgacg tactatgtgt agaaacctaa gtgacctaca cataaaatca      5760
tagagtttca atgtagttca ctcgacaaag actttgtcaa gtgtccgata aaaagtattc      5820
agcaaagaag ccgttgtcga tttactgttc gtcgagatct ctttgccgag tgtcacacta      5880
ggcaaagtct ttacggagtg tttttcaggc tttgacactc ggcaaagcgc tcgattccag      5940
tagtgacagt aatttgcatc aaaaatagcc gagagattta aaatgagtca actaatagac      6000
caactaatta ttagctatta gtcgttagct tctttaatct aagctaaaac caactaatag      6060
cttatttgtt gaattacaat tagctcaacg gaattctctg ttttttctat aaaaaaaagg      6120
gaaactgccc ctcatttaca gcaaactgtc cgctgcctgt cgtccagata caatgaacgt      6180
acctagtagg aactctttta cacgctcggt cgctcgccgc ggatcggagt cccaggaaca      6240
cgacaccact gtggaacacg acaaagtctg ctcagaggcg gccacaccct ggcgtgcacc      6300
gagccggagc ccggataagc acggtaagga gagtacggcg ggacgtggcg acccgtgtgt      6360
ctgctgccac gcagccttcc tccacgtagc gcgcggccg cgccacgtac cagggcccgg      6420
cgctggtata aatgcgcgcc acctccgctt tagttctgca tacagccaac ccaacacaca      6480
cccgagcata tcacagtgac agacactaca                                      6510
```

<210> SEQ ID NO 19
<211> LENGTH: 12
<212> TYPE: DNA
<213> ORGANISM: Artificial Sequence
<220> FEATURE:
<223> OTHER INFORMATION: Endoplasmic reticulum signal sequence

<400> SEQUENCE: 19

```
aaggacgagc tc                                                           12
```

<210> SEQ ID NO 20
<211> LENGTH: 28038
<212> TYPE: DNA
<213> ORGANISM: Porcine epidemic diarrhea virus

<400> SEQUENCE: 20

```
acttaaaaag attttctatc tacggatagt tagctctttt tctagactct tgtctactca        60
attcaactaa acgaaatttt gtccttccgg ccgcatgtcc atgctgctgg aagctgacgt       120
ggaatttcat taggtttgct taagtagcca tcgcaagtgc tgtgctgtcc tctagttcct       180
ggttggcgtt ccgtcgcctt ctacatacta gacaaacagc cttcctccgg ttccgtctgg       240
gggttgtgtg gataactagt tccgtctagt ttgaaactag taactgtcgg ctatggctag       300
caaccatgtt acattggctt tgccaatga tgcagaaatt tcagcttttg cttttgcac        360 tgctagtgaa gccgtctcat actattctga ggccgccgct agtggattta tgcaatgccg       420
tttcgtgtcc ttcgatctcg ctgacactgt tgagggattc cttcccgaag actatgtcat       480
ggtggtggtc ggcactacca agcttagtgc gtatgtggac acttttggta gccgccccaa       540
```

```
aaacatttgt ggttggctgt tattttctaa ctgtaattac ttcctcgaag agttagagct    600 tactttggt cgtcgtggtg gtaacatcgt gccagttgac caatacatgt gtggcgctga     660
cggtaaacct gttcttcagg aatccgaatg ggagtataca gatttctttg ctgactccga    720
agacggtcaa ctcaacattg ctggtatcac ttatgtgaag gcctggattg tagagcgatc    780
ggatgtctct tatgcgagtc agaatttaac atctattaag tctattactt actgttcaac    840
ctatgagcat acttttcctg atggtactgc catgaaggtt gcacgtactc caaagattaa    900
gaagactgtt gtcttgtctg agccacttgc tactatctac agggaaattg gttctccttt    960
tgtggataat gggagcgatg ctcgttctat cattaagaga ccagtgttcc tccacgcttt   1020
tgttaagtgt aagtgtggta gttatcattg gactgttggt gattggactt cctatgtctc   1080
cacttgctgt ggctttaagt gtaagccagt ccttgtggct tcatgctctg ctacgcctgg   1140
ttctgttgtg gttacgcgcg ctggtgctgg cactggtgtt aagtattaca caacatgtt    1200 cctgcgccat gtggcagaca ttgatgggtt ggcattctgg cgaattctca aggtgcagtc   1260
caaagacgac ctcgcttgct ctggtaaatt ccttgaacac catgaggaag gtttcacaga   1320
tccttgctac tttttgaatg actcgagcat tgctactaag ctcaagtttg acatccttag   1380
tggcaagttt tctgatgaag tcaaacaagc tatctttgct ggtcatgttg ttgttggcag   1440
cgcgctcgtt gacattgttg acgatgcact gggacagcct tggttatac gtaagcttgg    1500 tgaccttgca agtgcagctt gggagcagct taaggctgtc gttagaggcc ttaacctcct   1560
gtctgatgag gtcgtgctct ttggcaaaag acttagctgt gccactctta gtatcgttaa   1620
cggtgttttt gagttcatcg ccgaagtgcc tgagaagttg gctgcggctg ttacagtttt   1680
tgtcaacttc ttgaatgagc ttttgagtc tgcctgtgac tgcttaaagg tcggaggtaa    1740
aacctttaac aaggttggct cttatgttct ttttgacaac gcattggtta agcttgtcaa   1800
ggcaaaagtt cgcggcccac gacaggcagg tgtttgtgaa gttcgttaca caagccttgt   1860
tattgggagt actaccaagg tggtttccaa gcgcgttgaa aatgccaatg tgaatctcgt   1920
cgtcgttgac gaggatgtga ccctcaacac cactggtcgt acagttgttg ttgacggact   1980
tgcattcttc gagagtgacg ggttttacag acatcttgct gatgctgacg ttgtcattga   2040
acatcctgtt tataagtctg cttgtgagct caagccagtt tttgagtgtg acccaatacc   2100
tgattttcct atgcctgtgg ccgctagtgt tgcagagctt tgtgtgcaaa ctgatctgtt   2160
gcttaaaaat tacaacactc cttataaaac ttacagctgc gttgtgagag gtgataagtg   2220
ttgtatcact tgcaccttac atttcacagc accaagttat atggaggctg ctgctaattt   2280
tgtagacctc tgtaccaaga acattggtac tgctggtttt catgagtttt acattacggc   2340
ccatgaacaa caggatctgc aagggttcgt aaccacttgt tgcacgatgt caggttttga   2400
gtgttttatg cctataatcc cacagtgtcc agcagtgctt gaagagattg atggtggtag   2460
catctggcgg tcttttatca ctggtcttaa tacaatgtgg gattttttgca agcatcttaa   2520 agtcagcttt ggactagatg gcattgttgt cactgtagca cgcaaattta aacgacttgg   2580
tgctctcttg gcagaaatgt ataacactta cctttcaact gtggtggaaa acttggtact   2640
ggccggtgtt agcttcaagt attatgccac cagtgtccca aaaattgttt gggctgttg    2700 ttttcacagt gttaaaagtg ttcttgcaag tgccttccag attcctgtcc aggcaggcgt   2760
tgagaagttt aaagtcttcc ttaactgtgt tcaccctgtt gtaccacgtg tcattgaaac   2820 ttctttgtg gaattagaag agacgacatt taaaccacca gcactcaatg gtagtattgc   2880
```

```
tattgttgat ggctttgctt tctattatga tggaacacta tactatccca ccgatggtaa      2940
tagcgttgtt cctatctgct ttaagaagaa aggtggtggt gatgtcaaat tctctgatga      3000
agtctctgtt aaaaccattg acccagttta taaggtctcc cttgaatttg agttcgagtc      3060
tgagactatt atggctgtgc ttaataaggc tgttggtaat tgtatcaagg ttacaggtgg      3120
ttgggacgat gttgttgagt atatcaatgt tgccattgag gttcttaaag atcacatcga      3180
tgtgcctaag tactacatct atgatgagga aggtggcacc gatcctaatc tgcccgtaat      3240
ggtttctcag tggccgttga atgatgacac gatctcacag gatctgcttg atgttgaagt      3300
tgttactgat gcgccagttg atttcgaggg tgatgaagta gactcctctg accctgataa      3360
ggtggcagac gtggctaact ctgagcctga ggatgacggt cttaatgtag ctcctgaaac      3420
aaatgtagag tctgaagttg aggaagttgc cgcaaccttg tcctttatta aagatacacc      3480
ttccacagtt actaaggatc ctttgctttt tgactttgca agctatggag gacttaaggt      3540
tttaagacaa tctcataaca actgctgggt tacttctacc ttggtgcagc tacaattgct      3600
tggcatcgtt gatgaccctg caatggagct ttttagtgct ggtagagttg gtccaatggt      3660
tcgcaaatgc tatgagtcac aaaaggctat cttgggatct ttgggtgatg tgtcggcttg      3720
cctagagtct ctgactaagg acctacacac acttaagatt acctgttctg tagtctgtgg      3780
ttgtggtact ggtgaacgta tctatgatgg ttgtgctttt cgtatgacgc caactttgga      3840
accgttccca tatggtgctt gtgctcagtg tgctcaagtt ttgatgcaca cttttaaaag      3900
tattgttggc accggcatct tttgtcgaga tactactgct ctctccttgg attctttggt      3960
tgtaaaacct ctttgtgcgg ctgcttttat aggcaaggat agtggtcatt atgtcactaa      4020 ctttatgat gctgctatgg ctattgatgg ttatggtcgt catcagataa agtatgacac      4080
actgaacact atttgtgtta aagacgttaa ttggacagca cctttttgtcc cagacgttga      4140 gcctgtattg gagcctgttg tcaaaccttt ctattcttat aagaatgttg atttttacca      4200
aggagatttt agtgaccttg ttaaacttcc atgtgatttt gttgttaatg ctgcaaatga      4260
gaatttgtct cacggtggcg gcatagcaaa ggccattgat gtttatacca agggcatgtt      4320
gcagaagtgc tcgaatgatt acattaaagc acacggtccc attaaagttg acgtggtgt       4380 catgttggag gcattaggtc ttaaggtctt taatgttgtt ggtccacgta agggtaagca      4440
tgcacctgag cttcttgtta aggcttataa gtccgttttt gctaattcag gtgttgctct      4500
tacacctttg attagtgttg aatttttag tgttcctttg gaagaatctt tatctgcttt        4560
tcttgcatgt gttggtgatc gccactgtaa gtgcttttgt tatagtgaca aagagcgcga      4620
ggcgatcatt aattacatgg atggcttggt agatgctatt ttcaaagatg cacttgttga      4680
tactactcct gtccaggaag atgttcaaca agttcacaa aaaccagttt tgcctaattt       4740
tgaacctttc aggattgaag gtgctcatgc tttctatgag tgcaaccctg aaggtttgat       4800
gtcattaggt gctgacaagc tggtgttgtt tacaaattcc aatttggatt tttgtagcgt      4860
tggtaagtgt cttaacaatg tgactggcgg tgcattgctt gaagccataa atgtattta       4920 aaagagtaac aaaacagtgc ctgctggcaa ctgtgttact tttgagtgtg cagatatgat      4980
ttctattact atggtagtat tgccatctga cggtgatgct aattatgaca aaaattatgc      5040
acgcgccgtc gtcaaggtat ctaagcttaa aggcaagtta ttgcttgctg ttggtgatgc      5100
catgttgtat tccaagttgt cccacctcag cgtgttaggt ttcgtatcca cacctgatga      5160
tgtggagcgt ttctacgcaa ataagagtgt ggttattaaa gttactgagg atacacgtag      5220
tgttaagact gttaaagtag aatccactgt tacttatgga caacaaattg gaccttgtct      5280
```

```
tgttaatgac accgttgtca cagacaacaa acctgttgtt gctgatgttg tagctaaggt    5340
tgtaccaagt gctaattggg attcacatta tggttttgat aaggctggtg agttccacat    5400
gctagaccat actgggtttg cctttcctag tgaagttgtt aacggtaggc gtgtgcttaa    5460
aaccacagat aataactgtt gggttaatgt tacatgttta caattacagt ttgctagatt    5520
taggttcaag tcagcaggtc tacaggctat gtgggagtcc tattgtactg gtgatgttgc    5580
tatgtttgtg cattggttgt actggcttac tggtgttgac aaaggtcagc ctagtgattc    5640
agaaaatgca cttaacatgt tgtctaagta cattgttcct gctggttctg tcactattga    5700
acgtgtcacg catgacggtt gttgttgtag taagcgtgtt gtcactgcac cagttgtgaa    5760
tgctagcgtg ttgaagcttg gcgtcgagga tggtctttgt ccacatggtc ttaactacat    5820
tgacaaagtt gttgtagtta aaggtactac aattgttgtc aatgttggaa aacctgtagt    5880
ggcaccatcg cacctctttc ttaagggtgt ttcctacaca acattcctag ataatggtaa    5940
cggtgttgcc ggccattata ctgttttttga tcatgacact ggtatggtgc atgatggaga    6000
tgttttttgta ccaggtgatc tcaatgtgtc tcctgttaca aatgttgtcg tctcagagca    6060
gacggctgtt gtgattaaag accctgtgaa gaaagtagag ttagacgcta caaagctgtt    6120
agacactatg aattatgcat cggaaagatt cttttccttt ggtgatttta tgtcacgtaa    6180
tttaattaca gtgttttgt acatccttag tattttgggt ctctgtttta gggcctttcg    6240
taagagggat gttaaagttc tagctggtgt accccaacgt actggtatta tattgcgtaa    6300
aagtgtgcgc tataatgcaa aggctttggg tgtcttcttc aagctaaaac tttattggtt    6360
caaagttctt ggtaagttta gtttgggtat ttatgcattg tatgcattac tattcatgac    6420
aatacgcttt acacctatag gtggccctgt ttgtgatgat gttgttgctg gttatgctaa    6480
ttctagtttt gacaagaatg agtattgcaa cagtgttatt tgtaaggtct gtctctatgg    6540
gtaccaggaa ctttcggact tctctcacac acaggtagta tggcaacacc ttagagaccc    6600
attaattggt aatgtgatgc ctttcttta tttggcattt ctggcaattt ttgggggtgt    6660
ttatgtaaag gctattactc tctatttat tttccagtat cttaacatac ttggtgtgtt    6720
tttgggccta caacagtcca tttggttttt gcagcttgtg ccttttgatg tctttggtga    6780
cgagatcgtc gtcttttca tcgttacacg cgtattgatg ttccttaagc atgttttcct    6840
tggctgcgat aaggcatctt gtgtggcttg ctctaagagt gctcgcctta agcgcgttcc    6900
tgtccagact attttcagg gtactagcaa atccttctac gtacatgcca atggtggttc    6960
taagttctgt aagaagcaca atttcttttg tttaaattgt gattcttatg gtccaggctg    7020
cactttatt aatgacgtca ttgcaactga agttggtaat gttgtcaaac ttaatgtgca    7080
accgacaggt cctgccacta ttcttattga caaggttgaa ttcagtaatg ttttttacta    7140
tctttatagt ggtgacacat tttggaagta caactttgac ataacagata acaaatacac    7200
ttgcaaagag tcacttaaaa attgtagcat aatcacagac tttattgttt ttaacaataa    7260
tggttccaat gtaaatcagg ttaagaatgc atgtgtgtat ttttcacaga tgctttgtaa    7320
acctgttaag ttagtggact cagcgttgtt ggccagtttg tctgttgatt ttggtgcaag    7380
cttacatagt gcttttgtta gtgtgttgtc gaatagtttt ggcaaagacc tgtcaagttg    7440
taatgacatg caggattgca agagcacatt gggttttgat gatgtaccat tggatacctt    7500
taatgctgct gttgctgagg ctcatcgtta cgatgtcctc ttgactgaca tgtcgttcaa    7560
caattttacc accagttatg caaaaccaga ggaaaaactt cccgtccatg acattgccac    7620
```

-continued

```
gtgtatgcgt gtaggtgcca agattgttaa tcataacgtt cttgtcaagg atagtatacc    7680
tgtggtgtgg cttgtacgtg atttcattgc cctttctgaa gaaactagga agtacattat    7740
tcgtacgact aaagttaagg gtataacctt catgttgacc tttaatgatt gtcgtatgca    7800
tactaccata cctactgttt gcattgcaaa taagaagggt gcaggtcttc ctagtttttc    7860
aaaggttaag aaattcttct ggttttgtg tctgttcata gttgctgttt tctttgcact    7920 aagcttttt gattttagta ctcaggttag cagtgatagt gattatgact tcaagtatat    7980
tgagagtggc cagttgaaga cttttgacaa tccacttagt tgtgtgcata atgtctttag    8040
taacttcgac cagtggcatg atgccaagtt tggtttcacc cccgtcaaca atcctagttg    8100
tcctatagtc gttggtgtat cagacgaagc gcgcactgtt ccaggtatcc cagcaggtgt    8160
ttatttagct ggtaaaacac ttgttttgc tattaacacc attttggta catctggttt    8220 gtgctttgat gctagtggcg ttgctgataa gggcgcttgc attttaatt cggcttgcac    8280 cacattatct ggtttgggtg gaactgctgt ctactgttat aagaatggtc tagttgaagg    8340
tgctaaactt tatagtgagt tggcacctca tagctactat aaaatggtag atggtaatgc    8400
tgtgtcttta cctgaaatta tctcacgcgg cttttggcatc cgtactatcc gtacaaaggc    8460 tatgaccttac tgtcgcgttg gccagtgtgt gcaatctgca gaaggtgttt gttttggcgc    8520
cgatagattc tttgtctata atgcagaatc tggttctgac tttgtttgtg gcacagggct    8580
ctttacattg ttgatgaacg ttattagtgt tttttccaag acagtaccag taactgtgtt    8640
gtctggtcaa atacttttta attgcattat tgcttttgct gctgttgcgg tgtgtttctt    8700
atttacaaag tttaagcgca tgttcggtga tatgtctgtt ggcgttttca ctgtcggtgc    8760 ttgtacttg ttgaacaatg tttcctacat tgtaacacag aacacacttg gcatgttggg    8820
ctatgcaact ttgtactttt tgtgcactaa aggtgttaga tatatgtgga tttggcatt    8880 gggatttttg atctcatata tacttattgc accatggtgg gttttgatgg tttatgcctt    8940
ttcagccatt tttgagttta tgcctaacct ttttaagctt aaggtttcaa cacaactttt    9000
tgagggtgac aagttcgtag gctcttttga aaatgctgca gcaggtacat ttgtgcttga    9060
tatgcatgcc tatgagagac ttgccaactc tatctcaact gaaaaactgc gtcagtatgc    9120
tagtacttac aataagtaca agtattattc aggcagtgct tcagaggctg attacaggct    9180
tgcttgtttt gcccatttgg ccaaggctat gatggattat gcttctaatc acaacgacac    9240
gttatacaca ccacccactg tgagttacaa ttcaactcta caggctggct tgcgtaagat    9300
ggcacaacca tctggtgttg ttgagaagtg catagttcgt gtttgctatg gtaatatggc    9360
tcttaatggc ctatggcttg gtgatactgt tatctgccca cgccatgtta tagcgtctag    9420
tactactagc actatagatt atgactatgc cctttctgtt ttacgcctcc acaacttctc    9480
catttcatct ggtaatgttt tcctaggtgt tgtgggtgta accatgcgag gtgctttgtt    9540
gcagataaag gttaatcaaa acaatgtcca cacgcctaag tacacctatc gcacagttag    9600
accgggtgaa tcttttaata tcttggcgtg ctatgatggt tctgcagctg gtgtttacgg    9660
cgttaacatg cgctctaatt acactattag aggctcgttc attaatggcg cttgtggttc    9720
acctggttat aacattaaca atggtaccgt tgagttttgc tatttacacc agcttgaact    9780
tggttcaggc tgtcatgttg gtagcgactt agatggtgtt atgtatggtg gttatgagga    9840
ccaacctact ttgcaagttg aaggcgctag tagtctgttt acagagaatg tgttggcatt    9900
tctttatgca gcactcatta atggttcac ctggtggctt agttcttcta ggattgctgt    9960
agacaggttt aatgagtggg ctgttcataa tggtatgaca acagtagtta atactgattg   10020
```

```
cttttctatt cttgctgcta agactggtgt tgatgtacaa cgtttgttgg cctcaatcca    10080
gtctctgcat aagaattttg gtggaaagca aattcttggc tatacctcgt tgacagatga    10140
gtttactaca ggtgaagtta tacgtcaaat gtatggcgtt aatcttcaga gtggttatgt    10200
ttcacgcgcc tgtagaaatg tcttgctggt tggttctttt ctgactttct tttggtcaga    10260
attagtttcc tacactaagt tcttttgggt aaatcctggt tatgtcacac ctatgtttgc    10320
gtgtttgtca ttgctgtcct cacttttgat gttcacactc aagcataaga cattgttttt    10380
ccaggtcttt ctaatacctg ctctgattgt tacatcttgc attaatttgg catttgatgt    10440
tgaagtctac aactatttgg cagagcattt tgattaccat gtttctctca tgggttttaa    10500
tgcacaaggt cttgttaaca tctttgtctg ctttgttgtt accatttttac acggcacata    10560 cacatggcgc ttttttaaca cacctgtgag ttctgtcact tatgtggtag ctttgctgac    10620
tgcggcatat aactattttt acgctagtga cattcttagt tgtgctatga cactatttgc    10680
tagtgtgact ggcaactggt tcgttggtgc tgtttgttat aaagctgctg tttatatggc    10740
cttgagattt cctacttttg tggctatttt tggtgatatt aagagtgtta tgttctgtta    10800
ccttgtgttg ggtatttta cctgttgctt ctacggtatt ctctactggt tcaacaggtt    10860
ttttaaggtt agtgtaggtg tctatgacta tactgttagt gctgctgagt ttaagtatat    10920
ggttgctaac ggcctacgtg caccaactgg aacacttgat tcactacttc tgtctgccaa    10980
attgattggt attggtggtg agcggaatat taagatttct tccgttcagt ctaaactgac    11040
tgatattaag tgtagtaacg ttgtgctttt aggctgtctc tctagcatga atgtctcagc    11100
aaattcaaca gaatgggcct attgtgttga cttgcataac aagatcaact tgtgtaatga    11160
cccagaaaaa gcgcaggaaa tgctactgc tttgttggca ttttccctta gtaagaatag    11220
tgcttttggt ttagatgact tattggaatc ctattttaat gacaatagta tgttgcagag    11280
tgttgcatct acttatgtcg gtttgccttc ttatgtcatt tatgaaaatg cacgccaaca    11340
gtatgaagat gctgttaata atggttctcc acctcagttg gttaagcaat gcgccatgc    11400 catgaatgta gcaaagagcg aatttgaccg tgaggcttct actcagcgta agcttgatag    11460
aatggcggaa caggctgcag cacagatgta caaagaggca cgagcagtta ataggaagtc    11520
caaagttgta agtgctatgc attcactgct ttttggtatg ttgagacgtt tggacatgtc    11580
ttctgtagac accattctca acttggcaaa ggatgggtt gtacctctgt ctgtcatacc    11640
ggcagtcagt gctactaagc ttaacattgt tacttctgat atcgattctt ataatcgtat    11700
ccagcgtgag ggatgtgtcc actacgctgg taccatttgg aatataattg atatcaagga    11760
caatgatggc aaggtggtac acgttaagga ggtaaccgca cagaatgctg agtccctgtc    11820 atggccctg gtccttgggt gtgagcgtat tgtcaagctc cagaataatg aaattattcc    11880
tggtaagctg aagcagcgct ccattaaggc agaaggagat ggcatagttg gagaaggtaa    11940 ggcacttttac aataatgagg gtggacgtac ttttatgtat gctttcatct cggacaaacc    12000
ggacctgcgt gtagtcaagt gggagttcga tggtggttgt aacactattg agctagaacc    12060
accacgtaag ttcttggtgg attctcctaa tggtgcacag atcaagtatc tctactttgt    12120
tcgtaacctt aacacgttac gtaggggtgc tgttctcggc tacataggtg ccactgtacg    12180
cttgcaggct ggtaaacaaa cagaacaggc tattaactct tcattgttga cactttgcgc    12240
tttcgctgtg gatcctgcta agaccctacat cgatgctgtc aaaagtggtc acaaaccagt    12300
aggtaactgt gttaagatgt tggccaatgg ttctggtaat ggacaagctg ttactaatgg    12360
```

```
tgtggaggct agtactaacc aggattcata cggtggtgcg tccgtgtgtc tatattgtag    12420
agcacatgtt gagcatccat ctatggatgg tttttgcaga ctgaaaggca agtacgtaca    12480
ggttccacta ggtacagtgg atcctatacg ttttgtactt gagaatgacg tttgcaaggt    12540
ttgtggttgt tggctggcta atggctgcac ttgtgacaga tccattatgc aaagcactga    12600
tatggcttat ttaaacgagt acggggctct agtgcagctc gactagagcc mtgtaacggt    12660
actgatacac aacatgtgta tcgtgctttt gacatctaca acaaggatgt tgcttgtcta    12720
ggtaaattcc tcaaggtgaa ctgtgttcgc ctgaagaatt tggataagca tgatgcattc    12780
tatgttgtca aaagatgtac caagtctgcg atggaacacg agcaatccat ctatagcaga    12840
cttgaaaagt gtggagccgt agccgaacac gatttcttca cttggaagga tggtcgtgcc    12900
atctatggta acgtttgtag aaaggatctt accgagtata ctatgatgga tttgtgttac    12960
gctttacgta actttgatga aaacaattgc gatgttctta agagcatttt aattaaggta    13020
ggcgcttgtg aggagtccta cttcaataat aaagtctggt ttgaccctgt tgaaaatgaa    13080
gacattcatc gtgtctatgc attgttaggt accattgttt cacgtgctat gcttaaatgc    13140
gttaagttct gtgatgcaat ggttgaacaa ggtatagttg gtgttgtcac attagataat    13200
caggatctta atggtgattt ttatgatttt ggtgatttta cttgtagcat caagggaatg    13260
ggtataccca tttgcacatc atattactct tatatgatgc ctgttatggg tatgactaat    13320
tgccttgcta gtgagtgttt tgttaagagt gatatatttg gtgaggattt caagtcatat    13380
gacctgctgg aatatgattt cacggagcat aagacagcac tcttcaacaa gtatttcaag    13440 tattgggggac tgcaatacca ccctaactgt gtggactgca gtgatgagca gtgcatagtt    13500
cactgtgcca acttcaatac gttgttttcc actactatac ctattacggc atttggacct    13560
ttgtgtcgca agtgttggat tgatggtgtt ccactggtaa ctacagctgg ttatcatttt    13620
aaacagttag gtatagtttg gaacaatgac ctcaacttac actctagcag gctctctatt    13680
aacgaattac tccagttttg tagtgatcct gcattgctta tagcatcatc accagcccct    13740
gttgatcagc gtactgtttg cttttcagtt gcagcgctag gtacaggtat gactaaccag    13800
actgttaaac ctggccattt caataaggag ttttatgact tcttacttga gcaaggtttc    13860
ttttctgagg gctctgagct tactttaaag cacttcttct ttgcacagaa gggtgatgca    13920
gctgttaagg atttgacta ctataggtat aatagaccta ctgttctgga catttgccaa    13980
gctcgcgtcg tgtatcaaat agtgcaacgc tattttgata tttacgaagg tggttgtatc    14040
actgctaaag aggtggttgt tacaaacctt aacaagagcg caggttatcc tttgaacaag    14100
tttggtaaag ctggtctttta ctatgagtct ttatcctatg aggaacagga tgaactttat    14160
gcttatacta agcgtaacat cctgcccact atgacacagc tcaaccttaa atatgctata    14220
agtggcaaag aacgtgcacg cacagtgggt ggtgtttcgc ttttgtcaac catgactact    14280
cggcagtatc atcagaaaca ccttaagtcc atagttaata ctaggggcgc ttcggttgtt    14340
attggtacta ctaagttta tggtggttgg gacaatatgc ttaagaacct tattgatggt    14400
gttgaaaatc cgtgtcttat gggttgggac tacccaaagt gcgacagagc actgcccaat    14460
atgatacgta tgatttcagc catgattta ggctctaagc acaccacatg ctgcagttcc    14520
actgaccgct ttttcaggtt gtgcaatgaa ttggctcaag tccttactga ggttgtttat    14580
tctaatggag ttttattt gaagccaggt ggtactacct ctggtgatgc aaccaccgca    14640
tatgcaaact cagtttttaa tatcttccaa gcagtaagtg ccaatgttaa caacttctt    14700 agtgttgaca gcaatgtctg tcataatttta gaagttaagc aattgcagcg taagctttat    14760
```

```
gagtgctgtt atagatcaac taccgtcgat gaccagttcg tcgttgagta ttatggttac   14820
ttgcgtaaac attttttcaat gatgattctt tctgatgatg gcgttgtttg ttataacaat   14880
gactatgcat cacttggtta tgtcgctgat cttaacgcat tcaaggctgt tttgtattac   14940
cagaacaatg tcttcatgag cgcctctaaa tgttggatcg agcctgacat taataaaggt   15000
cctcatgaat tttgctcgca gcatactatg cagattgtcg ataaagatgg tacttattac   15060
cttccttacc ctgatccttc aagaattctc tctgcaggtg tgtttgttga tgacgttgtt   15120
aaaactgatg cagttgtatt gcttgaacgt tatgtgtcat tggctataga tgcctacccg   15180
ttatctaagc atgaaaaccc tgaatataag aaggtgtttt atgtgctttt ggattgggtt   15240
aagcatctgt acaaaactct taatgctggt gtgttagagt cttttttctgt cacactttttg   15300 gaagattcta ctgctaaatt ctgggatgag agcttttatg ccaacatgta tgagaaatct   15360
gcagttttac aatctgcagg gctttgtgtt gtttgtggct ctcaaactgt tttacgttgt   15420
ggtgattgtc tacggcgtcc tatgcttttgt actaagtgtg cttatgatca tgtcattgga   15480
acaactcaca agttcatttt ggccatcact ccatatgtgt gttgtgcttc agattgtggt   15540
gtcaatgatg taactaagct ctacttaggt ggtcttagtt attggtgtca tgaccacaag   15600
ccacgtcttg cattcccgtt gtgctctgct ggtaatgttt ttggcttgta caaaaattct   15660
gctaccggct cacccgatgt tgaagacttt aatcgcattg ctacatccga ttggactgat   15720
gtttctgact acaggttggc aaatgatgtc aaggactcat tgcgtctgtt tgcagcggaa   15780
actatcaagg ccaaggagga gagcgttaag tcatcctatg cttgtgcaac actacatgag   15840
gttgtaggac ctaaagagtt gttgctcaaa tgggaagtcg gcagacccaa accacccctt   15900
aatagaaatt cggttttcac ttgttatcat ataacgaaga acaccaaatt tcaaatcggt   15960
gagtttgtgt ttgagaaggc agaatatgat aatgatgctg taacatataa aactaccgcc   16020
acaacaaaac ttgttcctgg catggttttt gtgcttacct cacataatgt tcagccattg   16080
cgcgcaccga ccattgctaa tcaagaacgt tattccacta tacataagtt gcatcctgct   16140
tttaacatac ctgaagctta ttctagctta gtgccctatt accaattgat tggtaagcag   16200
aagattacaa ctattcaggg acctcccggt agtggtaaat ctcactgtgt tataggtgta   16260
ggtttgtact atccaggtgc acgtatagtg tttacagctt gttctcatgc agcggtcgat   16320
tcactttgtg tgaaagcttc cactgcttat agcaatgaca aatgttcacg catcatacca   16380
cagcgcgctc gtgttgagtg ttatgatggt ttcaagtcta ataatactag tgctcagtac   16440
cttttctcta ctgtcaatgc tttgccagag tgcaatgcgg acattgttgt ggtggatgag   16500
gtctctatgt gcactaatta tgacttgtct gtcataaatc agcgcatcag ctataggcat   16560
gtagtctatg ttggtgaccc tcaacagctg cctgcaccac gtgttatgat tcacgtggt   16620 actttggaac caaaggacta caacgttgtc actcaacgca tgtgtgccct taagcctgat   16680
gttttcttgc acaagtgtta tcgctgtcct gctgagatag tgcgtactgt gtctgagatg   16740
gtctatgaaa accaattcat tcctgtgcac ccagatagca agcagtgttt taaaatcttt   16800
tgcaagggta atgttcaggt tgataatggt tcaagcatta atcgcaggca attggatgtt   16860
gtgcgtatgt ttttggctaa aaatcctagg tggtcaaagg ctgttttttat ttctccttat   16920 aacagccaga attatgttgc cagccgcatg ctaggtctac aaattcagac agttgactca   16980
tcccagggta gtgagtatga ctatgtcatt tacacacaaa cttcagatac tgcccatgcc   17040
tgtaatgtta acaggtttaa tgttgccatc acaagggcca agaaaggcat attatgtata   17100
```

```
atgtgcgata ggtcccttt tgatgtgctt aaattctttg agcttaaatt gtctgatttg      17160
caggctaatg agggttgtgg tcttttaaa gactgtagca gaggtgatga tctgttgcca      17220
ccatctcacg ctaacacctt catgtctta gcggacaatt ttaagactga tcaagatctt      17280
gctgttcaaa taggtgttaa tggacccatt aaatatgagc atgttatctc gtttatgggt      17340
ttccgttttg atatcaacat acccaaccat catactctct tttgcacacg cgactttgcc      17400
atgcgcaatg ttagaggttg gttaggcttt gacgttgaag gagcacatgt tgttggctct      17460
aacgtcggta caaatgtccc attgcaatta gggttttcta acggtgttga ttttgttgtc      17520
agacctgaag gttgcgttgt aacagagtct ggtgactaca ttaaacccgt cagagctcgt      17580
gctccaccag gggaacaatt cgcacacctt ttgcctttac ttaaacgcgg ccaaccatgg      17640
gatgttgtcc gcaaacgtat agtgcagatg tgtagtgact acctggccaa cctatcagac      17700
atactaattt ttgtgttgtg ggctggtggt ttggagttga caactatgcg ttattttgtc      17760
aagattggac caagtaagag ttgtgattgt ggtaaggttg ctacttgtta caatagtgcg      17820
ctgcatacgt actgttgttt caaacatgcc cttggttgtg attatctgta taacccatac      17880
tgtattgata tacagcagtg gggatacaag ggatcactta gccttaacca ccatgagcat      17940
tgtaatgtac atagaaacga gcatgtggct tctggtgatg ccataatgac tcgctgtctg      18000
gccatacatg attgctttgt caagaacgtt gactggtcca tcacataccc atttattggt      18060
aatgaggctg ttattaataa gagcggccga attgtgcaat cacacactat gcggtcagtt      18120
cttaagttat acaatccgaa agccatatat gatattggca atcctaaggg cattagatgt      18180
gccgtaacgg atgctaagtg ttttgctttt gacaagaatc ctactaattc taatgtcaag      18240
acattggagt atgactatat aacacatggc caatttgatg ggttgtgctt gttttggaat      18300
tgcaatgtag acatgtatcc agaatttcct gtggtctgtc gttttgatac tcgctgtagg      18360
tcaccactca acttggaggg ttgtaatggt ggttcactgt atgttaataa tcatgcattc      18420
catacaccgg cttttgacaa gcgtgctttt gctaagttga agccaatgcc attttctttt      18480
tatgatgata ctgagtgtga caagttacag gactccataa actatgttcc tcttagggct      18540
agtaactgca ttactaaatg taatgttggt ggtgctgtct gtagtaagca ttgtgctatg      18600
tatcatagct atgttaatgc ttacaacact tttacgtcgg cgggctttac tatttgggtg      18660
cctacttcgt ttgacaccta taatctgtgg cagacattta gtaacaattt gcaaggtctt      18720
gagaacattg ctttcaatgt cgtaaagaaa ggatcttttg ttggtgccga aggtgaactt      18780
cctgtagctg tggttaatga caaagtgctc gttagagatg gtactgttga tactcttgtt      18840
tttacaaaca agacatcact acccactaac gtagcttttg agttgtatgc caagcgtaag      18900
gtaggactca ccccacccat tacgatccta cgtaacttgg gtgtagtttg tacatctaag      18960
tgtgtcattt gggactatga agccgaacgt ccacttacta cttttacaaa ggatgtttgt      19020
aaatataccg actttgaggg tgacgtctgt acactctttg ataacagcat tgttggttca      19080
ttagagcgat tctccatgac ccaaaatgct gtgcttatgt cacttacagc tgttaaaag      19140 cttactggca taaagttaac ttatggttat cttaatggtg tcccagttaa cacacatgaa      19200
gataaacctt ttacttggta tatttacact aggaagaacg gcaagttcga ggaccatcct      19260
gatggctatt ttacccaagg tagaacaacc gctgatttta gccctcgtag cgacatggaa      19320
aaggacttcc taagtatgga tatgggtctg tttattaaca gtacggact tgaagattac      19380 ggcttgagc acgttgtgta tggtgatgtt tcaaaaacca cccttggtgg tttgcatcta      19440
ctaatttcgc aggtgcgtct ggcctgtatg ggtgtgctca aaatagacga gtttgtgtct      19500
```

-continued

```
agtaatgata gcacgttaaa gtcttgtact gttacatatg ctgataaccc tagtagtaag  19560
atggtttgta cgtatatgga tctcctgctt gacgattttg tcagcattct taaatctttg  19620
gatttgggcg ttgtatctaa agttcatgaa gttatggtcg attgtaaaat gtggaggtgg  19680
atgttgtggt gtaaggatca taaactccag acattttatc cgcaacttca ggccagtgaa  19740
tggaagtgtg gttattccat gccttctatt tacaagatac aacgtatgtg tttagaacct  19800
tgcaatctct acaactatgg tgctggtatt aagttacctg atggcattat gtttaacgta  19860
gttaaataca cacagctttg tcaatatctc aatagcacca caatgtgtgt accccatcac  19920
atgcgtgtgc tacatcttgg tgctggctcc gacaagggtg ttgcacctgg cacggctgtc  19980
ttacgacgtt ggttgccact ggatgccatt atagttgaca atgatagtgt ggattacgtt  20040
agcgatgctg attatagtgt tacaggagat tgctctacct tatacctgtc agataagttt  20100
gatttagtta tatctgatat gtatgatggt aagattaaaa gttgtgatgg ggagaacgtg  20160
tctaaagaag gcttctttcc ctatattaat ggtgtcatca ccgaaaagtt ggcacttggt  20220
ggtactgtag ctattaaggt gacggagttt agttggaata agaagttgta tgaactcatt  20280
cagaggtttg agtattggac aatgttctgt accagtgtta acacgtcatc gtcagaggca  20340
ttcttaattg gtgttcacta tttaggtgat tttgcaagtg gcgctgtgat tgacggcaac  20400
actatgcatg ccaattatat cttctggcgt aattccacaa ttatgactat gtcttacaat  20460
agtgtacttg atttaagcaa gttcaattgt aagcataagg ctacagttgt cattaattta  20520
aaagattcat ccattagtga tgttgtgtta ggtttgttga agaatggtaa gttgctagtg  20580
cgtaataatg acgccatttg tggttttctct aatcatttgg tcaacgtaaa caaatgaagt  20640
ctttaaccta cttctggttg ttcttaccag tactttcaac acttagccta ccacaagatg  20700
tcaccaggtg ctcagctaac actaattttta ggcggttctt ttcaaaattt aatgttcagg  20760
cgcctgcagt tgttgtactg ggcggttatc tacctattgg tgaaaaccag ggtgtcaatt  20820
caacttggta ctgtgctggc caacatccaa ctgctagtgg cgttcatggt atctttgtta  20880
gccatattag aggtggtcat ggcttttgaga ttggcatttc gcaagagcct tttgacccta  20940
gtggttacca gctttatttta cataaggcta ctaacggtaa cactaatgct actgcgcgac  21000
tgcgcatttg ccagtttcct agcattaaaa cattgggccc cactgctaat aatgatgtta  21060
caacaggtcg taattgccta tttaacaaag ccatcccagc tcatatgagt gaacatagtg  21120
ttgtcggcat aacatgggat aatgatcgtg tcactgtctt ttctgacaag atctattatt  21180 tttatttttaa aaatgattgg tcccgtgttg cgacaaagtg ttacaacagt ggaggttgtg  21240
ctatgcaata tgtttacgaa cccacctatt acatgcttaa tgttactagt gctggtgagg  21300
atggtatttc ttatcaaccc tgtacagcta attgcattgg ttatgctgcc aatgtatttg  21360
ctactgagcc caatggccac ataccagaag gttttagttt taataattgg tttcttttgt  21420
ccaatgattc cactttggtg catggtaagg tggtttccaa ccaaccattg ttggtcaatt  21480 gtctttttggc cattcctaag atttatggac taggccaatt tttctccttt aatcaaacga  21540
tcgatggtgt ttgtaatgga ctgctgtgc agcgtgcacc agaggctctg aggtttaata  21600
ttaatgacac ctctgtcatt cttgctgaag gctcaattgt acttcatact gctttaggaa  21660 caaattttc ttttgtttgc agtaattcct caaatcctca cttagccacc ttcgccatac  21720
ctctgggtgc tacccaagta ccttattatt gttttcttaa agtggatact tacaactcca  21780
ctgtttataa attttttggct gttttacctc ctaccgtcag ggaaattgtc atcaccaagt  21840
```

```
atggtgatgt ttatgtcaat gggtttggat acttgcatct cggtttgttg gatgctgtca   21900
caattaattt cactggtcat ggcactgacg atgatgtttc tggtttttgg accatagcat   21960
cgactaattt tgttgatgca ctcatcgaag ttcaaggaac cgccattcag cgtattcttt   22020
attgtgatga tcctgttagc caactcaagt gttctcaggt tgcttttgac cttgacgatg   22080 gttttttaccc tatttcttct agaaaccttc tgagtcatga acagccaatt tcttttgtta   22140
ctctgccatc atttaatgat cattcttttg ttaacattac tgtatctgct cctttggtg    22200 gtcatagtgg tgccaacctt attgcatctg acactactat caatgggttt agttctttct   22260
gtgttgacac tagacaattt accatttcac tgttttataa cgttacaaac agttatggtt   22320
atgtgtctaa atcacaggac agtaattgcc ctttcacctt gcaatctgtt aatgattacc   22380
tgtcttttag caaattttgt gtttccacca gccttttggc tagtgcctgt accatagatc   22440 ttttggtta ccctgagttt ggtagtggtg ttaagttac gtcccttac tttcaattca       22500 caaagggtga gttgattact ggcacgccta aaccacttga aggtgtcacg gacgtttctt   22560
ttatgactct ggatgtgtgt accaagtata ctatctatgg ctttaaaggt gagggtatca   22620
ttacccttac aaattctagc ttttttggcag gtgtttatta cacatctgat tctggacagt   22680
tgttagcctt taagaatgtc actagtgtg ctgtttattc tgttacgcca tgttcttttt    22740
cagagcaggc tgcatatgtt gatgatgata tagtgggtgt tatttctagt ttgtctagct   22800 ccactttaa cagtactagg gagttgcctg gtttcttcta ccattctaat gatggctcta   22860
attgtacaga gcctgtgttg gtgtatagta acatggtgt ttgtaaatct ggcagtattg    22920
gctacgtccc atctcagtct ggccaagtca agattgcacc cacggttact gggaatatta   22980
gtattcccac caactttagt atgagtatta ggacagaata tttacagctt tacaacacgc   23040
ctgttagtgt tgattgtgcc acatatgttt gtaatggtaa ctctcgttgt aaacaattac   23100
tcacccagta cactgcagca tgtaagacca tagagtcagc attacaactc agcgctaggc   23160
ttgagtctgt tgaagttaac tctatgctta ctatttctga agaggctcta cagttagcta   23220
ccattagttc gtttaatggt gatggatata attttactaa tgtgctgggt gtttctgtgt   23280
atgatcctgc aagtggcagg gtggtacaaa aaaggtcttt tattgaagac ctgctttta    23340 ataaagtggt tactaatggc cttggtactg ttgatgaaga ctataagcgc tgttctaatg   23400
gtcgctctgt ggcagatcta gtctgtgcac agtattactc tggtgtcatg gtactacctg   23460
gtgttgttga cgctgagaag cttcacatgt atagtgcgtc tctcatcggt ggtatggtgc   23520
taggaggttt tacttctgca gcggcattgc cttttagcta tgctgttcaa gctagactca   23580
attatcttgc tctacagacg gatgttctac agcggaacca gcaattgctt gctgagtctt   23640
ttaactctgc tattggtaat ataacttcag cctttgagag tgttaaagag gctattagtc   23700
aaacttccaa gggttgaac actgtggctc atgcgcttac taaggttcaa gaggttgtta   23760
actcgcaggg tgcagctttg actcaactta ccgtacagct gcaacacaac ttccaagcca   23820
tttctagttc tattgatgac atttactctc gactggacat tctttcagcc gatgttcagg   23880
ttgaccgtct catcaccggc agattatcag cacttaatgc ttttgttgct caaaccctca   23940
ctaagtatac tgaggttcag gctagcagga gttagcaca gcaaaaggtt aatgagtgcg     24000
ttaaatcgca atctcagcgt tatggttttt gtggtggtga tggcgagcac attttctctc   24060
tggtacaggc agcacctcag ggcctgctgt ttttacatac agtacttgta ccgagtgatt   24120
ttgtagatgt tattgccatc gctggcttat gcgttaacga tgaaattgcc ttgactctac   24180
gtgagcctgg cttagtcttg tttacgcatg aacttcaaaa tcatactgcg acggaatatt   24240
```

```
ttgtttcatc gcgacgtatg tttgaaccta gaaaacctac cgttagtgat tttgttcaaa   24300
ttgagagttg tgtggtcacc tatgtcaatt tgactagaga ccaactacca gatgtaatcc   24360
cagattacat cgatgttaac aaaacacttg atgagatttt agcttctctg cccaatagaa   24420
ctggtccaag tcttccttta gatgttttta atgccactta tcttaatctc actggtgaaa   24480
ttgcagattt agagcagcgt tcagagtctc tccgtaatac tacagaggag ctccaaagtc   24540
ttatatataa tatcaacaac acactagttg accttgagtg gctcaaccga gttgagacat   24600
atatcaagtg gccgtggtgg gtttggttga ttattttcat tgttctcatc tttgttgtgt   24660
cattactagt gttctgctgc atttccacgg gttgttgtgg atgctgcggc tgctgctgtg   24720
cttgtttctc aggttgttgt aggggtccta gacttcaacc ttacgaagtt tttgaaaagg   24780
tccacgtgca gtgatgtttc ttggactttt tcaatacacg attgacacag ttgtcaaaga   24840
tgtctcaaag tctgctaact tgtctttgga tgctgtccaa gagttggagc tcaatgtagt   24900
tccaattaga caagcttcaa atgtgacggg ttttcttttc accagtgttt ttatctactt   24960
ctttgcactg tttaaagcgt cttctttgag gcgcaattat attatgttgg cagcgcgttt   25020
tgctgtcatt gttctttatt gcccacttt atattattgt ggtgcatttt tagatgcaac    25080
tattatttgt tgcacactta ttggcaggct ttgtttagtc tgcttttact cctggcgcta   25140
taaaaatgcg ctcttatta tttttaatac tacgacactt tctttcctca atggtaaagc     25200
agcttattat gacggcaaat ccattgtgat tttagaaggt ggtgaccatt acatcacttt   25260
tggcaactct cttgttgctt ttgttagtag catcgacttg tatctagcta tacgtgggcg   25320
gcaagaagct gacctacagc tgttgcgaac tgttgagctt cttgatggca agaagcttta   25380
tgtcttttcg caacatcaaa ttgttggcat tactaatgct gcatttgact caattcaact   25440
agacgagtat gctacaatta gtgaatgata atggtctagt agttaatgtt atactttggc   25500
ttttcgtact ctttttcctg cttattataa gcattacttt cgtccaattg gttaatctgt   25560
gcttcacttg tcaccggttg tgtaatagcg cagtttacac acctataggg cgtttgtata   25620
gagtttataa gtcttacatg caaatagacc ccctccctag tactgttatt gacgtataaa   25680
cgaaatatgt ctaacggttc tattcccgtt gatgaggtga ttcaacacct tagaaactgg   25740
aatttcacat ggaatatcat actgacgata ctacttgtag tgcttcagta tggccattac   25800
aagtactctg cgttcttgta tggtgtcaag atggctattc tatggatact ttggcctctt   25860
gtgttagcac tgtcactttt tgatgcatgg gctagctttc aggtcaattg ggtctttttt   25920
gctttcagca tccttatggc ttgcatcact cttatgctgt ggataatgta ctttgtcaat   25980
agcattcggt tgtggcgcag gacacattct tggtggtctt tcaatcctga aacagacgcg   26040
cttctcacta cttctgtgat gggccgacag gtctgcattc cagtgcttgg agcaccaact   26100
ggtgtaacgc taacactcct tagtggtaca ttgcttgtag agggctataa ggttgctact   26160
ggcgtacagg taagtcaatt acctaatttc gtcacagtcg ccaaggccac tacaacaatt   26220
gtctacggac gtgttggtcg ttcagtcaat gcttcatctg cactggttg ggcttttctat    26280 gtccggtcca aacacggcga ctactcagct gtgagtaatc cgagttcggt tctcacagat   26340
agtgagaaag tgcttcattt agtctaaaca gaaactttat ggcttctgtc agttttcagg   26400
atcgtggccg caaacgggtg ccattatccc tctatgcccc tcttagggtt actaatgaca   26460
aacccctttc taaggtactt gcaaataatg ctgtacccac taataaagga aataaggacc   26520
agcaaattgg atactggaat gagcaaattc gctggcgcat gcgccgtggt gagcgaattg   26580
```

```
aacaaccttc caattggcat ttctactacc tcggaacagg acctcacgcc gacctccgct    26640
ataggactcg tactgagggt gttttctggg ttgctaaaga aggcgcaaag actgaaccca    26700
ctaacctggg tgtcagaaag gcgtctgaaa agccaattat tccaaatttc tctcaacagc    26760
ttcccagcgt agttgagatt gttgaaccta acacacctcc tacttcacgt gcaaattcac    26820
gtagcaggag tcgtggtaat ggcaacaaca ggtccagatc tccaagtaac aacagaggca    26880
ataaccagtc ccgcggtaat tcacagaatc gtggaaataa ccagggtcgt ggagcttctc    26940
agaacagagg aggcaataat aataacaata acaagtctcg taaccagtcc aagaacagaa    27000
accagtcaaa tgaccgtggt ggtgtaacat cacgcgatga tctggtggct gctgtcaagg    27060
atgcccttaa atctttgggt attggcgaaa accctgacaa gcttaagcaa cagcagaagc    27120
ccaaacagga aaggtctgac agcagcggca aaaatacacc taagaagaac aaatccagag    27180
ccacttcgaa agaacgtgac ctcaaagaca tcccagagtg gaggagaatt cccaagggcg    27240
aaaatagcgt agcagcttgc ttcggaccca ggggaggctt caaaaatttt ggagatgcgg    27300
aatttgtcga aaaggtgtt gatgcctcag gctatgctca gatcgccagt ttagcaccaa    27360
atgttgcagc attgctcttt ggtggtaatg tggctgttcg tgagctagcg gactcttacg    27420
agattacata taattataaa atgactgtgc caaagtctga tccaaatgta gagcttcttg    27480
tttcacaggt ggatgcattt aaaactggga atgcaaaacc ccagagaaag aaggaaaaga    27540
agaacaagcg tgaaaccacg cagcagctga atgaagaggc catctacgat gatgtgggtg    27600
tgccatctga tgtgactcat gccaatttgg aatgggacac agctgttgat ggtggtgaca    27660
cggccgttga aattatcaac gagatcttcg acacaggaaa ttaaacaatg tttgactggc    27720
ttatcctggc tatgtcccag ggtagtgcca ttacactgtt attactgagt gttttctag    27780 cgacttggct gctgggctat ggcttttgccc tctaactagc ggtcttggtc ttgcacacaa    27840
cggtaagcca gtggtaatgt cagtgcaaga aggatattac catagcactg tcatgagggg    27900
aacgcagtac cttttcatct aaacctttgc acgagtaatc aaagatccgc ttgacgagcc    27960
tatatggaag agcgtgccag gtatttgact caaggactgt tagtaactga agacctgacg    28020
gtgttgatat ggatacac                                                  28038
```

<210> SEQ ID NO 21
<211> LENGTH: 1386
<212> TYPE: PRT
<213> ORGANISM: Porcine epidemic diarrhea virus

<400> SEQUENCE: 21

```
Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ile Gly Glu Asn Gln Gly Val Asn Ser Thr
        50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110
```

```
Thr Asn Gly Asn Thr Asn Ala Thr Ala Arg Leu Arg Ile Cys Gln Phe
            115                 120                 125

Pro Ser Ile Lys Thr Leu Gly Pro Thr Ala Asn Asn Asp Val Thr Thr
130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Lys Asn Asp Trp Ser Arg Val
            180                 185                 190

Ala Thr Lys Cys Tyr Asn Ser Gly Cys Ala Met Gln Tyr Val Tyr
        195                 200                 205

Glu Pro Thr Tyr Tyr Met Leu Asn Val Thr Ser Ala Gly Glu Asp Gly
210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
        290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365

Val Pro Tyr Tyr Cys Phe Leu Lys Val Asp Thr Tyr Asn Ser Thr Val
370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
450                 455                 460

Asp Asp Pro Val Ser Gln Leu Lys Cys Ser Gln Val Ala Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
        515                 520                 525

Leu Ile Ala Ser Asp Thr Thr Ile Asn Gly Phe Ser Ser Phe Cys Val
```

```
                530            535              540
    Asp Thr Arg Gln Phe Thr Ile Ser Leu Phe Tyr Asn Val Thr Asn Ser
    545                 550                 555                 560

Tyr Gly Tyr Val Ser Lys Ser Gln Asp Ser Asn Cys Pro Phe Thr Leu
                        565                 570                 575

Gln Ser Val Asn Asp Tyr Leu Ser Phe Ser Lys Phe Cys Val Ser Thr
                    580                 585                 590

Ser Leu Leu Ala Ser Ala Cys Thr Ile Asp Leu Phe Gly Tyr Pro Glu
                595                 600                 605

Phe Gly Ser Gly Val Lys Phe Thr Ser Leu Tyr Phe Gln Phe Thr Lys
            610                 615                 620

Gly Glu Leu Ile Thr Gly Thr Pro Lys Pro Leu Glu Gly Val Thr Asp
    625                 630                 635                 640

Val Ser Phe Met Thr Leu Asp Val Cys Thr Lys Tyr Thr Ile Tyr Gly
                        645                 650                 655

Phe Lys Gly Glu Gly Ile Ile Thr Leu Thr Asn Ser Ser Phe Leu Ala
                    660                 665                 670

Gly Val Tyr Tyr Thr Ser Asp Ser Gly Gln Leu Leu Ala Phe Lys Asn
                675                 680                 685

Val Thr Ser Gly Ala Val Tyr Ser Val Thr Pro Cys Ser Phe Ser Glu
            690                 695                 700

Gln Ala Ala Tyr Val Asp Asp Ile Val Gly Val Ile Ser Ser Leu
    705                 710                 715                 720

Ser Ser Ser Thr Phe Asn Ser Thr Arg Glu Leu Pro Gly Phe Phe Tyr
                        725                 730                 735

His Ser Asn Asp Gly Ser Asn Cys Thr Glu Pro Val Leu Val Tyr Ser
                    740                 745                 750

Asn Ile Gly Val Cys Lys Ser Gly Ser Ile Gly Tyr Val Pro Ser Gln
                755                 760                 765

Ser Gly Gln Val Lys Ile Ala Pro Thr Val Thr Gly Asn Ile Ser Ile
            770                 775                 780

Pro Thr Asn Phe Ser Met Ser Ile Arg Thr Glu Tyr Leu Gln Leu Tyr
    785                 790                 795                 800

Asn Thr Pro Val Ser Val Asp Cys Ala Thr Tyr Val Cys Asn Gly Asn
                        805                 810                 815

Ser Arg Cys Lys Gln Leu Leu Thr Gln Tyr Thr Ala Ala Cys Lys Thr
                    820                 825                 830

Ile Glu Ser Ala Leu Gln Leu Ser Ala Arg Leu Glu Ser Val Glu Val
                835                 840                 845

Asn Ser Met Leu Thr Ile Ser Glu Glu Ala Leu Gln Leu Ala Thr Ile
            850                 855                 860

Ser Ser Phe Asn Gly Asp Gly Tyr Asn Phe Thr Asn Val Leu Gly Val
    865                 870                 875                 880

Ser Val Tyr Asp Pro Ala Ser Gly Arg Val Gln Lys Arg Ser Phe
                        885                 890                 895

Ile Glu Asp Leu Leu Phe Asn Lys Val Val Thr Asn Gly Leu Gly Thr
                    900                 905                 910

Val Asp Glu Asp Tyr Lys Arg Cys Ser Asn Gly Arg Ser Val Ala Asp
                915                 920                 925

Leu Val Cys Ala Gln Tyr Tyr Ser Gly Val Met Val Leu Pro Gly Val
            930                 935                 940

Val Asp Ala Glu Lys Leu His Met Tyr Ser Ala Ser Leu Ile Gly Gly
    945                 950                 955                 960
```

-continued

```
Met Val Leu Gly Gly Phe Thr Ser Ala Ala Ala Leu Pro Phe Ser Tyr
              965                 970                 975

Ala Val Gln Ala Arg Leu Asn Tyr Leu Ala Leu Gln Thr Asp Val Leu
              980                 985                 990

Gln Arg Asn Gln Gln Leu Leu Ala Glu Ser Phe Asn Ser Ala Ile Gly
              995                1000                1005

Asn Ile Thr Ser Ala Phe Glu Ser Val Lys Glu Ala Ile Ser Gln
          1010                1015                1020

Thr Ser Lys Gly Leu Asn Thr Val Ala His Ala Leu Thr Lys Val
          1025                1030                1035

Gln Glu Val Val Asn Ser Gln Gly Ala Ala Leu Thr Gln Leu Thr
          1040                1045                1050

Val Gln Leu Gln His Asn Phe Gln Ala Ile Ser Ser Ser Ile Asp
          1055                1060                1065

Asp Ile Tyr Ser Arg Leu Asp Ile Leu Ser Ala Asp Val Gln Val
          1070                1075                1080

Asp Arg Leu Ile Thr Gly Arg Leu Ser Ala Leu Asn Ala Phe Val
          1085                1090                1095

Ala Gln Thr Leu Thr Lys Tyr Thr Glu Val Gln Ala Ser Arg Lys
          1100                1105                1110

Leu Ala Gln Gln Lys Val Asn Glu Cys Val Lys Ser Gln Ser Gln
          1115                1120                1125

Arg Tyr Gly Phe Cys Gly Gly Asp Gly Glu His Ile Phe Ser Leu
          1130                1135                1140

Val Gln Ala Ala Pro Gln Gly Leu Leu Phe Leu His Thr Val Leu
          1145                1150                1155

Val Pro Ser Asp Phe Val Asp Val Ile Ala Ile Ala Gly Leu Cys
          1160                1165                1170

Val Asn Asp Glu Ile Ala Leu Thr Leu Arg Glu Pro Gly Leu Val
          1175                1180                1185

Leu Phe Thr His Glu Leu Gln Asn His Thr Ala Thr Glu Tyr Phe
          1190                1195                1200

Val Ser Ser Arg Arg Met Phe Glu Pro Arg Lys Pro Thr Val Ser
          1205                1210                1215

Asp Phe Val Gln Ile Glu Ser Cys Val Val Thr Tyr Val Asn Leu
          1220                1225                1230

Thr Arg Asp Gln Leu Pro Asp Val Ile Pro Asp Tyr Ile Asp Val
          1235                1240                1245

Asn Lys Thr Leu Asp Glu Ile Leu Ala Ser Leu Pro Asn Arg Thr
          1250                1255                1260

Gly Pro Ser Leu Pro Leu Asp Val Phe Asn Ala Thr Tyr Leu Asn
          1265                1270                1275

Leu Thr Gly Glu Ile Ala Asp Leu Glu Gln Arg Ser Glu Ser Leu
          1280                1285                1290

Arg Asn Thr Thr Glu Glu Leu Gln Ser Leu Ile Tyr Asn Ile Asn
          1295                1300                1305

Asn Thr Leu Val Asp Leu Glu Trp Leu Asn Arg Val Glu Thr Tyr
          1310                1315                1320

Ile Lys Trp Pro Trp Trp Val Trp Leu Ile Ile Phe Ile Val Leu
          1325                1330                1335

Ile Phe Val Val Ser Leu Leu Val Phe Cys Cys Ile Ser Thr Gly
          1340                1345                1350
```

-continued

```
Cys Cys  Gly Cys Cys Gly Cys  Cys Cys Ala Cys Phe  Ser Gly Cys
    1355                1360                1365

Cys Arg  Gly Pro Arg Leu Gln  Pro Tyr Glu Val Phe  Glu Lys Val
    1370                1375                1380

His Val  Gln
    1385

<210> SEQ ID NO 22
<211> LENGTH: 1386
<212> TYPE: PRT
<213> ORGANISM: Porcine epidemic diarrhea virus
<220> FEATURE:
<221> NAME/KEY: misc_feature
<222> LOCATION: (728)..(728)
<223> OTHER INFORMATION: Xaa can be any naturally occurring amino acid
<220> FEATURE:
<221> NAME/KEY: misc_feature
<222> LOCATION: (905)..(905)
<223> OTHER INFORMATION: Xaa can be any naturally occurring amino acid

<400> SEQUENCE: 22

Met Arg Ser Leu Ile Tyr Phe Trp Leu Ser Leu Pro Val Leu Pro Thr
1               5                   10                  15

Leu Ser Leu Pro Gln Asp Val Tyr Arg Cys Ser Ala Arg Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ser Gly Glu Thr Gln Gly Gly Ala Pro Arg
    50                  55                  60

Trp Tyr Cys Ala Gly Arg His Glu Thr Ala Ser Gly Val His Gly Ile
65                  70                  75                  80

Phe Leu Ser His Ile Arg Gly Gly His Gly Phe Glu Ile Gly Ile Ser
                85                  90                  95

Gln Glu Pro Leu Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Asn Lys Thr Leu Gly Pro Thr Ala Asn Asp Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ala Asp Lys Ile Tyr His Phe Tyr Leu Lys Asn Glu Trp Ser Arg Val
            180                 185                 190

Ala Thr Lys Cys Tyr Asn Ser Gly Gly Cys Ala Met Gln Tyr Val Tyr
        195                 200                 205

Glu Pro Ile Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Ala Thr Glu Ser Asn Gly His Ile Pro Glu Gly Phe Ser Phe
                245                 250                 255

Asn Asn Trp Phe Leu Leu Ser Asn Asp Ser Thr Leu Phe His Gly Lys
            260                 265                 270

Val Val Ser Asn Gln Pro Leu Leu Val Asn Cys Leu Trp Ala Ile Pro
        275                 280                 285
```

```
Lys Ile Tyr Gly Leu Gly His Phe Ser Phe Asn Gln Thr Met Asp
    290                 295                 300

Gly Val Cys Asn Gly Ala Thr Ala Tyr Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Leu Ser Phe Val Cys Ser Asn Ser
                340                 345                 350

Ser Asp Pro His Lys Ala Ile Phe Ser Ile Pro Leu Gly Ala Thr Gln
                355                 360                 365

Val Pro Tyr Tyr Cys Phe Leu Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asn
                420                 425                 430

Asp Asp Val Ser Gly Phe Trp Thr Ile Ala Ser Thr Asn Phe Ile Asp
                435                 440                 445

Ala Leu Val Glu Val Arg Ala Thr Ala Ile Gln Arg Ile Leu Tyr Cys
    450                 455                 460

Asp Asp Pro Val Cys Gln Leu Lys Cys Ser Gln Val Ser Phe Asp Leu
465                 470                 475                 480

Asp Asp Gly Phe Tyr Pro Ile Ser Ser Arg Asn Leu Leu Ser His Glu
                485                 490                 495

Gln Pro Ile Ser Phe Val Thr Leu Pro Ser Phe Asn Asp His Ser Phe
                500                 505                 510

Val Asn Ile Thr Val Ser Ala Ala Phe Gly Asp Ser Gly Gly Ala Asn
    515                 520                 525

Leu Val Ala Ser Asp Thr Thr Ile Asn Gly Phe Ser Ser Phe Cys Val
    530                 535                 540

Asp Thr Arg Gln Phe Thr Ile Arg Leu Phe Tyr Asn Val Thr Ser Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
                580                 585                 590

Ser Leu Leu Ala Gly Ala Cys Thr Ile Asp Leu Phe Gly Tyr Pro Ala
    595                 600                 605

Phe Gly Ser Gly Val Lys Phe Thr Ser Leu Tyr Phe Gln Phe Thr Lys
610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Val Tyr Tyr Thr Ser Asp Ser Gly Gln Leu Leu Ala Phe Lys Asn
                675                 680                 685

Val Thr Ser Gly Ala Val Tyr Ser Val Thr Pro Cys Ser Phe Ser Glu
    690                 695                 700

Gln Ala Ala Tyr Val Asp Asp Asp Ile Val Gly Gly Ile Ser Ser Leu
```

```
                705                 710                 715                 720
Ser Asn Ser Thr Phe Asn Asn Xaa Arg Asp Phe Pro Gly Phe Phe Tyr
                    725                 730                 735

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Leu Gln
                755                 760                 765

Asp Gly Gln Val Lys Ile Ala Pro Thr Val Ile Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
                820                 825                 830

Ile Glu Ser Ala Leu Glu Leu Ser Ala Arg Leu Glu Ser Val Glu Val
                835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Ser Glu Ser Gly Arg Val His Glu Arg Ser Phe
                885                 890                 895

Ile Glu Asp Leu Leu Phe Asn Lys Xaa Val Thr Asn Gly Leu Gly Thr
                900                 905                 910

Val Asp Glu Asp Tyr Lys Arg Cys Ser Asn Gly Arg Ser Val Ala Asp
                915                 920                 925

Leu Val Cys Ala Gln Tyr Tyr Ser Gly Ile Met Val Leu Pro Gly Val
                930                 935                 940

Val Asp Ala Glu Lys Leu His Met Tyr Ser Ala Ser Leu Ile Gly Gly
945                 950                 955                 960

Met Ala Leu Gly Gly Phe Thr Ala Ala Val Ala Leu Pro Phe Ser Tyr
                965                 970                 975

Ala Val Gln Ala Arg Leu Asn Tyr Leu Ala Leu Gln Thr Asp Val Leu
                980                 985                 990

Gln Arg Asn Gln Gln Leu Leu Ala Glu Ser Phe Asn Ser Ala Ile Gly
                995                 1000                1005

Ser Ile Thr Ser Ala Phe Glu Ser Val Asn Glu Ala Ile Ser Gln
    1010                1015                1020

Thr Ser Lys Gly Leu Asn Thr Val Ala His Ala Leu Thr Lys Val
    1025                1030                1035

Gln Glu Val Val Asn Ser Gln Gly Ser Ala Leu Thr Gln Leu Thr
    1040                1045                1050

Ile Gln Leu Gln His Asn Phe Gln Ala Ile Ser Ser Ser Ile Asp
    1055                1060                1065

Asp Ile Tyr Ser Arg Leu Asp Ile Leu Ser Ala Asp Val Gln Val
    1070                1075                1080

Asp Arg Leu Ile Thr Gly Arg Leu Ser Ala Leu Asn Ala Phe Val
    1085                1090                1095

Ala Gln Thr Leu Thr Lys Tyr Thr Glu Val Gln Ala Ser Arg Lys
    1100                1105                1110

Leu Ala Gln Gln Lys Val Asn Glu Cys Val Lys Ser Gln Ser Gln
    1115                1120                1125
```

```
Arg Tyr Gly Phe Cys Gly Gly Asp Gly Glu His Ile Phe Ser Leu
    1130            1135                1140

Val Gln Ala Ala Pro Gln Gly Leu Leu Phe Leu His Thr Val Leu
    1145            1150                1155

Val Pro Gly Asp Phe Val Asn Val Ile Ala Ile Ala Gly Leu Cys
    1160            1165                1170

Val Asn Gly Asp Ile Ala Leu Thr Leu Arg Glu Pro Gly Leu Val
    1175            1180                1185

Leu Phe Thr His Glu Leu Gln Thr His Thr Ala Thr Glu Tyr Phe
    1190            1195                1200

Val Ser Ser Arg Arg Met Phe Glu Pro Arg Lys Pro Thr Val Ser
    1205            1210                1215

Asp Phe Val Gln Ile Gln Ser Cys Val Val Thr Tyr Val Asn Leu
    1220            1225                1230

Thr Ser Asp Gln Leu Pro Asp Val Ile Pro Asp Tyr Val Asp Val
    1235            1240                1245

Asn Lys Thr Leu Asp Glu Ile Leu Ala Ser Leu Pro Asn Arg Thr
    1250            1255                1260

Gly Pro Asn Leu Pro Leu Asp Val Phe Asn Ala Thr Tyr Leu Asn
    1265            1270                1275

Leu Thr Gly Glu Ile Ala Asp Leu Glu Gln Arg Ser Glu Ser Leu
    1280            1285                1290

Arg Asn Thr Thr Glu Glu Leu Arg Ser Leu Ile Tyr Asn Ile Asn
    1295            1300                1305

Asn Thr Leu Val Asp Leu Glu Trp Leu Asn Arg Val Glu Thr Tyr
    1310            1315                1320

Ile Lys Trp Pro Trp Trp Val Trp Leu Ile Val Phe Ile Val Leu
    1325            1330                1335

Ile Phe Val Val Ser Leu Leu Val Phe Cys Cys Ile Ser Thr Gly
    1340            1345                1350

Cys Cys Gly Cys Cys Gly Cys Cys Gly Ala Cys Phe Ser Gly Cys
    1355            1360                1365

Cys Arg Gly Pro Arg Leu Gln Pro Tyr Glu Ala Phe Glu Lys Val
    1370            1375                1380

His Val Gln
    1385

<210> SEQ ID NO 23
<211> LENGTH: 1382
<212> TYPE: PRT
<213> ORGANISM: Porcine epidemic diarrhea virus

<400> SEQUENCE: 23

Met Thr Pro Leu Ile Tyr Phe Trp Leu Phe Leu Pro Val Leu Leu Thr
1               5                   10                  15

Leu Ser Leu Pro Gln Asp Val Thr Arg Cys Gln Ser Thr Ile Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ser Met Asn Ser Ser Ser Trp Tyr Cys Gly
        50                  55                  60

Thr Gly Ile Glu Thr Asp Ser Gly Val His Gly Ile Phe Leu Ser Tyr
65                  70                  75                  80

Ile Asp Ser Gly Gln Gly Phe Glu Ile Gly Ile Ser Gln Glu Pro Phe
```

-continued

```
                    85                  90                  95
Asp Pro Ser Gly Tyr Gln Leu Tyr Leu His Lys Ala Thr Asn Gly Asn
                100                 105                 110
Thr Ser Ala Ile Ala Arg Leu Arg Ile Cys Gln Phe Pro Asp Asn Lys
            115                 120                 125
Thr Leu Gly Pro Thr Val Asn Asp Val Thr Thr Gly Arg Asn Cys Leu
        130                 135                 140
Phe Asn Lys Ala Ile Pro Ala Leu Gln Asp Gly Lys Asn Ile Val Val
145                 150                 155                 160
Gly Ile Thr Trp Asp Asn Asp Arg Val Thr Val Phe Ala Asp Lys Ile
                165                 170                 175
Tyr His Phe Tyr Ile Lys Asn Asp Trp Ser Arg Val Ala Thr Arg Cys
            180                 185                 190
Tyr Asn Lys Arg Ser Cys Ala Met Gln Tyr Val Tyr Thr Pro Thr Tyr
        195                 200                 205
Tyr Met Leu Asn Val Thr Ser Ala Gly Glu Asp Gly Ile Tyr Tyr Glu
    210                 215                 220
Pro Cys Thr Ala Asn Cys Ser Gly Tyr Ala Ala Asn Val Phe Ala Thr
225                 230                 235                 240
Asp Ser Asn Gly His Ile Pro Glu Gly Phe Ser Phe Asn Asn Trp Phe
                245                 250                 255
Leu Leu Ser Asn Asp Ser Thr Leu Leu His Gly Lys Val Val Ser Asn
            260                 265                 270
Gln Pro Leu Leu Val Asn Cys Leu Arg Ala Ile Pro Lys Ile Tyr Gly
        275                 280                 285
Leu Gly Gln Phe Phe Ser Phe Asn Gln Thr Met Asp Gly Val Cys Asn
    290                 295                 300
Gly Ala Ala Ala Gln Arg Ala Pro Glu Ala Leu Arg Phe Asn Ile Asn
305                 310                 315                 320
Asp Thr Phe Val Ile Leu Ala Glu Gly Ser Ile Val Leu His Thr Ala
                325                 330                 335
Leu Gly Thr Asn Leu Ser Phe Val Cys Ser Asn Ser Ser Asp Pro His
            340                 345                 350
Lys Ala Ile Phe Thr Ile Pro Leu Gly Val Thr Glu Val Pro Tyr Tyr
        355                 360                 365
Cys Phe Leu Lys Val Asp Thr Tyr Lys Ser Thr Val Tyr Lys Phe Leu
    370                 375                 380
Ala Val Leu Pro Pro Thr Val Lys Glu Ile Val Ile Thr Lys Tyr Gly
385                 390                 395                 400
Asp Val Tyr Val Asn Gly Phe Gly Tyr Leu His Leu Gly Leu Leu Asp
                405                 410                 415
Ala Val Thr Ile Asn Phe Thr Gly His Gly Thr Asp Asp Asp Val Ser
            420                 425                 430
Gly Phe Trp Thr Val Ala Ser Thr Asn Phe Val Asp Ala Leu Ile Glu
        435                 440                 445
Val Gln Gly Thr Ala Ile Gln Arg Ile Leu Tyr Cys Asp Asp Pro Val
    450                 455                 460
Ser Gln Leu Lys Cys Ser Gln Val Ser Phe Asp Leu Asp Gly Phe Tyr
465                 470                 475                 480
Tyr Pro Ile Ser Ser Arg Asn Leu Leu Ser His Glu Gln Pro Ile Ser
                485                 490                 495
Phe Val Thr Leu Pro Ser Phe Asn Asp His Ser Phe Val Asn Ile Thr
            500                 505                 510
```

```
Val Ser Ala Ala Phe Gly Gly His Ser Gly Ala Asn Leu Ile Ala Ser
    515                 520                 525

Asp Thr Thr Asn Gly Phe Ser Ser Phe Cys Val Asp Thr Arg Gln
    530                 535                 540

Phe Thr Ile Thr Leu Phe Tyr Asn Val Thr Asn Ser Tyr Gly Tyr Val
545                 550                 555                 560

Ser Lys Ser Gln Asp Ser Asn Cys Pro Phe Thr Leu Gln Ser Val Asn
                565                 570                 575

Asp Tyr Leu Ser Phe Ser Lys Phe Cys Val Ser Thr Ser Leu Leu Ala
            580                 585                 590

Gly Ala Cys Thr Ile Asp Leu Phe Gly Tyr Pro Glu Phe Gly Ser Gly
        595                 600                 605

Val Lys Phe Thr Ser Leu Tyr Phe Gln Phe Thr Lys Gly Glu Leu Ile
    610                 615                 620

Thr Gly Thr Pro Lys Pro Leu Gln Gly Val Thr Asp Val Ser Phe Met
625                 630                 635                 640

Thr Leu Asp Val Cys Thr Lys Tyr Thr Ile Tyr Gly Phe Lys Gly Glu
                645                 650                 655

Gly Ile Ile Thr Leu Thr Asn Ser Ser Phe Leu Ala Gly Val Tyr Tyr
            660                 665                 670

Thr Ser Asp Ser Gly Gln Leu Leu Ala Phe Lys Asn Val Thr Ser Gly
        675                 680                 685

Ala Val Tyr Ser Val Thr Pro Cys Ser Phe Ser Glu Gln Ala Ala Tyr
    690                 695                 700

Val Asp Asp Asp Ile Val Gly Val Ile Ser Ser Leu Ser Asn Ser Thr
705                 710                 715                 720

Phe Asn Asn Thr Arg Glu Leu Pro Gly Phe Phe Tyr His Ser Asn Asp
                725                 730                 735

Gly Ser Asn Cys Thr Glu Pro Val Leu Val Tyr Ser Asn Ile Gly Val
            740                 745                 750

Cys Lys Ser Gly Ser Ile Gly Tyr Val Pro Leu Gln Asp Gly Gln Val
        755                 760                 765

Lys Ile Ala Pro Met Val Thr Gly Asn Ile Ser Ile Pro Thr Asn Phe
    770                 775                 780

Ser Met Ser Ile Arg Thr Glu Tyr Leu Gln Leu Tyr Asn Thr Pro Val
785                 790                 795                 800

Ser Val Asp Cys Val Thr Tyr Val Cys Asn Gly Asn Ser Arg Cys Lys
                805                 810                 815

Gln Leu Leu Thr Gln Tyr Thr Ala Ala Cys Lys Thr Ile Glu Ser Ala
            820                 825                 830

Leu Gln Leu Ser Ala Arg Leu Glu Ser Val Glu Val Asn Ser Met Leu
        835                 840                 845

Thr Ile Ser Glu Glu Ala Leu Gln Leu Ala Thr Ile Ser Ser Phe Asn
    850                 855                 860

Gly Asp Gly Tyr Asn Phe Thr Asn Val Leu Gly Val Ser Val Tyr Asp
865                 870                 875                 880

Pro Ala Ser Gly Arg Val Val Gln Lys Gly Ser Phe Ile Glu Asp Leu
                885                 890                 895

Leu Phe Asn Lys Val Val Thr Asn Gly Leu Gly Thr Val Asp Glu Asp
            900                 905                 910

Tyr Lys Arg Cys Ser Asn Gly Arg Ser Val Ala Asp Leu Val Cys Ala
        915                 920                 925
```

```
Gln Tyr Tyr Ser Gly Val Met Val Leu Pro Gly Val Val Asp Ala Glu
        930                 935                 940

Lys Leu His Met Tyr Ser Ala Ser Leu Leu Gly Gly Met Ala Leu Gly
945                 950                 955                 960

Gly Leu Thr Thr Ala Ala Ala Leu Pro Phe Ser Asn Ala Val Gln Ala
                965                 970                 975

Arg Leu Asn Tyr Leu Ala Leu Gln Thr Asp Val Leu Gln Arg Asn Gln
            980                 985                 990

Gln Leu Leu Ala Glu Ser Phe Asn Ser Ala Ile Gly Asn Ile Thr Ser
        995                1000                1005

Ala Phe Glu Ser Val Lys Glu Ala Ile Ser Gln Thr Ser Asn Gly
   1010                1015                1020

Leu Asn Thr Val Ala His Ala Leu Thr Lys Val Gln Glu Val Val
   1025                1030                1035

Lys Ser Gln Gly Ser Ala Leu Thr Gln Leu Thr Ile Gln Leu Gln
   1040                1045                1050

His Asn Phe Gln Ala Ile Ser Ser Ser Ile Asp Asp Ile Tyr Ser
   1055                1060                1065

Arg Leu Asp Ile Leu Ser Ala Asp Val Gln Val Asp Arg Leu Ile
   1070                1075                1080

Thr Gly Arg Leu Ser Ala Leu Asn Ala Phe Val Ala Gln Thr Leu
   1085                1090                1095

Thr Lys Tyr Thr Glu Val Gln Ala Ser Arg Lys Leu Ala Gln Gln
   1100                1105                1110

Lys Val Asn Glu Cys Val Lys Ser Gln Ser Gln Arg Tyr Gly Phe
   1115                1120                1125

Cys Gly Gly Asp Gly Glu His Ile Phe Ser Leu Val Gln Ala Ala
   1130                1135                1140

Pro Gln Gly Leu Leu Phe Leu His Thr Val Leu Val Pro Gly Asp
   1145                1150                1155

Phe Val Asn Val Ile Ala Ile Asp Gly Leu Cys Val Asn Gly Asp
   1160                1165                1170

Ile Ala Leu Thr Leu Arg Glu Pro Gly Leu Val Leu Phe Thr His
   1175                1180                1185

Glu Leu Gln Thr Tyr Thr Ala Thr Glu Tyr Phe Val Ser Ser Arg
   1190                1195                1200

Arg Met Phe Glu Pro Arg Lys Pro Thr Val Ser Asp Phe Val Gln
   1205                1210                1215

Ile Glu Ser Cys Val Val Thr Tyr Val Asn Leu Thr Ser Asp Gln
   1220                1225                1230

Leu Pro Asp Val Ile Pro Asp Tyr Ile Asp Val Asn Lys Thr Leu
   1235                1240                1245

Asp Glu Ile Leu Ala Ser Leu Pro Asn Arg Ile Gly Pro Ser Leu
   1250                1255                1260

Pro Leu Asp Val Phe Asn Ala Thr Tyr Leu Asn Leu Thr Gly Glu
   1265                1270                1275

Ile Ala Asp Leu Glu Gln Arg Ser Glu Ser Leu Arg Asn Thr Thr
   1280                1285                1290

Glu Glu Leu Arg Ser Leu Ile Tyr Asn Ile Asn Asn Thr Leu Val
   1295                1300                1305

Asp Leu Glu Trp Leu Asn Arg Val Glu Thr Tyr Ile Lys Trp Pro
   1310                1315                1320

Trp Trp Val Trp Leu Ile Ile Phe Ile Val Leu Ile Phe Val Val
```

```
                  1325                1330                1335

Ser Leu Leu Val Phe Cys Cys Ile Ser Thr Gly Cys Cys Gly Cys
        1340                1345                1350

Cys Gly Cys Cys Gly Ala Cys Phe Ser Gly Cys Cys Arg Gly Pro
        1355                1360                1365

Arg Leu Gln Pro Tyr Glu Ala Phe Glu Lys Val His Val Gln
        1370                1375                1380

<210> SEQ ID NO 24
<211> LENGTH: 4
<212> TYPE: PRT
<213> ORGANISM: Artificial Sequence
<220> FEATURE:
<223> OTHER INFORMATION: Endoplasmic reticulum signal sequence

<400> SEQUENCE: 24

His Asp Glu Leu
1

<210> SEQ ID NO 25
<211> LENGTH: 2217
<212> TYPE: DNA
<213> ORGANISM: Artificial Sequence
<220> FEATURE:
<223> OTHER INFORMATION: Synthetic construct

<400> SEQUENCE: 25
atggcgaaca agcacctgag ccttagcctc ttcctcgtgc tcctgggcct ctcgcctcc        60 ctcgcctccg gcgtcactcg ctgccagtcg accatcaact tccgcaggtt cttctccaag      120
ttcaacgtgc aggccccgc ggtggtggtg ctcggcggct acctgccctc catgaattct       180
agctcctggt actgcggcac gggcatcgag acggactcgg gcgtgcacgg catcttcctc      240
agctacatcg actccggcca gggcttcgag atcggcatct cgcaggagcc cttcgaccca      300
tcgggctacc agtctacct gcacaaggcc accaacggca cacgaacgc gatcgcccgc       360 ctcaggatct gccagttccc ggacaacaag accctgggcc caaccgtcaa cgacgtgacc     420
accggccgca actgcctgtt caacaaggcg atcccgcct acctccagga cggcaagaac      480
atcgtcgtgg gcatcacgtg ggacaacgac agggtcaccg tgttcgcgga caagatctac     540
cacttctacc tcaagaacga ctggtcccgc gtcgcgacca ggtgctacaa caagcgcagc    600
tgcgccatgc agtatgtgta cacccccgacg tactacatgc tcaacgtgac ctcggcgggc    660
gaggacggca tctactacga gccgtgcacg gccaactgct cgggctacgc ggccaacgtg     720
ttcgctaccg actccaacgg ccacatcccg gagggcttca gcttcaacaa ctggttcctc     780
ctgagcaacg actccaccct cctgcacggc aagtcgtgt ccaaccagcc gctcctggtc     840
aactgcctcc tggcgatccc caagatctac ggcctgggcc agttcttcag cttcaaccag    900
acgatggacg cgtgtgcaa cggcgcggc gctcagaggg ccccgaggc cctcaggttc       960 aacatcaacg acacgagcgt catcctggcc gagggctcca tcgtgctcca cacggctctg    1020
ggcacgaacc tcagcttcgt gtgctccaac agctccgacc cccacctggc catcttcgct    1080 atcccctgg gcgccacgga ggtccccta ctactgcttcc tgaaggtgga cacctacaac    1140
agcacggtct acaagttcct ggcggtgctg ccgcccacgg tcagggagat cgtgatcacc    1200
aagtacggcg acgtctacgt gaacggcttc ggctacctcc acctgggcct cctggacgcg    1260
gtcaccatca acttcaccgg ccacggcacg gacgacgacg tgagcggctt ctggacgatc    1320
gcgagcacca acttcgtgga cgctctcatc gaggtgcagg gcaccgcgat ccagaggatc    1380
```

```
ctgtactgcg acgacccggt cagccagctc aagtgctccc aggtggcctt cgacctggac    1440
gacggcttct accccatcag ctcccgcaac ctcctgagcc acgagcagcc gatctccttc    1500
gtcaccctgc ccagcttcaa cgaccactcc ttcgtcaaca tcacggtgag cgccgctttc    1560
ggtggccact cgggcgccaa cctcatcgct tccgacacca cgatcaacgg cttcagctcc    1620
ttctgcgtgg acacgcgcca gttcaccatc acgctgttct acaacgtcac caactcctac    1680
ggctacgtga gcaagtccca ggactccaac tgcccgttca ccctgcagag cgtcaacgac    1740
tacctcagct tctccaagtt ctgcgtgagc acgtccctcc tggccggcgc ttgcaccatc    1800
gacctcttcg gctaccccga gttcggcagc ggcgtcaagt tcacgtccct gtacttccag    1860
ttcaccaagg gcgagctgat cacgggcacc cccaagccac tggagggcgt cacggacgtg    1920
agcttcatga ccctcgacgt gtgcaccaag tacacgatct acggcttcaa gggcgagggc    1980
atcatcaccc tgacgaactc aagctttctc gccggcgtct actacaccag cgactccggc    2040
cagctcctgg cgttcaagaa cgtgacctcg ggcgcggtct actcggtgac gccctgcagc    2100
ttctccgagc aggccgccta cgtggacgac gacatcgtcg gcgtgatcag ctccctgagc    2160
aactcaacat tcaacaacac tcgggagctg cctggcttct tctaccattc ctgatag      2217
```

EXPRESSION OF PEDV SEQUENCES IN PLANTS AND PLANT PRODUCED VACCINE FOR SAME

CROSS-REFERENCE TO RELATED APPLICATION

This application claims the benefit of previously filed and co-pending application U.S. Ser. No. 62/730,045, filed Sep. 12, 2018, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Sep. 4, 2019 is named HOWARD_P12620US01_SEQ_LISTING_09-04-19_ST25.TXT and is 130,441 bytes in size.

SUMMARY

A vaccine for Porcine Epidemic Diarrhea Virus (PEDV) is provided which is produced from a plant. A construct is introduced into a plant comprising a promoter preferentially directing expression to seed of the plant, a nucleic acid molecule encoding a Spike polypeptide of PEDV and a nucleic acid molecule targeting expression to the endoplasmic reticulum. Embodiments provide the construct comprises a sequence of the COE polypeptide, a sequence encoding the LTB heat labile polypeptide or a combination thereof. Expression levels of at least 10 mg/kg of seed of the plant are obtained. When the plant or plant product is orally administered to the animal, a protective response is observed, including a serum antibody response.

BACKGROUND

Figure 1:
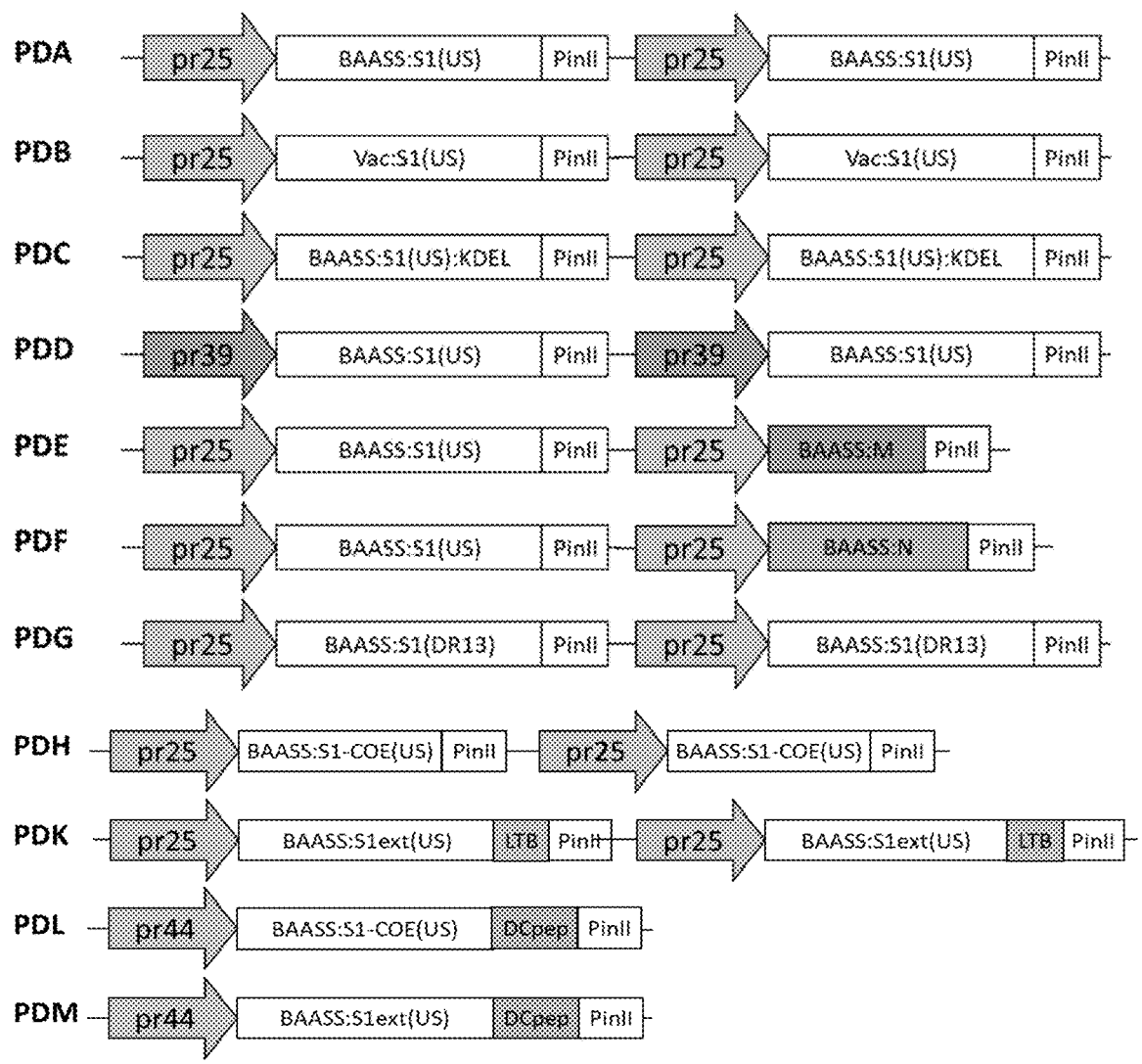
FIG. 1 is a graphic showing constructs created for introduction into plants. Promoters used were pr25, pr39 and pr44. BAASS refers to the barley alpha amylase sequence, S1 refers to the US strain spike proteins where S1ext(US) refers to an extended sequence and S1(DR13) refers to a South Korean strain spike protein; Vac refers to a vaculose targeting sequence, KDEL refers to an endoplasmic reticulum retaining sequence; COE refers to the COE sequence; PinII is the PinII terminator and LTB refers to the heat labile enterotoxin subunit, all of which are described in further detail here.

The porcine epidemic diarrhea virus is an enveloped, positive-sense single-stranded RNA virus that causes acute diarrhea, vomiting, and dehydration in pigs. It was first identified in Europe but has become increasingly problematic in many Asian countries, including Korea, China, Japan, the Philippines, and Thailand. In April of 2013, PEDV emerged in U.S. swine in the Midwest, swiftly spreading across the country. By October 2013, PEDV was detected in swine herds in 18 States. The economic impact of PEDV infection has already been substantial. North American isolates of PEDV have been identified (Huang, et al. 2013; Stevenson et al. 2013), however no fully licensed vaccine is commercially available in the United States. Accordingly, there is a continuing need to develop vaccines capable of protecting pigs against disease associated with PEDV.

DESCRIPTION

Porcine Epidemic Diarrhea Virus (PEDV) is a member of the subfamily Coronavirinae of genus Alphacoronavirus (Bridgen et al. 1993 Sequence determination of the nucleocapsid protein gene of the porcine epidemic diarrhoea virus confirms that this virus is a coronavirus related to human coronavirus 229E and porcine transmissible gastroenteritis virus. J. Gen. Virol. 74 (Pt 9):1795-1804) and was first identified in England in 1971 and later in other countries, such as Belgium, China, Hungary, Italy, Japan, Korea, and Thailand (Oldham J. 1972 Letter to the editor. Pig Farming 1972 (October suppl):72-73; Pensaert and De Bouck P. 1978 A new coronavirus-like particle associated with diarrhoea in swine. Arch. Virol. 58:243-247; Molecular characterization and phylogenetic analysis of membrane protein genes of porcine epidemic diarrhea virus isolates in China. Virus Genes 36:355-364; Nagy et al. 1996. Enterotoxigenic *Escherichia coli*, rotavirus, porcine epidemic diarrhea virus, adenovirus and calici-like virus in porcine postweaning diarrhoea in Hungary. Acta Vet. Hung. 44:9-19; Martelli et al. 2008. Epidemic of diarrhoea caused by porcine epidemic diarrhoea virus in Italy. Vet. Rec. 162:307-310; Takahashi et al. 1983. An outbreak of swine diarrhea of a new-type associated with coronavirus-like particles in Japan. Nippon Juigaku Zasshi 45:829-832; Chae et al. 2000. Prevalence of porcine epidemic diarrhoea virus and transmissible gastroenteritis virus infection in Korean pigs. Vet. Rec. 147:606-608; Puranavej a et al. 2009. Chinese-like strain of porcine epidemic diarrhea virus, Thailand. Emerg. Infect. Dis. 15:1112-1115). Other members of this family include Porcine Respiratory Coronavirus (PRCV), Hemagglutinating Encephalomyelitis Coronavirus (PHE), and Transmissible Gastroenteritis Virus (TGEV). Although PEDV and TGEV viruses are related and the clinical signs are very similar, there is no immune cross-protection.

PEDV is an enveloped virus possessing approximately a 28 kb, positive-sense, single stranded RNA genome, with a 5' cap and a 3' polyadenylated tail. (Pensaert and De Bouck P. 1978). The genome comprises a 5' untranslated region (UTR), a 3' UTR, and at least seven open reading frames (ORFs) that encode four structural proteins (spike (S), envelope (E), membrane (M), and nucleocapsid (N)) and three non-structural proteins (replicases 1a and 1b and ORF3); these are arranged on the genome in the order 5'-replicase (1a/1b)-S-ORF3-E-M-N-3' (Oldham J. 1972; and Bridgen et al. 1993). The first three emergent North American PEDV genomic sequences characterized, Minnesota MN (GenBank: KF468752.1), Iowa IA1 (GenBank: KF468753.1), and Iowa IA2 (GenBank: KF468754.1), have the same size of 28,038 nucleotides (nt), excluding the polyadenosine tail and share the genome organization with the prototype PEDV CV777 strain (GenBank: AF353511.1). These three North American PEDV sequences shared 99.8 to 99.9% nucleotide identities. In particular, strains MN and IA2 had only 11 nucleotide differences across the entire genome.

The PEDV Spike (S) protein is a type I glycoprotein composed of about 1,383 amino acids (aa) (1386 with the Korea strain, see e.g., GenBank Ref NO. AAM19716.1 (SEQ ID NO: 22), identifying the S1 region as residues 234-736; 1382 amino acids in a China strain, with S1 identified as 230-732, see GenBank Ref No. AFL02627.1 (SEQ ID NO: 23)). It contains a putative signal peptide (residues 1-24). The S protein can be divided into two regions. One is the N-terminal region of S1 (1-733 or 735 aa). Referring to the Spike protein used in the example below, it has 94% identity to Korean strain example of AAM19716.1 and 93% identity with the China strain example of AFL02627.1. The other region is the C-terminal region S2 which is identified as including residues 736-741 to the end of the Spike protein based on its homology with S protein of other coronaviruses (Chang et al. 2002 Identification of the epitope region capable of inducing neutralizing antibodies against the porcine epidemic diarrhea virus. Mol. Cells 14, 295-299. Cleavage of the spike protein into S1 and S2 can occur in the presence of trypsin. (See e.g., Wicht et al. (2014) Proteolytic activation of the porcine epidemic diarrhea coronavirus spike fusion protein by trypsin in cell culture. J. Virol. 88:2952-7961). The GPRLQPY motif located at the carboxy-terminal of the spike protein induces antibodies that neutralize Porcine epidemic diarrhea virus. Godet et al. 1994 Virus Res. 132, 192-196. Major receptor-binding and neutralization determinants are located within the same domain of the transmissible gastroenteritis virus (coronavirus) spike protein. J. Virol. 68, 8008-8016; Jackwood et al. 2001. Spike glycoprotein cleavage recognition site analysis of infectious bronchitis virus. Avian Dis. 45, 366-372; Sturman et al. 1984 Proteolytic cleavage of peplomeric glycoprotein E2 of MHV yields two 90K subunits and activates cell fusion. Adv. Exp. Med. Biol. 173, 25-35. 33; Sun et al. 2008. Identification of two novel B cell epitopes on porcine epidemic diarrhea virus spike protein. Vet. Microbiol. 131, 73-81. 34). The S protein in coronaviruses is a surface antigen, where it plays a role in regulating interactions with host cell receptor glycoproteins to mediate viral entry and stimulating induction of neutralizing antibodies in the natural host. A phylogenetic and genetic comparison analysis of the S gene and its regions showed minor variations among strains, including the US, China, Korea, showed a percent identity ranging from 89.4% to 100% identity. This included percent identity of comparison of strains DR13, BM1, J3142, BM3, CV777, AH2012, BJ-2012-2, Colorado30, Indiana34 and Texas 31. See Chung et al (2017) Genetic characterization of S1 domain of porcine epidemic diarrhea viruses spike proteins isolated in Korea, J. Immune Disord. Vol. 1 No. 1. Sequence comparisons of the polypeptide of the S protein showed Korean isolates had 93.6% to 99.6% identity with each other and 92.2%-93.7% identity with other strains. Lee et al. (2010) Hetergeneity in spike protein genes of porcine epidemic diarrhea viruses isolate din Kore, Virus Res. 149(2): 175-82. Thus, the S glycoprotein is a primary target for the development of effective vaccines against PEDV.

The PEDV M protein is the most abundant envelope component playing an important role in the viral assembly process and also induces antibodies that neutralize the virus. Likewise, the PEDV N protein, which binds to virion RNA providing a structural basis for the nucleocapsid, may also be important for induction of cell-mediated immunity (Saif, L. 1993 Coronavirus immunogens. Vet. Microbiol. 285-297).

The only accessory gene in PEDV is ORF3. While accessory genes are generally maintained in field strains, alteration of ORF3 is thought to influence virulence; cell culture adaptation has been used to alter the ORF3 gene in order to reduce virulence (Song et al. 2003 Differentiation of a Vero cell adapted porcine epidemic diarrhea virus from Korean field strains by restriction fragment length polymorphism analysis of ORF 3. Vaccine 21, 1833-1842). In fact, through investigation of the ORF3 gene, researchers have charted the emergence of new genogroups of PEDV in immunized swine herds in China since 2006. Phylogenic studies of these strains and the geographical reemergence of PEDV in China have demonstrated that those field strains causing devastating enteric disease differ genetically in ORF3 from the European strains and vaccine strains (Park et al. 2011) Molecular characterization and phylogenetic analysis of porcine epidemic diarrhea virus (PEDV) field isolates in Korea. Arch. Virol. 156, 577-585.

Different strains of PEDV exist with varying levels of virulence. The clinical signs of PEDV infection are similar to transmissible gastroenteritis virus (TGEV) infection (Pijpers et al. 1993). In pigs three weeks of age and younger, clinical signs (including acute watery, diarrhea, vomiting, and dehydration) can be seen as soon as 24 hours after PEDV infection leading to 100% mortality. PEDV-infected feeder and grower pigs, as well as sows and boars, can develop diarrhea and vomiting. The animals can also show signs of anorexia and can be lethargic. Older pigs show reduced feed efficiency, additional days to market, and the susceptibility of infected animals to secondary infections is likely. For sows, reduced body condition may negatively impact reproductive performance.

The gross and histological changes in the gut of animals infected with PEDV are similar in the United States as those observed in China; essentially the virus destroys the villi of a pig's intestine so that there is a failure to absorb nutrients. Animals succumbing to the disease in the Minnesota and Iowa outbreaks had gross pathological lesions confined to the small intestine and that the small intestine was characterized by thin translucent walls distended with yellow fluid. Histological evaluations revealed regions of small intestines with villus blunting and fusion and minimal lymphoblastic infiltration of the villi of the lamia propria.

Huang et al. 2013 characterized three different strains of PEDV from outgoing outbreaks in the United States—one from Minnesota and two from Iowa, designated MN (GenBank accession No: KF468752) and IA1 (GenBank accession No: KF468753) and IA2 (GenBank accession No: KF48754), respectively. (Huang et al. 2013 Origin, evolution, and genotyping of emergent porcine epidemic diarrhea virus strains in the United States. mBio 4(5):e00737-13.) Huang's phylogenic survey grouped PEDV strains as falling into two distinct genogroups, designated genogroup 1 (G1) and genogroup 2 (G2). Genogroup 1 includes at least three clusters 1a, 1b, and R. Subgroup 1a includes the early European, Chinese, and Korean isolates, e.g., prototype CV777 strain (Belgium, 1978, GenBank: AF353511.1) and strains LZC (Gansu, China, 2006; GenBank: EF185992) and SM98 (Korea, 1998; GenBank: GU937797.1). Subgroup 1b contains five strains—one from South Korea (the DR13 attenuated vaccine strain, GenBank: JQ023162.1) and the others from China linked by the common "genetic signature" 8-aa deletion in nsp3 and the large ORF3 deletion at the C terminus. Group "R" is associated with recombinants of the other genogroups. Certain strains belong to genogroup G2a. The Chinese strain AH2012 (GenBank accession no: KC210145) and the North American strains share several unique nucleotides changes and are clustered together in genogroup 2a. Nucleotide identity to AH2012 for strains MN and IA2 was 99.6% and for strain IA1 was 99.5%. A closely related North American isolate US/Colorado/2013 (GenBank Accession No: KF272920.1) has also been reported by Marthaler et al, 2013 Complete genome sequence of porcine epidemic diarrhea virus strain USA/Colorado/2013 from the United States. Genome Announc. 1(4):e00555-13.10.1128/genomeA.00555-13. Like the North American isolates above, the complete PEDV genome of CO/13 has a nucleotide identity of 96.5 to 99.5% with other complete PEDV genomes available in GenBank, with the highest nucleotide identity (99.5%) with Chinese strain AH2012 (GenBank Accession No. KC210145). It is a member of the 2a genogroup.

Attempts to create PEDV vaccines include production of attenuated viral vaccines, such as that described at U.S. Pat. No. 9,950,061, incorporated by reference in its entirety. The attenuated vaccine included a Spike antigen, with that modified Spike protein shown as sequence identifier 9, encoded by the nucleic acid of sequence identifier 8 with variations effective for protection shown having at least 80% homology and included sequence identifiers 3, 7, 9 and 14, all of which are incorporated by reference herein in their entirety.

Here is provided a plant-produced Spike (S) polypeptide and a vaccine for PEDV comprising the same. In an embodiment the S polypeptide is introduced into a plant in a construct comprising a seed-preferred promoter which may further prefer expression to the embryo of the seed, operably linked to the nucleic acid molecule encoding the S polypeptide. In further embodiments the construct comprises nucleic acid molecules that retain expression of the S polypeptide in the endoplasmic reticulum of the cell of the plant. Still further embodiments provide for two plant transcription units (PTUs) with each PTU comprising an embryo preferred promoter and nucleic acid molecules retaining expression in the endoplasmic reticulum. Additional embodiments provide the PTUs comprises the same seed preferred promoter and nucleic acid molecules retaining expression in the endoplasmic reticulum.

The S protein is expressed poorly in recombinant systems, therefore, it is difficult to develop a commercial subunit vaccine. Here in an embodiment, maize grain is used as a basis for the production of the subunit vaccine. High expression levels of at least 10 mg/kg of whole seed are obtained. An embodiment provides for a range of about 10-100 mg/kb. Further embodiments provide for expression at 11 mg/kb, 12 mg/kg, 13, 14, 15, 16, 17, 18, 19, 20, 25, 30, 35, 40 mg/kg of whole seed or more or amounts in-between.

Further, oral administration of the plant, plant part or a product produced from the plant part, such as a seed, grain, flour or other edible composition comprising the plant, plant part or product produced therefrom comprising the Spike protein results in surprising serum response from animals, and can also produce a mucosal response as well. The serum response in an embodiment is within the range of two—100 fold more than the control. In another embodiment the response can be 5 times, 10 times, 15 times, 20 times, 25 times, 30 times, 35 times, 40 times, 45 times, 50 times, 55 times, 60 times, 65 times, 70 times, 75 times, 80 times, 85 times, 90 times, 95 times or more greater than control animals not receiving vaccination, or amounts in-between.

As used herein, the terms nucleic acid or polynucleotide refer to deoxyribonucleotides or ribonucleotides and polymers thereof in either single- or double-stranded form. The sequence used to make the vaccine may be obtained from any source, such as a biological source in isolating from a biological sample or can refer to a sequence synthetically produced based upon the sequence obtained from the sample. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene.

Nucleic acids employed here include those that encode an entire polypeptide as well as those that encode a subsequence of the polypeptide or produce a fragment that provides a protective response. For example, nucleic acids that encode a polypeptide which is not full-length but nonetheless has protective activity against PEDV. The invention includes not only nucleic acids that include the nucleotide sequences as set forth herein, but also nucleic acids that are substantially identical to, correspond to, or substantially complementary to, the exemplified embodiments. For example, the invention includes nucleic acids that include a nucleotide sequence that is at least about 70% identical to one that is set forth herein, more preferably at least 75%, still more preferably at least 80%, more preferably at least 85%, 85.5% 86%, 86.5% 87%, 87.5% 88%, 88.5%, 89%, 89.5% still more preferably at least 90%, 90.5%, 91%, 91.5% 92%, 92.5%, 93%, 94.5%, 94%, 94.5% and even more preferably at least about 95%, 95.5%, 96%, 96.5%, 97%, 97.5%, 98%, 98.5%, 99%, 95.5%, 100% identical (or any percentage in between) to an exemplified nucleotide sequence. The nucleotide sequence may be modified as described previously, so long as any polypeptide encoded produced is capable of inducing the generation of a protective response.

The nucleic acids can be obtained using methods that are known to those of skill in the art. Suitable nucleic acids (e.g., cDNA, genomic, or subsequences) can be cloned, or amplified by in vitro methods such as the polymerase chain reaction (PCR) using suitable primers, the ligase chain reaction (LCR), the transcription-based amplification system (TAS), or the self-sustained sequence replication system (SSR). A wide variety of cloning and in vitro amplification methodologies are well-known to persons of skill Examples of these techniques and instructions sufficient to direct persons of skill through many cloning exercises are found in Berger and Kimmel, Guide to Molecular Cloning Techniques, Methods in Enzymology 152 Academic Press, Inc., San Diego, Calif. (Berger); Sambrook et al. (2001) Molecular Cloning—A Laboratory Manual (Third ed.) Vol. 1-3, Cold Spring Harbor Laboratory, Cold Spring Harbor Press, NY, (Sambrook et al.); Current Protocols in Molecular Biology, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Amheim & Levinson (Oct. 1, 1990) C& EN 36-47; The Journal Of NIH Research (1991) 3: 81-94; (Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117. Improved methods of cloning in vitro amplified nucleic acids are described in Wallace et al., U.S. Pat. No. 5,426,039. Nucleic acids or subsequences of these nucleic acids, can be prepared by any suitable method as described above, including, for example, cloning and restriction of appropriate sequences.

"Codon optimization" can be used to optimize sequences for expression in an animal and is defined as modifying a nucleic acid sequence for enhanced expression in the cells of the animal of interest, e.g. swine, by replacing at least one, more than one, or a significant number, of codons of the native sequence with codons that are more frequently or most frequently used in the genes of that animal. Various species exhibit particular bias for certain codons of a particular amino acid.

As used herein, a "polypeptide" refers generally to peptides and proteins. In certain embodiments the polypeptide may be at least two, three, four, five, six, seven, eight, nine or ten or more amino acids or more or any amount in-between. A peptide is generally considered to be more than fifty amino acids. The terms "fragment," "derivative" and "homologue" when referring to the polypeptides according to the present invention, means a polypeptide which retains essentially the same biological function or activity as said polypeptide, that is, act as an antigen and/or provide treatment for and/or protection against disease. Such fragments, derivatives and homologues can be chosen based on the ability to retain one or more of the biological activities of the polypeptide, that is, act as an antigen and/or provide treatment for and/or protection against the pathogen. The polypeptide vaccines of the present invention may be recombinant polypeptides, natural polypeptides or synthetic polypeptides, preferably recombinant polypeptides. One skilled in the art appreciates that it is possible that the protective polypeptide may be expressed by the gene in the host cells and the plant composition administered to the animal or extracted from the plant prior to administration.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode a protective polypeptide are preferably optimized for expression in a particular host cell (e.g., yeast, mammalian, plant, fungal, and the like) used to produce the polypeptide or RNA.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994). Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

The isolated variant proteins can be purified from cells that naturally express it, purified from cells that have been altered to express it (recombinant), or synthesized using known protein synthesis methods. For example, a nucleic acid molecule encoding the variant polypeptide is cloned into an expression vector, the expression vector introduced into a host cell and the variant protein expressed in the host cell. The variant protein can then be isolated from the cells by an appropriate purification scheme using standard protein purification techniques. Many of these techniques are described in detail below.

The methods include amino acids that include an amino acid sequence that is at least about 70% identical to one that is set forth herein, more preferably at least 75%, still more preferably at least 80%, more preferably at least 85%, 85.5% 86%, 86.5% 87%, 87.5% 88%, 88.5%, 89%, 89.5% still more preferably at least 90%, 90.5%, 91%, 91.5% 92%, 92.5%, 93%, 94.5%, 94%, 94.5% and even more preferably at least about 95%, 95.5%, 96%, 96.5%, 97%, 97.5%, 98%, 98.5%, 99%, 95.5%, 100% identical (or any percentage in between) to an exemplified nucleotide sequence. The sequence may be modified as described previously, so long the polypeptide is capable of inducing the generation of a protective response.

The variant proteins used in the present methods can be attached to heterologous sequences to form chimeric or fusion proteins. Such chimeric and fusion proteins comprise a variant protein fused in-frame to a heterologous protein having an amino acid sequence not substantially homologous to the variant protein. The heterologous protein can be fused to the N-terminus or C-terminus of the variant protein.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

Polypeptides sometimes contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in polypeptides are described in basic texts, detailed monographs, and the research literature, and they are well known to those of skill in the art. Accordingly, the variant peptides of the present invention also encompass derivatives or analogs in which a substituted amino acid residue is not one encoded by the genetic code, in which a substituent group is included, in which the mature polypeptide is fused with another compound, such as a compound to increase the half-life of the polypeptide (for example, polyethylene glycol), or in which the additional amino acids are fused to the mature polypeptide, such as a leader or secretory sequence or a sequence for purification of the mature polypeptide or a pro-protein sequence.

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The present methods further provide functional fragments of the nucleic acid molecules and polypeptides including variant proteins of the polypeptide, in addition to proteins and peptides that comprise and consist of such fragments, provided that such fragments act as an antigen and/or provide treatment for and/or protection against PEDV.

As used herein, the term "subunit" refers to a portion of the microorganism which provides protection and may itself be antigenic, i.e., capable of inducing an immune response in an animal. The term should be construed to include subunits which are obtained by both recombinant and biochemical methods.

In one embodiment, a method of identifying protective sequences of the virus or nucleic acids that elicit protection is provided. This method also includes fragments, derivatives, or homologs of the nucleic acid molecule. In one aspect, the method comprises administering to a test animal such sequences. The test and control animals are subsequently challenged with an infectious amount of a microorganism that causes the disease. Various methods and techniques for determining whether protection is provided are known to those skilled in the art, including but not limited to, observing a difference between the test and control animal in the symptoms of the disease, for example. A decrease in any of the symptoms observed in the test animal compared to the control animal indicates that protective molecule(s) provide a degree of protection against disease. Similar symptoms or an increase in any of the symptoms observed in the test animal compared to those observed in the control animal indicate that the protective molecule(s) do not provide protection.

In another aspect, determining whether the molecules provided protection against PEDV includes determining the presence or absence of challenge disease in the test animal by electron microscopy or antibody or assays such as the fluorescent focusing neutralizing (FFN) test or Western blot assay may be used. PCR methods may be used to determine if the protective molecule is present. Northern blotting can detect the presence of diagnostic sequences. In another aspect, an ELISA or similar assay, such as a hemagglutinin inhibition assay are the types of many varied assays that can determine if the protective molecule is effective. The ELISA or enzyme linked immunoassay has been known since 1971. In general, antigens solubilized in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of protein levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

Clearly, many such methods are available to one skilled in the art to ascertain if the molecule provides protection and provides protection at the levels administered to the animal.

The nucleic acid molecule, polypeptide or fragment thereof, when administered to the animal produces a protective response to PEDV. A protective response is elicited in the animal. The animal may or may not produce antibodies in response, but the animal will have decreased morbidity or mortality resulting from administration of the vaccine, and as described further herein. The terms "protecting", "protection", "protective immunity" or "protective immune response," as used herein, are intended to mean that the host animal mounts an active immune response to the vaccine or polypeptides of the present invention, such that upon exposure to disease challenge, the animal is able to combat the infection. Thus, a protective immune response will decrease the incidence of morbidity and mortality from exposure to the microorganism among a host animal. The animal will be protected from subsequent exposure to the disease-causing agent. In an embodiment, the animal may be protected by treating the animal which has already been exposed to the disease-causing agent by administration of the vaccine or polypeptide after such exposure. In such an instance there is also shown to be a lessening of morbidity and mortality. Those skilled in the art will understand that in a commercial animal setting, the production of a protective immune response may be assessed by evaluating the effects of vaccination on the herd as a whole, e.g., there may still be morbidity and mortality in a minority of vaccinated animals. Furthermore, protection also includes a lessening in severity of any gross or histopathological changes and/or of symptoms of the disease, as compared to those changes or symptoms typically caused by the isolate in similar animals which are unprotected (i.e., relative to an appropriate control). Thus, a protective immune response will decrease the symptoms of the disease compared to a control pig.

A "construct" is a package of genetic material inserted into the genome of a cell via various techniques. A "vector" is any means for the transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA or RNA replication in vivo, i.e., capable of replication under its own control. The term "vector" includes both viral and nonviral means for introducing the nucleic acid into a cell in vitro, ex vivo or in vivo. Viral vectors include alphavirus, retrovirus, adeno-associated virus, pox, baculovirus, vaccinia, herpes simplex, Epstein-Barr, rabies virus, vesicular stomatitis virus, and adenovirus vectors. Non-viral vectors include, but are not limited to plasmids, liposomes, electrically charged lipids (cytofectins), DNA- or RNA protein complexes, and biopolymers. In addition to a nucleic acid, a vector may also contain one or more regulatory regions, and/or selectable markers useful in selecting, measuring, and monitoring nucleic acid transfer results (transfer to which tissues, duration of expression, etc.).

A "cassette" refers to a segment of DNA that can be inserted into a vector at specific restriction sites. The segment of DNA encodes a polypeptide of interest or produces RNA, and the cassette and restriction sites are designed to ensure insertion of the cassette in the proper reading frame for transcription and translation.

A nucleic acid molecule is introduced into a cell when it is inserted in the cell. A cell has been "transfected" by exogenous or heterologous DNA or RNA when such DNA or RNA has been introduced inside the cell.

A cell has been "transformed" by exogenous or heterologous DNA or RNA when the transfected DNA or RNA effects a phenotypic change. The transforming DNA can be integrated (covalently linked) into chromosomal DNA making up the genome of the cell.

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene; and DNA elements that control the processing of transcripts, such as transcription termination/polyadenylation sequences. It also can contain such sequences as are needed for the eventual integration of the vector into the host chromosome.

By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner.

A nucleic acid molecule may be used in conjunction with its own or another promoter. In one embodiment, a selection marker a nucleic acid molecule of interest can be functionally linked to the same promoter. In another embodiment, they can be functionally linked to different promoters. In yet third and fourth embodiments, the expression vector can contain two or more genes of interest that can be linked to the same promoter or different promoters. For example, one promoter can be used to drive a nucleic acid molecule of interest and the selectable marker, or a different promoter used for one or each. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any host-compatible promoters. These can be plant gene promoters, such as, for example, the ubiquitin promoter (European patent application no. 0 342 926); the promoter for the small subunit of ribulose-1,5-bis-phosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed.

A promoter can additionally comprise other recognition sequences generally positioned upstream or 5' to the TATA box, referred to as upstream promoter elements, which influence the transcription initiation rate. It is recognized that having identified the nucleotide sequences for a promoter region, it is within the state of the art to isolate and identify further regulatory elements in the 5' region upstream from the particular promoter region identified herein. Thus, the promoter region is generally further defined by comprising upstream regulatory elements such as those responsible for tissue and temporal expression of the coding sequence, enhancers and the like.

Tissue-preferred promoters can be utilized to target enhanced transcription and/or expression within a particular tissue. When referring to preferential expression, what is meant is expression at a higher level in the particular tissue than in other tissue. Examples of these types of promoters include seed preferred expression such as that provided by the phaseolin promoter (Bustos et al. (1989) *The Plant Cell Vol.* 1, 839-853). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, an Ltp1 (See, for example, U.S. Pat. No. 7,550,579), an Ltp2 (Opsahl-Sorteberg, H-G. et al., (2004) *Gene* 341:49-58 and U.S. Pat. No. 5,525,716), and oleosin genes. See also WO 00/12733, where seed-preferred promoters from end1 and end2 genes are disclosed. Seed-preferred promoters also include those promoters that direct gene expression predominantly to specific tissues within the seed such as, for example, the endosperm-preferred promoter of γ-zein, the cryptic promoter from tobacco (Fobert et al. (1994) "T-DNA tagging of a seed coat-specific cryptic promoter in tobacco" *Plant J.* 4: 567-577), the P-gene promoter from corn (Chopra et al. (1996) "Alleles of the maize P gene with distinct tissue specificities encode Myb-homologous proteins with C-terminal replacements" *Plant Cell* 7:1149-1158, Erratum in *Plant Cell* 1997, 1: 109), the globulin-1 promoter from corn (Belanger and Kriz (1991) "Molecular basis for Allelic Polymorphism of the maize Globulin-1 gene" *Genetics* 129: 863-972 and GenBank accession No. L22344), promoters that direct expression to the seed coat or hull of corn kernels, for example the pericarp-specific glutamine synthetase promoter (Muhitch et al., (2002) "Isolation of a Promoter Sequence From the Glutamine Synthetases-2 Gene Capable of Conferring Tissue-Specific Gene Expression in Transgenic Maize" *Plant Science* 163:865-872 and GenBank accession number AF359511) and to the embryo (germ) such as that disclosed at U.S. Pat. No. 7,169,967. When referring to a seed or an embryo preferred promoter is meant that it expresses an operably linked sequence to a higher degree in seed or embryo tissue that in other plant tissue. It may express during seed or embryo development, along with expression at other stages, may express strongly during seed or embryo development and to a much lesser degree at other times.

The range of available promoters includes inducible promoters. An inducible regulatory element is one that is capable of directly or indirectly activating transcription of one or more DNA sequences or genes in response to an inducer. In the absence of an inducer the DNA sequences or genes will not be transcribed. Typically, the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically, the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A cell containing an inducible regulatory element may be exposed to an inducer by externally applying the inducer to the cell or plant such as by spraying, watering, heating or similar methods.

Any inducible promoter can be used. See Ward et al. *Plant Mol. Biol.* 22: 361-366 (1993). Exemplary inducible promoters include ecdysone receptor promoters, U.S. Pat. No. 6,504,082; promoters from the ACE1 system which responds to copper (Mett et al. *PNAS* 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., *Mol. Gen. Genetics* 243: 32-38 (1994)) Tet repressor from Tn10 (Gatz et al., *Mol. Gen. Genet.* 227: 229-237 (1991); or from a steroid hormone gene, the transcriptional activity of which is induced by a glucocorticosteroid hormone. Schena et al., *Proc. Natl. Acad. Sci.* U.S.A. 88: 10421 (1991); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156).

Other components of the vector may be included, also depending upon intended use of the gene. Examples include selectable markers, targeting or regulatory sequences, stabilizing or leader sequences, introns etc. General descriptions and examples of plant expression vectors and reporter genes can be found in Gruber, et al., "Vectors for Plant Transformation" in *Method in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants.

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., (1992) *Plant Mol. Biol.* 20:49, Knox, C., et al., "Structure and Organization of Two Divergent Alpha-Amylase Genes from Barley", *Plant Mol. Biol.* 9:3-17 (1987), Lerner et al., (1989) *Plant Physiol.* 91:124-129, Fontes et al., (1991) *Plant Cell* 3:483-496, Matsuoka et al., (1991) *Proc. Natl. Acad. Sci.* 88:834, Gould et al., (1989) *J. Cell. Biol.* 108:1657, Creissen et al., (1991) *Plant* 1 2:129, Kalderon, et al., (1984) "A short amino acid sequence able to specify nuclear location," *Cell* 39:499-509, Steifel, et al., (1990) "Expression of a maize cell wall hydroxyproline-rich glycoprotein gene in early leaf and root vascular differentiation" *Plant Cell* 2:785-793. When targeting the protein to the cell wall use of a signal sequence is necessary. One example is the barley alpha-amylase signal sequence. Rogers, J. C. (1985) "Two barley alpha-amylase gene families are regulated differently in aleurone cells" *J. Biol. Chem.* 260: 3731-3738.

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. *Plant Physiol* 117(4):1235-1252 (1998); Sullivan et al. *Plant Cell* 3(12):1337-48; Sullivan et al., *Planta* (1995) 196(3):477-84; Sullivan et al., *J. Biol. Chem.* (1992) 267 (26):18999-9004) and the like. One skilled in the art will readily appreciate the many options available in expressing a product to a particular organelle. Use of transit peptides is well known (e.g., see U.S. Pat. Nos. 5,717,084; 5,728,925). A protein may be targeted to the endoplasmic reticulum of the plant cell. This may be accomplished by use of a localization sequence, such as KDEL. This sequence (Lys-Asp-Glu-Leu) contains the binding site for a receptor in the endoplasmic reticulum. (Munro et al., (1987) "A C-terminal signal prevents secretion of luminal ER proteins." *Cell*. 48:899-907. There are a wide variety of endoplasmic reticulum retention signal sequences available to one skilled in the art and the KDEL sequence is one example. Another example is HDEL (His-Asp-Glu-Leu (SEQ ID NO: 24)). See, for example, Kumar et al. which discuses methods of producing a variety of endoplasmic reticulum proteins. Kumar et al. (2017) "prediction of endoplasmic reticulum resident proteins using fragmented amino acid composition and support vector machine" Peer J. doi: 10.7717/peerj.3561.

Retaining the protein in the vacuole is another example. Signal sequences to accomplish this are well known. For example, Raikhel U.S. Pat. No. 5,360,726 shows a vacuole signal sequence as does Warren et al at U.S. Pat. No. 5,889,174. Vacuolar targeting signals may be present either at the amino-terminal portion, (Holwerda et al., (1992) *The Plant Cell*, 4:307-318, Nakamura et al., (1993) *Plant Physiol.*, 101:1-5), carboxy-terminal portion, or in the internal sequence of the targeted protein. (Tague et al., (1992) *The Plant Cell*, 4:307-318, Saalbach et al. (1991) *The Plant Cell*, 3:695-708). Additionally, amino-terminal sequences in conjunction with carboxy-terminal sequences are responsible for vacuolar targeting of gene products (Shinshi et al. (1990) *Plant Molec. Biol.* 14:357-368).

The termination region can be native with the promoter nucleotide sequence can be native with the DNA sequence of interest or can be derived from another source. Convenient termination regions are available from the Ti-plasmid of *A. tumefaciens*, such as the octopine synthase (MacDonald et al., (1991) *Nuc. Acids Res.* 19(20) 5575-5581) and nopaline synthase termination regions (Depicker et al., (1982) *Mol. and Appl. Genet.* 1:561-573 and Shaw et al. (1984) *Nucleic Acids Research* Vol. 12, No. 20 pp 7831-7846 (nos). Examples of various other terminators include the pin II terminator from the protease inhibitor II gene from potato (An, et al. (1989) *Plant Cell* 1, 115-122. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Many variations on the promoters, selectable markers, signal sequences, leader sequences, termination sequences, introns, enhancers and other components of the vector are available to one skilled in the art.

The term plant refers to the entire plant or plant material or plant part or plant tissue or plant cell including a collection of plant cells. It is used broadly herein to include any plant at any stage of development, or to part of a plant, including a plant cutting, a plant cell culture, a plant organ, a plant seed, and a plantlet. Plant seed parts, for example, include the pericarp or kernel, the embryo or germ, and the endoplasm. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. In an embodiment, the tissue culture will preferably be capable of regenerating plants. Preferably, the regenerable cells in such tissue cultures will be embryos, protoplasts, meristematic cells, callus, pollen, leaves, anthers, roots, root tips, silk, flowers, kernels, ears, cobs, husks or stalks. Still further, plants may be regenerated from the tissue cultures.

Any plant species may be used, whether monocotyledonous or dicotyledonous, including but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats (*Avena*), barley (*Hordeum*), vegetables, ornamentals, and conifers. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers which may be employed in practicing the present invention include, for example, pines such as loblolly pine (*Pinus taeda*), slash pine (*Pinus elliotii*), ponderosa pine (*Pinus ponderosa*), lodgepole pine (*Pinus contotta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). An embodiment provides the plant is maize.

The method of transformation/transfection is not critical; various methods of transformation or transfection are currently available. As newer methods are available to transform crops or other host cells they may be directly applied. Accordingly, a wide variety of methods have been developed to insert a DNA sequence into the genome of a host cell to obtain the transcription or transcript and translation of the sequence to effect phenotypic changes in the organism. Thus, any method which provides for efficient transformation/transfection may be employed.

Methods for introducing expression vectors into plant tissue available to one skilled in the art are varied and will depend on the plant selected. Procedures for transforming a wide variety of plant species are well known and described throughout the literature. (See, for example, Miki and McHugh (2004) *Biotechnol.* 107, 193-232; Klein et al. (1992) *Biotechnology* (N Y) 10, 286-291; and Weising et al. (1988) *Annu. Rev. Genet.* 22, 421-477). For example, the DNA construct may be introduced into the genomic DNA of the plant cell using techniques such as microprojectile-mediated delivery (Klein et al. 1992, supra), electroporation (Fromm et al., 1985 *Proc. Natl. Acad. Sci. USA* 82, 5824-5828), polyethylene glycol (PEG) precipitation (Mathur and Koncz, 1998 *Methods Mol. Biol.* 82, 267-276), direct gene transfer (WO 85/01856 and EP-A-275 069), in vitro protoplast transformation (U.S. Pat. No. 4,684,611), and microinjection of plant cell protoplasts or embryogenic callus (Crossway, A. (1985) *Mol. Gen. Genet.* 202, 179-185). *Agrobacterium* transformation methods of Ishida et al. (1996) and also described in U.S. Pat. No. 5,591,616 are yet another option. Co-cultivation of plant tissue with *Agrobacterium tumefaciens* is a variation, where the DNA constructs are placed into a binary vector system (Ishida et al., 1996 *Nat. Biotechnol.* 14, 745-750). The virulence functions of the *Agrobacterium tumefaciens* host will direct the insertion of the construct into the plant cell DNA when the cell is infected by the bacteria. See, for example, Fraley et al. (1983) *Proc. Natl. Acad. Sci. USA,* 80, 4803-4807. *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) *Plant J.* 6, 271-282 and Lee et al. (1991) *Proc. Nat. Acad. Sci. USA* 88, 6389-6393. Standard methods for transformation of canola are described by Moloney et al. (1989) *Plant Cell Reports* 8, 238-242. Corn transformation is described by Fromm et al. (1990) *Biotechnology* (N Y) 8, 833-839 and Gordon-Kamm et al. (1990) supra. Wheat can be transformed by techniques similar to those used for transforming corn or rice. Sorghum transformation is described by Casas et al. (Casas et al. (1993). Transgenic sorghum plants via microprojectile bombardment. Proc. Natl. Acad. Sci. USA 90, 11212-11216) and barley transformation is described by Wan and Lemaux (Wan and Lemaux (1994) Generation of large numbers of independently transformed fertile barley plants. *Plant Physiol.* 104, 37-48). Soybean transformation is described in a number of publications, including U.S. Pat. No. 5,015,580.

In one method, the *Agrobacterium* transformation methods of Ishida et al. (1996) and also described in U.S. Pat. No. 5,591,616, are generally followed, with modifications that the inventors have found improve the number of transformants obtained. The Ishida method uses the A188 variety of maize that produces Type I callus in culture. In an embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in the U.S. Pat. No. 5,591,616, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the *Agrobacterium* on plates, scraping the bacteria from the plates, and resuspending in the co-culture medium as stated in the U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase and are harvested at a density of no more than $OD_{600}=0.5$, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985).

The result is redifferentiation of the plant cells and regeneration into a plant. Redifferentiation is sometimes referred to as dedifferentiation, but the former term more accurately describes the process where the cell begins with a form and identity, is placed on a medium in which it loses that identity and becomes "reprogrammed" to have a new identity. Thus, the scutellum cells become embryogenic callus.

A transgenic plant may be produced that contains an introduced nucleic acid molecule encoding the polypeptide.

When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman (1995) *Breeding Field Crops*. AVI Publication Co., Westport Conn., 4$^{th}$ Edit.). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Selection and propagation techniques described above can yield a plurality of transgenic plants that are harvested in a conventional manner. The plant or any parts expressing the recombinant polypeptide can be used in a commercial process, or the polypeptide extracted. When using the plant or part itself, it can, for example, be made into flour and then applied in the commercial process. Polypeptide extraction from biomass can be accomplished by known methods. Downstream processing for any production system refers to all unit operations after product synthesis, in this case protein production in transgenic seed (Kusnadi, A. R., Nikolov, Z. L., Howard, J. A., 1997. *Biotechnology and Bioengineering*. 56:473-484). For example, seed can be processed either as whole seed ground into flour or, fractionated and the germ separated from the hulls and endosperm. If germ is used, it is usually defatted using an extraction process and the remaining crushed germ ground into a meal or flour. In some cases, the germ is used directly in the process or the protein can be extracted (See, e.g. WO 98/39461). Extraction is generally made into aqueous buffers at specific pH to enhance recombinant protein extraction and minimize native seed protein extraction. Subsequent protein concentration or purification can follow.

The compositions and process described here are also to producing and administering a vaccine that protects an animal from PEDV.

As used herein, the term "vaccine" as used herein refers to a pharmaceutical composition comprising at least one protective molecule, that induces protective response in an animal and possibly, but not necessarily, one or more additional components that enhance the activity of said active component. A vaccine may additionally comprise further components typical to pharmaceutical compositions. In another form, the immunologically active component of a vaccine may comprise appropriate elements of said organisms (subunit vaccines) whereby these elements are generated either by destroying the whole organism or the growth cultures of such microorganisms and subsequent purification steps yielding in the desired structure(s), or by synthetic processes induced by an appropriate manipulation of a suitable system such as, but not restricted to, bacteria, insects, mammalian, or other species, plus subsequent isolation and purification procedures or by induction of said synthetic processes in the animal needing a vaccine by direct incorporation of genetic material using suitable pharmaceutical compositions (polynucleotide vaccination). A vaccine may comprise one or simultaneously more than one of the elements described above.

The present vaccines may include a pharmaceutically acceptable carrier, excipient, carrier, stabilizer and/or diluent. Without intending to be limiting, examples include wetting agents and lubricating agents, preservative agents, lipids, stabilizers, solubilizers and emulsifiers. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. Examples of stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin).

It is possible to provide an adjuvant in the vaccine. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Immunostimulatory agents or adjuvants have been used for many years to improve the host immune responses to, for example, vaccines. The vaccines of the present invention may be used in conjunction with an adjuvants, for example, lipopolysaccharides, aluminum hydroxide and aluminum phosphate (alum), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. Desirable characteristics of ideal adjuvants may include: (1) lack of toxicity; (2) ability to stimulate a long-lasting immune response; (3) simplicity of manufacture and stability in long-term storage; (4) ability to elicit both CMI and HIR to antigens administered by various routes; (5) synergy with other adjuvants; (6) capability of selectively interacting with populations of antigen presenting cells (APC); (7) ability to specifically elicit appropriate T-cell helper 1 (TH 1) or TH 2 cell-specific immune responses; and (8) ability to selectively increase appropriate antibody isotype levels (for example, IgA) against antigens. An adjuvant used with the present compositions and methods need not possess all these characteristics to be used.

As used herein, "immunogenically effective amount" refers to an amount, which is effective in reducing, eliminating, treating, preventing or controlling the symptoms of the infections, diseases, disorders, or condition.

The quantity to be administered depends on the subject to be treated, including, for example, the capacity of the immune system of the individual to mount a protective response. Suitable regimes for initial administration and booster doses are also variable but may include an initial administration followed by subsequent administrations. For example, it may be desirable to provide for an initial administration of the vaccine followed by additional doses. The need to provide an effective amount of the protective molecule will also need to be balanced with cost of providing higher amounts of the protective molecule. A cost effective vaccine is one in which the cost of producing it is less than the value one can obtain from using it. Measurement and determination of efficacy of any of the compositions and vaccines of the invention may be accomplished by any of the many methods available to one skilled in the art.

In one embodiment, a straightforward and quick method can be to perform a Western blot analysis of a sample candidate vaccine composition to quantitate the amount of polypeptide or fragment thereof in the sample. In one embodiment, one compares the amount of polypeptide to a standard known to be effective with like polypeptides from other biotypes, and either prepares a vaccine where the level of polypeptide produced is at least at this standard or higher or may test the vaccine with a test animal.

The compounds described herein can be administered to a subject at therapeutically effective doses to prevent PEDV-associated diseases. The dosage will depend upon the host receiving the vaccine as well as factors such as the size, weight, and age of the host.

The precise amount of immunogenic composition of the invention to be employed in a formulation will depend on the route of administration and the nature of the subject (e.g., age, size, stage/level of disease), and should be decided according to the judgment of the practitioner and each subject's circumstances according to standard clinical techniques. An effective immunizing amount is that amount sufficient to treat or prevent a PEDV infectious disease in a subject.

Immunogenicity of a composition can be determined by monitoring the immune response of test subjects following immunization with the composition by use of any immunoassay known in the art. Generation of a humoral (antibody) response and/or cell-mediated immunity may be taken as an indication of an immune response.

The immune response of the test subjects can be analyzed by various approaches such as: the reactivity of the resultant immune serum to the immunogenic conjugate, as assayed by known techniques, e.g., enzyme linked immunosorbent assay (ELISA), immunoblots, immunoprecipitations, virus neutralization, etc.; or, by protection of immunized hosts from infection by the pathogen and/or attenuation of symptoms due to infection by the pathogen in immunized hosts as determined by any method known in the art, for assaying the levels of an infectious disease agent, e.g., the viral levels (for example, by culturing of a sample from the subject), or other technique known in the art. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective.

The therapeutics of the invention can be tested in vitro for the desired therapeutic or prophylactic activity, prior to in vivo use in animals. For example, in vitro assays that can be used to determine whether administration of a specific therapeutic is indicated include in vitro cell culture assays in which appropriate cells from a cell line or cells cultured from a subject having a particular disease or disorder are exposed to or otherwise administered a therapeutic, and the effect of the therapeutic on the cells is observed.

Alternatively, the therapeutics may be assayed by contacting the therapeutic to cells (either cultured from a subject or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art.

In addition, the therapeutics can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal to PEDV using the methods and compositions of the present invention, any binding assay known in the art can be used to assess the binding between the resulting antibody and the particular molecule. These assays may also be performed to select antibodies that exhibit a higher affinity or specificity for the particular antigen. As one measure of vaccine potency, an ELISA can be performed on a sample collected from an individual vaccinated to determine whether antibodies to a vaccine comprising the sequence, a derivative, a homologue or a variant or fragment thereof generated anti-polypeptide antibodies. The individual's sample is measured against a reference anti-polypeptide antibody. Analysis of symptoms and measurement of animal weight gain also demonstrated lessening of impact of the disease in the presence of a particular dose. Fluorescent focused neutralization assay is still another assay to detect serum neutralizing antibodies and analyze effectiveness of a vaccine and a particular dose.

When testing animals administered the vaccine, for example, measuring antibody response is also effective in determining efficacy of the vaccine. Sera may be collected and titer measured as the reciprocal of the maximal dilution at which hemagglutination is inhibited, as described in an example below. Other measurements post-administration of the vaccine can also be employed to determine effectiveness, whether pathological evaluation, isolation of the pathogen, measurement of symptoms, and overall health and weight gain of the animal.

Thus, the effectiveness of the present vaccine may also be evaluated quantitatively (for example, a decrease in the percentage of diseased tissue as compared to an appropriate control group) or qualitatively (e.g., isolation of virus from blood, detection of virus antigen in a tissue sample by an assay method, etc.). The symptoms of the disease may be evaluated quantitatively (e.g., temperature/fever), semi-quantitatively (e.g., severity of distress, or qualitatively (e.g., the presence or absence of one or more symptoms or a reduction in severity of one or more symptoms). Clearly one skilled in the art has many different options available for measuring effectiveness of the vaccine. With the present invention, it is possible to achieve protection against disease in an aquatic invertebrate, and which protection is provided for longer periods than have been achieved in such animals. Protection periods of more than seven days after at least one challenge or exposure to the pathogenic microorganism have been achieved, and protection of at least two weeks, at least 20 days, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days or more, have been achieved using the invention. Such protection periods are also provided when using the invention with other animals. The protective response is also shown here in an embodiment to be specific to the disease as opposed to another disease, and thus demonstrates specific memory.

The vaccine can be administered any convenient method including intranasal, oral and/or parenteral (e.g., intramuscular) administration. For example, the Spike PEDV containing vaccine can be administered intramuscularly one or more times. In another embodiment of the method, for example, the vaccine is administered orally one or more times. In an alternative embodiment oral administration can be followed by and/or precede administration of the vaccine at least once, intramuscularly. The maize grain can be fed to the animal, thereby reducing cost and loss of antigen that can occur through further processing.

The following is provided by way of illustration within intending to be limiting of the scope of the invention. All references cited herein are incorporated herein by reference.

EXAMPLES

Example 1

The Spike (S1) nucleotide sequence set forth below was introduced into constructs as outlined below and as shown in FIG. 1. S1 refers to the 2238 bp nucleotide sequence set forth in SEQ ID NO: 1. S1(ext) refers to a 2415 bp sequence (SEQ ID NO: 2). The protein encoded by the S1 nucleotide sequence is SEQ ID NO: 3 and the protein encoded by the S1(ext) nucleotide sequence is SEQ ID NO: 4. BAASS refers to the barley alpha amylase signal sequence (SEQ ID NO: 5, the polypeptide encoded is SEQ ID NO: 6, PinII refers to the potato proteinase inhibitor polyadenylation sequence, M refers to a PEDV matrix protein encoding nucleotide sequence (SEQ ID NO: 7, the polypeptide encoded is SEQ ID NO: 8), N refers to PEDV N protein (a SEQ ID NO: 10, the polypeptide encoded is SEQ ID NO: 11); DR13 refers to a South Korea strain of the virus (SEQ ID NO: 25 is the nucleotide, the encoded polypeptide is SEQ ID NO: 9); COE refers to a small portion of the S1 protein that is involved in the immune response and the sequence set forth below (SEQ ID NO: 12). DCpep refers to the dendritic binding peptide. An embodiment provides the Spike polypeptide is fused to a dendritic cell targeting sequence, (DC3) (SEQ ID NO: 13)., and/or a heat labile enterotoxin B subunit (LtB) peptide (SEQ ID NO: 14 and the polypeptide encoded is SEQ ID NO: 15). Dendritic cells are antigen-presenting cells that participate in activation of T cells. Polypeptides may be targeted to dendritic cells. See Mohamadzadeh et al. (2009) "Dendritic cell targeting of *Bacillus anthracis* protective antigen expressed by *Lactobacillus acidophilus* protects mice from lethal challenge" Proc. Natl. Acad. Sci USA 106, 4331-4336.

Reference to the promoter pr25 refers to the maize globulin-1 gene (SEQ ID NO: 16), pr39 refers to a maize 27kD gamma-zein gene promoter (SEQ ID NO: 17); and pr44 refers to the pr25 globulin-1 promoter, with two extra copies of a portion of the promoter (SEQ ID NO: 18).

All fragments were optimized for maize codon usage and synthesized by Genescript. Full length coding sequence fragments were synthesized for the constructs with the US or DR13 strains with the BAASS signal sequence, as well as for the COE-DC peptide construct. Constructs with vacuolar or KDEL signal sequences (SEQ ID NO: 19) were prepared by synthesis of partial fragments and reconstruction of the full coding region using NcoI, EcoR1 and HindIII restriction sites to exchange with the BAASS full length S1 synthesized fragments. A partial fragment was also ordered for the S1 Ext and used to reconstruct the full coding region by restriction digestion with HindIII+PacI. Cloning into the pSB11 vector was by NcoI and PacI restriction sites. Constructs with double copies of the complete promoter + coding region transcription unit were prepared by digestion with AscI and MluI and ligation of the second copy of the transcription unit.

The entire PEDV sequence is SEQ ID NO: 20, with the Spike protein encoded SEQ ID NO: 21.

Figure 2:
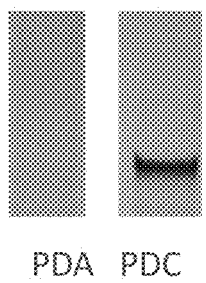
FIG. 2 is a gel of a Western blot, showing expression of the S protein.

The S protein is extremely difficult to express in other hosts and therefore we did not know what to expect in the maize grain. It was surprising that the construct PDA with an apoplast targeting sequence provided poor expression levels of the protein while the PDC construct with an ER targeting sequence demonstrated good levels of expression (See FIG. 2).

Example 2

1. Material

Seed from construct PDC (T1) was used for this trial. The T1 seed (800 g @ 13.5% moisture) was brought up to 21% moisture using USP sterile water and soaking overnight at ambient temperature in preparation of processing.

Some of the T1 seed was planted in the greenhouse to obtain enough seed for the trial (T2 seed). Six ears were selected at random to evaluate the presence of S1 antigen and the results showed that 5 out of the six ears were expressing as expected. 2100 g of T2 seed @11% moisture was therefore pooled (SG180001-SG180004) and soaked overnight as above to obtain a final moisture of 22%. Both the T1 and T2 seed were then combined to obtain 3,600 g of PDC seed.

The seed was put through a pin mill and then hand sieved through a #6 mesh screen to enrich for germ. The enriched germ fraction was dried to 11% and then put through the Glen Mill grinder to obtain corn meal. This was then sieved through a #10 mesh screen to remove pericarp. The final PDC meal was then distributed into 50 ml centrifuge tubes containing 14.5 g of meal/tube. This process was repeated using commercial corn seed.

For quantitation, ELISA and Westerns used a much smaller protein containing the COE domain as the standard as recombinant full length S1 protein is not available at this time. Based on the COE standard, estimates of S1 ranged from 0-40 mg/kg seed in T1 seed with most of the T1 seed and T2 seed testing at 3-10 mg/kg seed. With a moderate increase in concentration due to germ enrichment and a dosage of 29 grams/day, ELISA estimated indicate a dosage of ~1 mg of S1/day.

TABLE 1

Treatment Groups:

| Group | Primary administration | Boost |
|---|---|---|
| A | Inject | Inject |
| B | Inject | Oral S1 maize |
| C | Inject | Oral Control maize |
| D | Oral S1 Maize | Oral S1 Maize |
| E | Oral Control Maize | Oral Control mazie |

2. Trial Initiation

Animals used in the study were 18-21 days old. Each treatment group consist of 4 animals. Animals were placed in 5 pens such and each pen will represent a separate treatment group. The treatment groups consist of that in Table 1. Material used for oral delivery with letter codes (B-E) that correspond to the treatments shown in Table 1.

3. Pre Challenge Activity
a. All animals will be observed daily for changes in general health. Daily observations will be recorded.
b. Daily environmental conditions will be recorded and will include room temp hi/low and a check of the feeders and waterers.
c. Fecal and serum samples to be taken and stored frozen on the days indicated in Table 2. When administration of the candidates and sample collection fall on the same day, all samples will be taken prior to administration of injected or oral material. Sera and fecal sample collection will be recorded
d. Blood will be collected (minimum of 5 ml) clotted and sera centrifuged and placed in vials.
e. One serum sample will be distributed into three vials (minimum, 1 ml each) and then frozen. The freezers temperatures will be monitored daily and the hi/low temperatures recorded manually.
f. Fecal swabs will be obtained. The fecal material will be divided into three vials and frozen (minimum 0.1 gram/vial).
g. When ready to ship, one frozen sample from the Tier 1 sample list in Diagnostic section below, will be shipped on dry ice to the diagnostic lab. The remainder kept frozen for sample retention.
h. Animals will be administered oral vaccine candidates according to the schedule in Table 2, below. Animals will be individually fed 2 labeled tubes/day (29 g material).
i. Animals will be given the parenteral vaccine according to the schedule in Table 2, below using the recommended dosage (Zoetis killed vaccine 2 ml IM).
j. Animals will be observed for any changes in health during the course of the study.
k. Weights will be taken of the animals just prior and to challenge and at the end of the study.

4. Challenge Activity
a. Virus for the challenge will be obtained (isolate PEDV USA/NC49469/2013).
b. PEDV will be given by IG for a full dose of (10 ml of 10^4-10^5 TCID50/ml).
c. Fecal and serum samples will be collected, as above, according to the schedule in Table 2.
d. Daily observations will be done with special attention to diarrhea symptoms and weights taken every 4 days.

TABLE 2

Activity:

MZ-S-18-1221

| DOT | Date | Day of Wk | Activity | Gen obs | Clin obs | Blood | Feces | Weigh |
|---|---|---|---|---|---|---|---|---|
| −6 | 7 Aug. 2018 | tue | arrival | x | | | | |
| −5 | 8 Aug. 2018 | wed | allot to treatments | x | | | | x |
| −4 | 9 Aug. 2018 | thu | | x | | | | |
| −3 | 10 Aug. 2018 | fri | | x | | | | |
| −2 | 11 Aug. 2018 | sat | | x | | | | |
| −1 | 12 Aug. 2018 | sun | | x | | | | |
| 0 | 13 Aug. 2018 | mon | Administer Trts to Gps A-E | x | x | x | x | |
| 1 | 14 Aug. 2018 | tue | Administer Trts to Gp D, E | x | | | | |
| 2 | 15 Aug. 2018 | wed | Administer Trts to Gp D, E | x | | | | |
| 3 | 16 Aug. 2018 | thu | | x | | | | |
| 4 | 17 Aug. 2018 | fri | | x | | | | |
| 5 | 18 Aug. 2018 | sat | | x | | | | |
| 6 | 19 Aug. 2018 | sun | | x | | | | |
| 7 | 20 Aug. 2018 | mon | | x | | | | |
| 8 | 21 Aug. 2018 | tue | | x | | | | |
| 9 | 22 Aug. 2018 | wed | | x | | | | |

TABLE 2-continued

Activity:

MZ-S-18-1221

| DOT | Date | Day of Wk | Activity | Gen obs | Clin obs | Blood | Feces | Weigh |
|---|---|---|---|---|---|---|---|---|
| 10 | 23 Aug. 2018 | thu | | x | | | | |
| 11 | 24 Aug. 2018 | fri | | x | | | | |
| 12 | 25 Aug. 2018 | sat | | x | | | | |
| 13 | 26 Aug. 2018 | sun | | x | | | | |
| 14 | 27 Aug. 2018 | mon | | x | | | | |
| 15 | 28 Aug. 2018 | tue | | x | | | | |
| 16 | 29 Aug. 2018 | wed | | x | | | | |
| 17 | 30 Aug. 2018 | thu | | x | | | | |
| 18 | 31 Aug. 2018 | fri | | x | | | | |
| 19 | 1 Sep. 2018 | sat | | x | | | | |
| 20 | 2 Sep. 2018 | sun | | x | | | | |
| 21 | 3 Sep. 2018 | mon | | x | | | | |
| 22 | 4 Sep. 2018 | tue | | x | | | | |
| 23 | 5 Sep. 2018 | wed | | x | | | | |
| 24 | 6 Sep. 2018 | thu | | x | | | | |
| 25 | 7 Sep. 2018 | fri | | x | | | | |
| 26 | 8 Sep. 2018 | sat | | x | | | | |
| 27 | 9 Sep. 2018 | sun | | x | | | | |
| 28 | 10 Sep. 2018 | mon | Administer Trts to Gps A-E | x | | x | x | x |
| 29 | 11 Sep. 2018 | tue | Administer Trts to Gp B-E | x | | | | |
| 30 | 12 Sep. 2018 | wed | Administer Trts to Gp B-E | x | | | | |
| 31 | 13 Sep. 2018 | thu | | x | | | | |
| 32 | 14 Sep. 2018 | fri | | x | | | x | |
| 33 | 15 Sep. 2018 | sat | | x | | | | |
| 34 | 16 Sep. 2018 | sun | | x | | | | |
| 35 | 17 Sep. 2018 | mon | | x | | | x | |
| 36 | 18 Sep. 2018 | tue | | x | | | | |
| 37 | 19 Sep. 2018 | wed | | x | | | | |
| 38 | 20 Sep. 2018 | thu | | x | | | x | |
| 39 | 21 Sep. 2018 | fri | | x | | | | |
| 40 | 22 Sep. 2018 | sat | | x | | | | |
| 41 | 23 Sep. 2018 | sun | | x | x | | | |
| 42 | 24 Sep. 2018 | mon | Challenge all gps | x | x | x | x | x |
| 43 | 25 Sep. 2018 | tue | | x | x | | | |
| 44 | 26 Sep. 2018 | wed | | x | x | | x | |
| 45 | 27 Sep. 2018 | thu | | x | x | | | |
| 46 | 28 Sep. 2018 | fri | | x | x | | x | x |
| 47 | 29 Sep. 2018 | sat | | x | x | | | |
| 48 | 30 Sep. 2018 | sun | | x | x | | x | |
| 49 | 1 Oct. 2018 | mon | | x | x | | | |
| 50 | 2 Oct. 2018 | tue | | x | x | | x | x |
| 51 | 3 Oct. 2018 | wed | | x | x | | | |
| 52 | 4 Oct. 2018 | thu | | x | x | | x | |
| 53 | 5 Oct. 2018 | fri | | x | x | | | |
| 54 | 6 Oct. 2018 | sat | | x | x | | x | x |
| 55 | 7 Oct. 2018 | sun | | x | x | | | |
| 56 | 8 Oct. 2018 | mon | | x | x | | | |
| 57 | 9 Oct. 2018 | tue | Euthanize pigs | x | x | x | x | x |

5. Diagnostics a. Tier 1 i. Neutralization assays will be performed 1 for sera from day 42 and 57 of all pigs ii. Neutralizing activity from fecal samples of day 35, 42 of all pigs iii. PCR will be used to detect virus shedding in feces at day 42, 46, 50, 54, and 57 for pigs from in all groups.

b. Tier 2 i. If neutralizing activity is detected in sera or fecal matter then additional tests may be requested for days not initially tested.

ii. Additional PCR tests may be done depending on the initial test for days not tested.

iii. Any test may be repeated for any reason.

c. Titers for anti-PEDV sera antibodies (IgA and IgG) or IgA in fecal samples will be done at the conclusion of the study.

Example 3

In this work, we evaluated constructs containing the S1 subunit of the spike protein in transgenic maize targeted to various cellular locations as well as S1 fused to carrier proteins with the goal of accumulating the S1 antigen at concentrations high enough to use the maize grain directly for oral administration of the vaccine candidate. The highest levels were obtained in constructs targeted to the endoplasmic reticulum (ER) or as fusions with the B subunit of *E. coli* heat-labile enterotoxin or a dendritic cell binding peptide. Maize material harboring the construct targeting S1 to the ER was then orally administered to pigs and shown to elicit neutralizing antibodies. This opens the possibility of using maize-produced antigen as a practical approach for a new type of PEDV vaccine.

We have produced maize lines targeting expression of PEDV spike protein to various subcellular locations and in combination with proteins known to increase immunogenicity. Relatively high accumulation of the S1 portion of the spike protein was observed using a construct targeted to the endoplasmic reticulum (ER) as well as using fusions of S1 with the *E. coli* heat labile subunit (LTB) and a dendritic cell (DC) binding peptide that may act as carriers to increase immunogenicity. Expression levels were at least 5 mg/kg of whole seed._ S1 ER-targeted maize material was orally administered to piglets and elicited a serum neutralizing antibody response. To our knowledge, this is the first report of an immune response in pigs using plant-produced material expressing PEDV S1 to elicit neutralizing antibodies on oral delivery. This proof-of-concept provides encouragement for this approach in the development of an effective oral vaccine against this disease.

Methods

Preparation of Constructs

The sequence of the spike protein from the PEDV strain Colorado 2013 (Genbank KF272920) was optimized for maize codon usage (See Examples above). The nucleotide sequence of the coding region was outsourced for commercial gene synthesis by GenScript. Six different constructs were prepared (FIG. 1) with varying subcellular localizations and fusions. The native signal sequence was replaced with a barley alpha amylase signal sequence for cell wall targeting in constructs PDA, PDC, PDD, PDK, and PDM and with a vacuolar targeting sequence in construct PDB. The S1 coding region (aa 23-738 for constructs PDA, PDB, PDC, and PDB or aa 23-789 for constructs PDK and PDM) was synthesized for transfer into the maize transformation vector pSB11[18] using NcoI and PacI restriction sites. For the other constructs, smaller portions of the coding region containing, for example, the KDEL ER targeting sequence, were commercially synthesized to exchange with portions of the full-length coding region by restriction digestion and ligation. All constructs except one, PDD, incorporated the S1 coding region under control of a promoter derived from the maize globulin-1 gene (pr25 or pr44) which target expression to the embryo. In construct PDM an engineered version of the pr25 promoter, pr44, contains two extra copies of the 5' region of pr25[19]. One construct (PDD) incorporated the S1 protein under control of a promoter (pr39, derived from the maize 27 kDa gamma zein gene) targeting expression to the endosperm. Each transcription unit also incorporated the terminator from potato proteinase inhibitor II. Subcellular localization and terminator sequences were as previously described[19].

Maize Transformation

Maize transformation was carried out as previously described with modifications[20]. In brief, the constructs were transferred into the LBA4404 Agrobacterium strain containing the vector pSB1 by a triparental mating procedure[18]. The cointegrate DNA was then electroporated into *Agrobacterium tumefaciens* strain EHA101[21]. HiII maize embryos roughly 1.5 to 3 mm in length were mixed with *A. tumefaciens* EHA101 with the appropriate vector for transformation[20]. Plants from events selected on bialaphos were grown to maturity in the greenhouse and pollinated with HiII to produce T1 generation seed.

Western Blot Analysis

A small antigenic portion of the S1 protein known as the core neutralizing epitope (COE, aa 494-641) was cloned, expressed and purified by GenScript. The resulting protein was used as an immunogen to prepare polyclonal anti-S1 antibodies in rabbit by Pacific Immunology. Ground maize seed was extracted in 1×PBS+1% SDS, loaded onto a 4-12% bis-tris gel (LifeTech), and transferred to PDVF membrane by iBlot. The blot was incubated in Pacific Immunology's custom rabbit anti-PEDV S1 overnight and developed with anti-rabbit-alkaline phosphatase conjugate (Jackson Immunoresearch #111-055-003)) and BCIP-NBT liquid substrate (Sigma). The concentration of S1 was estimated using the COE standard synthesized by Genscript. Levels were at least 10 mg/kg of whole seed.

Pig Study

Preparation of Material

Several high-expressing maize lines were identified for construct PDC. Seed from the first generation of plants (T1) was planted to obtain additional grain (T2) for pig studies. T1 and T2 generation material was pooled and used for the animal studies. Since expression was targeted to the embryo, the antigen was further concentrated for S1 by enriching for the germ fraction using customized small scale processing equipment. The germ fraction was then dried to obtain a moisture content of 11% and ground such that >80% of the material could pass through a 20 mesh screen.

Animals and Treatment Groups

A double-blind study was conducted by Veterinary Resources Inc. (VRI, Ames, Iowa). Twelve pigs 18-21 days old were used (Wilson's Prairie View Farms, Burlington, Wis.) and determined to be free from PEDV by PCR analysis of fecal material and by serum neutralizing tests performed by South Dakota State University Diagnostics Laboratory. The pigs were randomly divided on a weight basis into treatment groups and housed in separate pens. Pigs were fed Ultra Care 240 or 500 Med. A primary dose was administered after six days acclimation. PDC maize material was fed to pigs as a prime and booster dose (Table 3). The boost occurred two weeks after the primary dose. Another treatment consisted of pigs that were injected with a commercial virus-based vaccine, while a third group was administered untransformed ground maize germ. Animals (4 per treatment) were either fed recombinant or control ground maize material (29 g/day on three successive days for a total of 87 g) or injected intramuscularly with a commercially available killed virus vaccine (Zoetis). The animals were fasted for four hours before being offered the maize material and returned to their normal diet an hour after administration. Each animal was hand fed and consumed the full dose of maize material offered. At day 28 a booster dose of oral material or injection was administered.

Challenge, Sample Collection, and Analysis of Serum Response

Virus (isolate PEDV USA/NC49469/2013) for challenge was obtained from Dr. Jianqiang Zhang at Iowa State University. Challenge by intragastric inoculation was on day 42 after primary immunization with 10 mL at $10^4$ to $10^5$ TCID50/mL. Serum samples were collected on days 0 (pre-screen), day 42 (pre-challenge), and 15 days after challenge. Serum neutralizing antibody (SNA) response was determined by fluorescent focus neutralization assay at the South Dakota State University Diagnostics Laboratory. Fecal samples were collected and an assay for mucosal response will confirm such a response by the animal.

Statistics

A mixed effects analysis of variance was used to analyze the data with the final titer as response variable of interest and the treatment group and the weight group as factors. Weight group was included in the analysis as a random effect to account for any variation in the titers due to animal weight. Differences in the treatment groups were compared using Tukey's HSD procedure with a 5% significance level. The data were analyzed on a base-2 log scale. Comparing the titers on the log scale detects significant differences between the treatment groups (p-value=0.05). The differences between groups were determined using the Tukey HSD method.

Results

Expression of S1.

Figure 3:
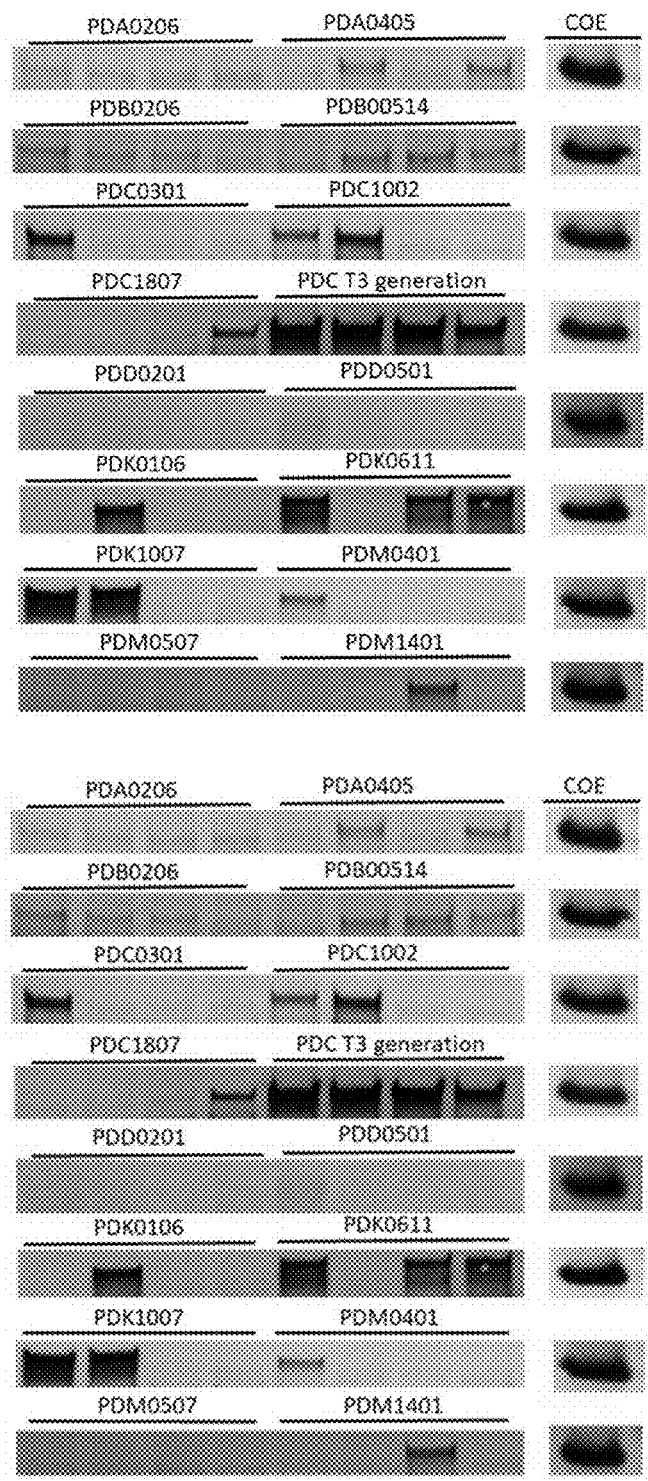
FIG. 3 is a gel of a Western blot of S1 expression in representative seed.

Constructs coding for the PEDV S protein S1 subunit labeled PDA, PDB, PDC, PDD, PDK AND PDM were prepared and transformed into maize to produce the subunit vaccine. See FIG. 1. Three constructs, PDC, PDK, and PDM, showed the highest levels of expression of PEDV S1 (>20 ug/g seed), based on Western blot analysis of single seeds (FIG. 3). Expression levels were at least 10 mg/kg of whole seed. Construct PDC codes for a portion of the spike protein S1 region incorporating amino acids 23-738 with a barley-alpha amylase signal sequence at the N-terminus and a KDEL sequence for endoplasmic reticulum (ER) retention at the C-terminus. Construct PDK contains an extended S1 protein incorporating amino acids 23-789, with the barley-alpha amylase signal sequence replacing the signal sequence at the N-terminus and fused to the *E. coli* heat-labile enterotoxin (LTB) at the carboxy terminus. Construct PDM contains the extended S1 protein fused to a dendritic cell targeting (DC) peptide at the carboxy terminus. In each case expression is under control of a promoter derived from the maize globulin 1 gene that directs expression to the embryo portion of the maize kernel, with the exception of construct PDD, in which the coding region is under control of an endosperm-targeted promoter. Also, in each of these cases the plant transcription unit was duplicated in the final construct. Constructs targeting expression to the cell wall (PDA), to the vacuole (PDB), or under control of a promoter targeting expression to the endosperm portion of the kernel (PDD) showed minimal expression relative to PDC, PDK, and PDM. Four representative individual seeds for the indicated plant were pulverized and extracted in 1×PBS+1% SDS. The protein was transferred to PVDF membrane and incubated with polyclonal rabbit antibody raised to commercially synthesized COE portion of the spike protein (shown as a positive control at the right). Note that in all cases except PDC T3 generation, T1 generation seed crossed to untransformed maize is shown and half of the seed are expected to be positive. PDC T3 has been self-crossed leading to expression in all seeds.

Animal Study.

PDC maize material was prepared as ground meal and fed to pigs as a prime and booster dose (Table 3). Quantitation of S1 was estimated by comparison of the intensity of bands on western blots using the COE peptide as the standard. Based on this estimate, each dose contained approximately 0.8 mg of S1.

TABLE 3

Pig study design:

| Group | Prime | Boost |
|---|---|---|
| 1 | Injected | Injected |
| 2 | Oral S1 Maize | Oral S1 Maize |
| 3 | Oral Control Maize | Oral Control Maize |

Figure 4:
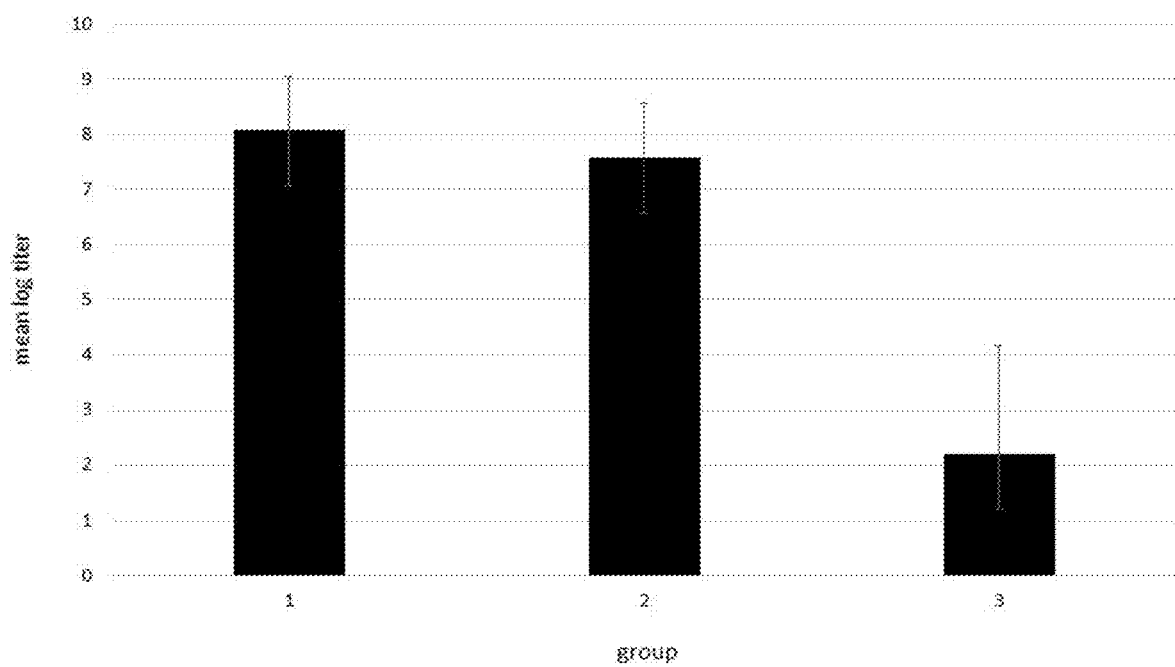
FIG. 4 is a graph showing pig antibody response after exposure to oral or injected vaccines. Group 1 is the injection group, Group 2 is the oral vaccination group and Group 3 is the control, as described below.

The pigs were screened before immunization and found to have a serum neutralizing antibody titer not above background. Serum neutralizing antibodies (SNA) were only observed prior to the challenge in pigs administered the injected vaccine. After the challenge, the pigs administered orally delivered antigens and injected vaccines both showed a significant increase in SNA over the control group. In both cases the response was statistically different from the control group administered untransformed maize. There was not, however, a statistically significant difference between the two vaccinated groups. Symptoms were monitored but only minor diarrhea was observed. This is most likely due to the age of the pigs (~2 months), as newborn pigs are most susceptible to PEDV. Sera antibody titers were surprisingly high with the orally administered vaccine. In the control, viral neutralizing antibody titers observed were 10 in control animals, 200 in animals receiving oral vaccine and 340 in animals receiving injection vaccine. FIG. 4 shows Pig antibody response. FIG. 4 shows the mean of the log titer. Serum neutralizing antibody response from the indicated groups (n=4) were assessed by fluorescent focus neutralization assay at 15 days post-challenge (dpc), as described in the methods section. At 15 dpc treatment groups containing S1 (one and two) showed significant differences with the control group (three) with p-values for each comparison substantially below 0.05. There was no significant difference in the titers between treatment groups one (injected S1) and two (orally-delivered maize S1). Group 1 is the group receiving injection, Group 2 is the group receiving oral administration of plant material with the vaccine and Group 3 is the control group receiving oral administration of corn not comprising the transgene.

Discussion

We have demonstrated relatively high levels of accumulation in maize grain of the PEDV spike protein S1, when targeted to the ER. This can allow for the cost efficient production of a subunit vaccine as this antigen has been very difficult to express in other systems. More critically, however, we have also shown that after the virus challenge, maize-produced orally delivered S1 was able to elicit serum neutralizing antibodies in pigs similar to those elicited by the commercial injected vaccine post challenge. Prior to the virus challenge, little serum neutralizing antibody response was detected in the group fed maize-produced S1 or controls. This observation is similar to earlier results with TGEV that showed significant titers only after the viral challenge. Presumably, this is due to a response below the limits of detection after the first boost of the vaccine. The relatively high serum response is surprising in that the response seen in the sera is normally low compared to the response in mucosal tissues when candidates are orally delivered. This is encouraging as the mucosal response is likely to be even more robust and may be more protective for this disease than the serum response. Future work will include development of reliable methods for detection of mucosal response.

Newborn piglets are most susceptible to PEDV and clinical symptoms in this study were minimal after the viral challenge in all groups due to the older age of the pigs. The ideal commercial vaccine will use vaccination of sows to allow for lactogenic immunity from colostrum to be passed to suckling piglets. Additional material is being generated that will allow more extensive studies addressing lactogenic immunity. This may require higher levels of antigen for the much larger dams. If needed, this can be achieved either by increasing the S1 concentrations using selection, as described earlier for other antigens[22] and shown in FIG. 2 (PDC T3 generation), for PEDV S1 or by feeding larger amounts of maize flour to the sows.

In addition, a more robust immune response may be obtained using carrier proteins. Fusion of the antigen to either the DC peptide or LTB both showed relatively good accumulation of the S1 antigen. These carrier peptides can enhance immunogenicity in some cases, including reports for PEDV[23, 24]. Future studies with these constructs will address whether an increase in immunogenicity is observed with the extended S1 region or on addition of LTB or the DC peptide. The maize system has many inherent properties making it amenable to development of practical low-cost oral vaccines for livestock. In addition to high expression levels, a plant-produced antigen should be stable to allow for a low cost of production and storage. Seeds such as maize grain have evolved to maintain proteins in a stable environment, allowing germination after years of dormancy, in contrast to vegetative tissue or fruits that undergo degradation shortly after harvest. This stability has been demonstrated for recombinant proteins that retain activity after being stored for years in the grain and allows for long-term storage, transport at ambient temperatures, and processing of the grain at will rather than a requirement to process large batches immediately upon harvest[19]. Stability can also be further increased by removal of oils by supercritical fluid extraction (SFE), a process we have demonstrated for other antigens[25]. Bioencapsulation of the antigen in maize grain has been shown to help maintain antigenic determinants during passage through the digestive system leading to a higher immune response relative to purified protein, and the immune response may also be enhanced upon SFE treatment as has been shown in other cases[25].

In conclusion, we have demonstrated high levels of expression of a recalcitrant antigen, PEDV spike protein, in transgenic maize. After optimization, this system should result in a heat-stable oral vaccine for PEDV that does not require a cold chain. Once the system is established for one PEDV strain it should be possible to develop maize lines to incorporate antigens for additional strains as needed.

FIG. 4 shows Pig antibody response. Serum neutralizing antibody response from the indicated groups (n=4) were assessed by fluorescent focus neutralization assay at 15 days post-challenge (dpc), as described in the methods section. At 15 dpc treatment groups containing S1 (one and two) showed significant differences with the control group (three) with p-values for each comparison substantially below 0.05. There was no significant difference in the titers between treatment groups one (injected S1) and two (orally-delivered maize S1). Groups received either two injected or two oral doses.

REFERENCES

[1] Gerdts, V., and Zakhartchouk, A. (2017) Vaccines for porcine epidemic diarrhea virus and other swine coronaviruses, *Veterinary microbiology* 206, 45-51.
[2] Guo, J., Fang, L., Ye, X., Chen, J., Xu, S., Zhu, X., Miao, Y., Wang, D., and Xiao, S. (2019) Evolutionary and genotypic analyses of global porcine epidemic diarrhea virus strains, *Transboundary and emerging diseases* 66, 111-118.
[3] Sun, D., Feng, L., Shi, H., Chen, J., Cui, X., Chen, H., Liu, S., Tong, Y., Wang, Y., and Tong, G. (2008) Identification of two novel B cell epitopes on porcine epidemic diarrhea virus spike protein, *Veterinary microbiology* 131, 73-81.
[4] Chang, S.-H., Bae, J.-L., Kang, T.-J., Kim, J., Chung, G.-H., Lim, C.-W., Laude, H., Yang, M.-S., and Jang, Y.-S. (2002) Identification of the epitope region capable of inducing neutralizing antibodies against the porcine epidemic diarrhea virus, *Molecules and cells* 14, 295-299.
[5] Makadiya, N., Brownlie, R., van den Hurk, J., Berube, N., Allan, B., Gerdts, V., and Zakhartchouk, A. (2016) S1 domain of the porcine epidemic diarrhea virus spike protein as a vaccine antigen, *Virology journal* 13, 1.
[6] Oh, J., Lee, K.-W., Choi, H.-W., and Lee, C. (2014) Immunogenicity and protective efficacy of recombinant S1 domain of the porcine epidemic diarrhea virus spike protein, *Archives of virology* 159, 2977-2987.
[7] Van Noi, N., and Chung, Y.-C. (2017) Optimization of expression and purification of recombinant S1 domain of the porcine epidemic diarrhea virus spike (PEDV-S1) protein in *Escherichia coli*, *Biotechnology & Biotechnological Equipment* 31, 619-629.
[8] Piao, D.-C., Lee, Y.-S., Bok, J.-D., Cho, C.-S., Hong, Z.-S., Kang, S.-K., and Choi, Y.-J. (2016) Production of soluble truncated spike protein of porcine epidemic diarrhea virus from inclusion bodies of *Escherichia coli* through refolding, *Protein expression and purification* 126, 77-83.
[9] Di-qiu, L., Jun-wei, G., Xin-yuan, Q., Yan-ping, J., Song-mei, L., and Yi-jing, L. (2012) High-level mucosal and systemic immune responses induced by oral administration with *Lactobacillus*-expressed porcine epidemic diarrhea virus (PEDV) S1 region combined with *Lactobacillus*-expressed N protein, *Applied microbiology and biotechnology* 93, 2437-2446.
[10] Hou, X., Jiang, X., Jiang, Y., Tang, L., Xu, Y., Qiao, X., Liu, M., Cui, W., Ma, G., and Li, Y. (2018) Oral Immunization against PEDV with Recombinant *Lactobacillus casei* Expressing Dendritic Cell-Targeting Peptide Fusing COE Protein of PEDV in Piglets, *Viruses* 10, 106.
[11] Bae, J.-L., Lee, J.-G., Kang, T.-J., Jang, H.-S., Jang, Y.-S., and Yang, M.-S. (2003) Induction of antigen-specific systemic and mucosal immune responses by feeding animals transgenic plants expressing the antigen, *Vaccine* 21, 4052-4058.
[12] Huy, N.-X., Kim, S.-H., Yang, M.-S., and Kim, T.-G. (2012) Immunogenicity of a neutralizing epitope from porcine epidemic diarrhea virus: M cell targeting ligand fusion protein expressed in transgenic rice calli, *Plant cell reports* 31, 1933-1942.
[13] Huy, N.-X., and Kim, M.-Y. (2019) Improved expression of porcine epidemic diarrhea antigen by fusion with cholera toxin B subunit and chloroplast transformation in *Nicotiana tabacum*, *Plant Cell, Tissue and Organ Culture (PCTOC)*, 1-11.
[14] Lamphear, B. J., Jilka, J. M., Kesl, L., Welter, M., Howard, J. A., and Streatfield, S. J. (2004) A corn-based delivery system for animal vaccines: an oral transmissible gastroenteritis virus vaccine boosts lactogenic immunity in swine, *Vaccine* 22, 2420-2424.
[15] Hayden, C. A., Fischer, M. E., Andrews, B. L., Chilton, H. C., Turner, D. D., Walker, J. H., Tizard, I. R., and Howard, J. A. (2015) Oral delivery of wafers made from HBsAg-expressing maize germ induces long-term immunological systemic and mucosal responses, *Vaccine* 33, 2881-2886.
[16] Streatfield, S. J., Mayor, J. M., Barker, D. K., Brooks, C., Lamphear, B. J., Woodard, S. L., Beifuss, K. K., Vicuna, D. V., Massey, L. A., and Horn, M. E. (2002) Development of an edible subunit vaccine in corn against enterotoxigenic strains of *Escherichia coli*, *In Vitro Cellular & Developmental Biology-Plant* 38, 11-17.
[17] Man, K., Yang, B., Xue, J., Qin, X., Zhou, H., Xu, F., Xu, C., Yang, F., Zhang, L., and Li, X. (2014) Expression of core neutralizing epitope gene of porcine epidemic diarrhea virus in maize, *Journal of Agricultural Science and Technology (Beijing)* 16, 28-35.

[18] Komari, T., Hiei, Y., Saito, Y., Murai, N., and Kumashiro, T. (1996) Vectors carrying two separate T-DNAs for co-transformation of higher plants mediated by *Agrobacterium tumefaciens* and segregation of transformants free from selection markers, *Plant Journal* 10, 165-174.

[19] Hayden, C. A., Egelkrout, E. M., Moscoso, A. M., Enrique, C., Keener, T. K., Jimenez-Flores, R., Wong, J. C., and Howard, J. A. (2012) Production of highly concentrated, heat-stable hepatitis B surface antigen in maize, *Plant Biotechnology Journal* 10, 979-984.

[20] Ishida, Y., Saito, H., Ohta, S., Hiei, Y., Komari, T., and Kumashiro, T. (1996) High efficiency transformation of maize (*Zea mays* L.) mediated by *Agrobacterium tumefaciens*, *Nat Biotechnol* 14, 745-750.

[21] Hood, E. E., Helmer, G. L., Fraley, R. T., and Chilton, M. D. (1986) The hypervirulence of *Agrobacterium tumefaciens* A281 is encoded in a region of pTiBo542 outside of T-DNA, *J Bacteriol* 168, 1291-1301.

[22] Hood, E. E., Devaiah, S. P., Fake, G., Egelkrout, E., Teoh, K., Requesens, D. V., Hayden, C., Hood, K. R., Pappu, K. M., Carroll, J., and Howard, J. A. (2012) Manipulating corn germplasm to increase recombinant protein accumulation, *Plant Biotechnology Journal* 10, 20-30.

[23] Wang, X., Wang, L., Huang, X., Ma, S., Yu, M., Shi, W., Qiao, X., Tang, L., Xu, Y., and Li, Y. (2017) Oral delivery of probiotics expressing dendritic cell-targeting peptide fused with porcine epidemic diarrhea virus COE antigen: a promising vaccine strategy against PEDV, *Viruses* 9, 312.

[24] Chang, Y.-C., Chang, C.-Y., Tsai, P.-S., Chiou, H.-Y., Jeng, C.-R., Pang, V. F., and Chang, H.-W. (2018) Efficacy of heat-labile enterotoxin B subunit-adjuvanted parenteral porcine epidemic diarrhea virus trimeric spike subunit vaccine in piglets, *Applied microbiology and biotechnology* 102, 7499-7507.

[25] Hayden, C. A., Smith, E. M., Turner, D. D., Keener, T. K., Wong, J. C., Walker, J. H., Tizard, I. R., Jimenez-Flores, R., and Howard, J. A. (2014) Supercritical fluid extraction provides an enhancement to the immune response for orally-delivered hepatitis B surface antigen, *Vaccine* 32, 1240-1246.

LIST OF SEQUENCES

SEQ ID NO: 1 PEDV S1 (US)
SEQ ID NO: 2 PEDV S1ext
SEQ ID NO: 3 PEDV S1 (US) encoded peptide
SEQ ID NO: 4 PEDV S1(ext) encoded peptide
SEQ ID NO: 5 BAASS sequence
SEQ ID NO: 6 BAASS encoded peptide
SEQ ID NO: 7 ABI Optimized PEDV-M (US)
SEQ ID NO: 8 Amino acid sequence PEDV M (US) encoded peptide
SEQ ID NO: 9 PEDV S1 DR13 (South Korean Strain) encoded polypeptide
SEQ ID NO: 10 ABI Optimized PEDV-N (US
SEQ ID NO: 11 Amino acid sequence PEDV-N encoded peptide
SEQ ID NO: 12 PEDV COE
SEQ ID NO: 13 DC3
SEQ ID NO: 14 LTB heat labile peptide
SEQ ID NO: 15 LTB heat labile encoded peptide
SEQ ID NO: 16 Promoter pr25-globulin 1
SEQ ID NO: 17 Promoter pr39-27 kDa gamma zein
SEQ ID NO: 18 Promoter P44 sequence
SEQ ID NO: 19 KDEL ER targeting sequence
SEQ ID NO: 20 PEDV sequence encoding entire viral protein, (GenBank Accession No. KF272920)
SEQ ID NO: 21 Spike protein sequence encoded by SEQ ID NO: 16 (above) (See GenBank AGO58924.1)
SEQ ID NO: 22 Spike protein of Korean PEDV strain of Gen Bank AAM19716
SEQ ID NO: 23 China PEDV strain of GenBank AFL02627.1
SEQ ID NO: 24 HDEL sequence
SEQ ID NO: 25 DR13 nucleotide sequence

What is claimed is:

1. A method of producing a protective response to Porcine Epidemic Diarrhea Virus (PEDV) in an animal, the method comprising,
    a) orally administering to said animal a composition comprising a plant or a plant product comprising the Spike (S1) protein of PEDV, said protein comprising SEQ ID NO: 3, 4, 9, 21 or 22 or a sequence having at least 90% identity to SEQ ID NO: 3, 4, 9, 21 or 22 or a functional fragment of said S1 protein expressed at levels of at least 10 mg/kg in seed of said plant, wherein said S1 protein is encoded by a nucleotide sequence comprising SEQ ID NO: 1, 2, or 25 or a sequence having at least 90% identity to SEQ ID NO: 1, 2, or 25; and
    b) producing a protective response to said PEDV in said animal.

2. The method of claim 1, wherein said protective response comprises a serum antibody response in said animal.

3. The method of claim 1, wherein said serum antibody response is at least 20 times greater than the serum antibody response in an animal not administered said vaccine.

4. The method of claim 1, wherein milk of said animal comprises an antibody to said S1 protein.

5. The method of claim 1, wherein said composition comprises a seed or an embryo of a seed.

6. A vaccine comprising a plant-produced polypeptide of the Spike (S1) protein, the vaccine comprising a plant or plant product comprising a construct comprising,
    (a) a promoter preferentially directing expression to seed tissue of a plant;
    (b) a nucleic acid molecule encoding a S1 polypeptide of said PEDV comprising SEQ ID NO: 3, 4 or 9 or a sequence having at least 90% identity to SEQ ID NO: 3, 4, 9, 21 or 22 or a functional fragment operably linked to said promoter, wherein said S1 protein is encoded by a nucleotide sequence comprising SEQ ID NO: 1, 2, or 25 or a sequence having at least 90% identity to SEQ ID NO: 1, 2, or 25; and
    (c) a nucleic acid molecule targeting expression of said polypeptide in the endoplasmic reticulum of said plant; and expressing said S1 polypeptide in said plant at levels of at least 1 mg/kg of seed of said plant.

7. The vaccine of claim 6, wherein said construct further comprises a sequence selected from a sequence encoding the core neutralizing epitope (CEO) peptide of SEQ ID NO: 12, a sequence encoding the heat-labile enterotoxin (LTB) peptide of SEQ ID NO: 15, or the dendritic cell targeting sequence (DC3) peptide of SEQ ID NO: 13 or a combination thereof.

8. The vaccine of claim 6, wherein said construct comprises two copies of said nucleic acid molecule encoding a S1 polypeptide.

9. The vaccine of claim 8, wherein said construct comprises two copies of a nucleic acid molecule selected from sequence encoding the COE peptide of SEQ ID NO: 12, a sequence encoding the LTB heat labile peptide of SEQ ID NO: 15 or the DC3 peptide of SEQ ID NO: 13 and a sequence encoding an endoplasmic reticulum retaining sequence or a combination thereof.

10. The vaccine of claim 6, wherein said S1 protein or fragment thereof is expressed in said plant or plant product at levels of 10 mg/kg of whole seed.

11. The vaccine of claim 6, wherein said S1 protein comprises a nucleic acid molecule encoding SEQ ID NO: 3, 4, 9, 21 or 22 or a sequence having at last 95% identity thereto.

12. The vaccine of claim 6, wherein said S1 protein comprises SEQ ID NO: 3, 4, 9, 21 or 22 or a functional fragment thereof.

13. The vaccine of claim 6, wherein said S1 protein is encoded by a sequence comprising SEQ ID NO: 1, 2, or 25 or a sequence having at least 95% identity thereto.

14. A method of expressing a polypeptide of Spike (S1) protein or functional fragment thereof of Porcine Epidemic Diarrhea Virus (PEDV) the method comprising, introducing into a plant a construct comprising, (a) a promoter preferentially directing expression to seed tissue of a plant;
(b) a nucleic acid molecule encoding a S1 polypeptide of said PEDV comprising SEQ ID NO: 3, 4 or 9 or a sequence having at least 90% identity to SEQ ID NO: 3, 4, 9, 21 or 22 or a functional fragment operably linked to said promoter, wherein S1 protein is encoded by a nucleotide sequence comprising SEQ ID NO: 1, 2, or 25 or a sequence having at least 90% identity to SEQ ID NO: 1, 2, or 25; and
(c) a nucleic acid molecule targeting expression of said polypeptide in the endoplasmic reticulum of said plant; and expressing said S1 polypeptide in said plant at levels of at least 1 mg/kg of seed of said plant.

15. The method of claim 14, wherein said construct further comprises a sequence selected from a sequence encoding the COE peptide of SEQ ID NO: 12, a sequence encoding the LTB heat labile peptide of SEQ ID NO: 15 or the DC3 peptide of SEQ ID NO: 13 or a combination thereof.

16. The method of claim 14, wherein said construct comprises two copies of said nucleic acid molecule encoding a S1 polypeptide.

17. The method of claim 16, wherein said construct comprises two copies of a nucleic acid molecule selected from sequence encoding the COE peptide of SEQ ID NO: 12, a sequence encoding the LTB heat labile peptide of SEQ ID NO: 15 or a combination thereof.

18. The method of claim 14, wherein said S1 protein or fragment thereof is expressed in said plant or plant product at levels of at least 10 mg/kg of whole seed.

* * * * *